(12) United States Patent
Rao et al.

(10) Patent No.: US 11,685,892 B2
(45) Date of Patent: Jun. 27, 2023

(54) METHODS TO INCORPORATE MACHINE LEARNING ANALYTICS FOR OPTIMIZING PROTEIN PURITY, POTENCY AND QUALITY IN AN ON-DEMAND PRODUCTION SYSTEM FOR POINT-OF-CARE DELIVERY

(71) Applicant: UNIVERSITY OF MARYLAND, BALTIMORE COUNTY, Baltimore, MD (US)

(72) Inventors: Govind Rao, Ellicott City, MD (US); Yordan Kostov, Columbia, MD (US); Benjamin Punshon-Smith, Gwynn Oak, MD (US); Rajani Adiga, Laurel, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 17/055,149

(22) PCT Filed: May 15, 2019

(86) PCT No.: PCT/US2019/032350
§ 371 (c)(1),
(2) Date: Nov. 13, 2020

(87) PCT Pub. No.: WO2020/068173
PCT Pub. Date: Apr. 2, 2020

(65) Prior Publication Data
US 2021/0189322 A1    Jun. 24, 2021

Related U.S. Application Data

(60) Provisional application No. 62/671,566, filed on May 15, 2018.

(51) Int. Cl.
     *C12M 3/00*      (2006.01)
     *B01L 3/00*      (2006.01)
     (Continued)

(52) U.S. Cl.
     CPC ............ *C12M 41/48* (2013.01); *C12M 23/54* (2013.01); *C12M 47/12* (2013.01)

(58) Field of Classification Search
     CPC .............................. C12M 41/48; C12M 47/12
     See application file for complete search history.

(56) References Cited

U.S. PATENT DOCUMENTS

| | | |
|---|---|---|
| 9,388,373 B2 | 7/2016 | Rao et al. |
| 9,982,227 B2 | 5/2018 | Rao et al. |

(Continued)

FOREIGN PATENT DOCUMENTS

WO    WO2012171030 A2    12/2012

OTHER PUBLICATIONS

S. S. Farid, 2007, Process economics of industrial monoclonal antibody manufacture. *J. Chromatogr. B* 848, 8-18.

(Continued)

*Primary Examiner* — Nathan A Bowers
(74) *Attorney, Agent, or Firm* — Tristan A. Fuierer; Casimir Jones, SC

(57) ABSTRACT

The present invention relates to cell free protein manufacturing, and more particularly, for integrating machine learning into a portable cell-free bioprocessing system for producing proteins with increased and consistent purity, potency and quality wherein such proteins are prepared on-demand and for point-of-care delivery.

19 Claims, 38 Drawing Sheets

(51) Int. Cl.
*C12M 1/36* (2006.01)
*C12M 1/00* (2006.01)

(56) References Cited

U.S. PATENT DOCUMENTS

| | | | |
|---|---|---|---|
| 10,435,664 B2 | 10/2019 | Rao et al. | |
| 10,774,304 B2 | 9/2020 | Rao et al. | |
| 2014/0148350 A1* | 5/2014 | Spetzler | G01N 33/574 436/501 |
| 2014/0356849 A1 | 12/2014 | Wikswo et al. | |
| 2016/0222341 A1 | 8/2016 | Rao et al. | |
| 2018/0038850 A1* | 2/2018 | Wang | G01N 33/5038 |
| 2018/0322941 A1* | 11/2018 | Krishnan | G16H 40/63 |

OTHER PUBLICATIONS

J. Conner et al., 2014, The Biomanufacturing of Biotechnology Products in *Biotechnology Entrepreneurship*. pp. 351-385.
Finn, M. in Top Markets Series 2016 (U.S. Department of Commerce, International Trade Administration, http://trade.gov/topmarkets/pdf/Pharmaceuticals_Top_Markets_Reports).
Peñalber-Johnstone C, Ge X, Tran K, Selock N, Sardesai N, Gurramkonda C, Pilli M, Tolosa M, Tolosa L, Kostov Y, Frey DD, Rao G. 2017, Optimizing cell-free protein expression in CHO: Assessing small molecule mass transfer effects in various reactor configurations. *Biotechnol Bioeng.* Jul.;114(7):1478-1486.
Tran K, Gurramkonda C, Cooper MA, Pilli M, Tarris J, Selock N, Han TC, Tolosa M, Zuber A, Peñalber-Johnstone C, Dinkins C, Pezeshk N, Kostov Y, Frey DD, Tolosa L, Wood D, Rao G., 2017, Cell-Free Production of a Therapeutic Protein: Expression, Purification, and Characterization of Recombinant Streptokinase Using a CHO Lysate. *Biotechnol Bioeng.* Aug. 26. doi: 10.1002/bit.26439.
G. Rao et al., 2016, Microscale bioprocessing system for therapeutic protein on-demand production. U.S. Pat. No. 9,388,373.
Adiga R, et al. Jul. 2018. Biological Medicines on Demand: A platform for therapeutic cGMP protein manufacturing at the point-of-care. *Nature Biomedical Engineering*, V.2, 675-686(2018).
A. K. Brödel, A. Sonnabend, S. Kubick, 2014, Cell-free protein expression based on extracts from CHO cells. *Biotechnol. Bioeng.* 111, 25-36.
C. E. Hodgman, M. C. Jewett, 2012, Cell-free synthetic biology: Thinking outside the cell. *Metab. Eng.* 14, 261-269.
Adamo, A. et al. 2016, On-demand continuous-flow production of pharmaceuticals in a compact, reconfigurable system. *Science* 352, 61-67.
Pardee, K. et al. 2016, Portable, on-demand biomolecular manufacturing. *Cell* 167, 248-259.e212.
Boles, K.S. et al. 2017, Digital-to-biological converter for on-demand production of biologics. *Nat Biotech* 35, 672-675.
Airen IO. 2011. Genome-wide functional genomic analysis for physiological investigation and improvement of cell-free protein synthesis. Ph.D. Dissertation, Stanford University.
Guo H, Li X, Frey DD. 2014. Development of Chromatofocusing Techniques Using Mixed-Mode Column Packings for Protein Separations. *J. Chromatogr. A*, 1323: 57-65.
Guest DW. 1997, Evaluation of simulated moving bed chromatography for pharmaceutical process development, *J. Chromatogr. A*, 760, 159-162.
Ng, C.K.S., Rousset, F., Valery, E, bracewell, D.G., Sorensen, E. 2014. Design of high productivity sequential multicolumn chromatography for antibody capture, *Food Bioprocess Processing*, 92, 233-241.
Ariffin, A.A.B., Hashim, U., Salam, F., Ishak, Z., Uda, M.N.A., Adam, T. 2014. COMSOL Multiphysics simulation for microfluidic separator as sample delivery system in sensing domain, Proc. Fifth Intern. Conf. Intelligent Systems, *Modelling, and Simulations*, pp. 183-186.
Ward AC, Smith L, de Koning JP, van Aesch Y, Touw IP. 1999. Multiple Signals Mediate Proliferation, Differentiation, and Survival from the Granulocyte Colony-stimulating Factor Receptor in Myeloid 32D Cells, *The Journal of Biological Chemistry*, 274(21): 14956-14962.
Panopoulos AD, Watowich SS. 2008, Granulocyte Colony-Stimulating Factor: Molecular Mechanisms of Action During Steady State and 'Emergency' Hematopoiesis. *Cytokine.* 42(3): 277-288.
Demetri GD, Griffin JD. 1991. Granulocyte colony-stimulating factor and its receptor. *Blood.* 78(11):2791-808.
Rossetti M, Gregori S, Roncarolo MG. 2010, Granulocyte-colony stimulating factor drives the in vitro differentiation of human dendritic cells that induce anergy in naïve T cells. *Eur J Immunol.* 40(11): 3097-3106.
Gurramkonda C, Mupparapu K, Abouzeid R, Kostov Y, Rao G. 2014, Fluorescence-based method and a device for rapid detection of microbial contamination. *PDA J Pharm Sci Technol.* 68(2): 164-71.
Al-Adhami M, Tilahun D, Rao G, Gurramkonda C, Kostov Y. 2017, Rapid Detection of Microbial Contamination Using a Microfluidic Device. *Methods Mol Biol.* 1571:287-299.
Yang M, Sun S, Kostov Y, Rasooly A. 2010, Lab-on-a-Chip for carbon nanotubes based immunoassay detection of Staphylococcal Enterotoxin B (SEB). *Lab Chip.* 10(8), 1011-7.
Yang, M., Kostov, Y., Bruck, H., Rasooly, A. 2008, Carbon Nanotubes with Enhanced Chemiluminescence (CNT-ECL) Immunoassay for CCD-based Detection of Staphylococcal Enterotoxin B (SEB), *Food. Anal. Chem.* 80(22), 8532-8537.
Yang, M., Kostov, Y., Rasooly, A. 2008, Carbon nanotubes based optical immunodetection of Staphylococcal Enterotoxin B (SEB) in food. *Int. J. Food Microbiology* 127(1), 78-83.
Karhunen, J, et al, 1997, A Class of Neural Networks for Independent Component Analysis, *IEEE Transactions on Neural Networks*, vol. 8, No. 3, May 1997, pp. 486-504.
Szu, Harold & Hsu, C., 1999, Unsupervised neural network learning for blind sources separation, 30-38. 10.1109/SBRN.1998.730990.
Caschera, F. et al., 'Coping with complexity: machine learning optimization of cell-free protein synthesis', Biotechnology and bioengineering. Sep. 2011, vol. 108, No. 9, pp. 2218-2228.
Caschera, F., 'Bacterial cell-free expression technology to in vitro systems engineering and optimization', Synthetic and systems Biotechnology, 2017, vol. 2, pp. 97-104.
Jiang, L. et al., 'Cell-free protein synthesis enabled rapid prototyping for metabolic engineering and synthetic biology', Synthetic and systems Biotechnology, 2018, vol. 3, pp. 90-96.
Extended European Search Report, corresponding to European Patent Application No. 19866780,0, dated Feb. 25, 2022.

\* cited by examiner

E

F

| | | | |
|---|---|---|---|
| | 10 | | Male Luer Lock (2) |
| Fittings | 11 | | Check Valve (2) |
| | 12 | | P-656 - Luer Assembly 10-32 Female to Male, PEEK (5) |
| | 13 | | Female Luer Lock (10) |
| | 14 | | Y Junction PP 1/32" Hose Barb (8) 1/32" OD Tubing to 10-32 Thread Male (9) |
| | 15 | | |
| Tubing | 16 | | Silicone Tubing 1/32" ID 3/32" OD Total Length (198 cm) |
| | 17 | | Peek Tubing .02" ID .06" OD Total Length (27 cm) |
| Syringes | 18 | | BD Sterile Luer Lock 10 mL Syringe (1) |
| | 19 | | BD Sterile Luer Lock 60 mL Syringe (4) |
| | 20 | | CAST Integrated Chip Includes: (1) Micro-fluidic Mixer (1) 100 uL Capture Column |

Legend

| Category | Part # | 2D Drawing | Part Description |
|---|---|---|---|
| Single Use Items | 1 | | Slide-A-Lyzer Dialysis Cassette 10 Kda MWCO 0.5 - 3 mL |
| | 2 | | 1 mL DEAE Polish Column 10/32 Thread Male and Female (1) |
| | 3 | | 18 G Blunt Red Needle (1) |
| | 4 | | Sterile 5 μm PVDF Filter (1) |
| | 5 | | 1/16" Barbed x 1/16" Barbed 2 PSI Check Valve (3) |
| | 6 | | Nunc 15 mL Sterile PP Centrifuge Tubes (1) |
| Mounted Parts | 7 | | UV Flow Cell (2) |
| | 8 | | Pinch Valve (6) |
| | 9 | | Load Cell Pressure Sensor (4) |

Figure 5B

Dissolved oxygen                               pH

| Sample number | Purity (%) |
|---|---|
| TRS-I18-003-01 | 97.3 |
| TRS-I18-003-02 | 98.5 |
| TRS-I18-003-03 | 99.1 |
| TRS-I18-003-04 | 98.9 |
| TRS-I18-003-05 | 98.7 |
| TRS-I18-003-06 | 98.0 |
| TRS-I18-003-07 | 98.4 |
| TRS-I18-003-08 | 98.9 |
| TRS-I18-003-09 | 99.2 |
| TRS-I18-003-10 | 98.8 |
| TRS-I18-003-11 | 99.0 |

Elution profiles analyzed:
- Input: ICA top 4 component weights
- Structure: 10 neuron hidden layer,
- Output: 3 dimension layer: $[p_1, p_2, p_3]$
  $p_1 \geq 99\%$, $99\% > p_2 \geq 98\%$, $p_3 \leq 98\%$.
- Training: Levenberg-Marquardt 12-2-2

Figure 10 C

METHODS TO INCORPORATE MACHINE LEARNING ANALYTICS FOR OPTIMIZING PROTEIN PURITY, POTENCY AND QUALITY IN AN ON-DEMAND PRODUCTION SYSTEM FOR POINT-OF-CARE DELIVERY

CROSS-REFERENCE TO RELATED APPLICATIONS

This application is filed under the provisions of 35 U.S.C. § 371 and claims the priority of International Patent Application No. PCT/US2019/032350 filed on May 15, 2019 which in turn claims priority to U.S. Provisional Application No. 62/671,566, filed on May 15, 2018, the contents of all is hereby incorporated by reference herein for all purposes.

GOVERNMENT RIGHTS IN INVENTION

This invention was made with government support under Grant Number N66001-13-C-4023 awarded by the Defense Advanced Research Projects Agency (DARPA). The government has certain rights in the invention.

BACKGROUND OF THE INVENTION

Field of the Invention

The present invention relates to cell free protein manufacturing, and more particularly, for integrating machine learning into a portable cell free bioprocessing system for producing proteins with increased and consistent purity, potency and quality wherein such proteins are prepared on-demand and for point-of-care delivery.

Background of the Related Art

Protein therapeutics, also known as biologics, are currently manufactured at centralized facilities according to rigorous protocols collectively referred to as Current Good Manufacturing Practices (cGMP) (1, 2). Biologics are currently produced in a centralized manufacturing facility with large scale (>10,000 liters) cell cultures, and with the necessary large volume separation, purification, formulation, packaging, and distribution infrastructure (e.g. a typical Merck, Pfizer or Genentech plant). The time period from a cell bank to the final delivery of the therapeutic vial is on the order of 6-8 weeks under ideal conditions and produces batches of around 10 Kg bulk protein. Every step needs to be individually developed, scaled-up, optimized and validated in a manufacturing setting. The final product will also have an expiration date and is either shipped lyophilized or via a cold chain, which must also be documented.

Since such facilities require multiple years to design, build, activate, and qualify, they are unsuited to respond to rapid changes in demand. Furthermore, should a manufacturing facility go offline, as in the event of a natural disaster, it is likely to result in severe shortages that would adversely impact public health, as has happened in Puerto Rico. Further, the pharmaceutical industry of today suffers from enormous expenditures that nonetheless result in relatively few new drugs and therapies being introduced to the market (3).

The availability of biologics for treatment of patients in non-conventional healthcare settings, such as combat zones, remote areas of the world, or during natural disasters is limited by the need for extensive manufacturing facilities and transport via cold chain through potentially disrupted infrastructure. Further, planning for the exact nature and amount of biologics necessary in a constantly-changing emergent setting is difficult. The critical need for a nimble, portable platform for manufacture of any needed therapeutic biologic for immediate point-of-care administration to patients regardless of location was originally articulated by the Defense Advanced Research Projects Agency (DARPA) specifically for use on the battlefield. Biologically-derived Medicines on Demand (Bio-MOD) was developed in response to this challenge and funded by showing the biologics manufacturing at the point-of-care (4-7).

The idea of compounding a drug requested by a doctor for production at the bedside is already being tried in a hospital setting using conventional cell culture manufacture of biotherapeutics. Such an approach appears to have the potential to circumvent lengthy regulatory approvals, as the biologics would be made under prescription for a particular patient and would be regarded as a form of compounding. However, there are downsides because of lack of consistency and/or potency.

Thus, there is a need for production of biological medicines in real-time and/or on-demand to provide therapeutic proteins in hospitals or remote locations. Also, there is a need for incorporation of in-process testing, statistical analysis, sterility/potency validation and feedback mechanism for quality assurance to reduce reliance on expensive laboratory testing equipment in lab settings. As such, the present invention provides for additional detailed characterization of individual lots to demonstrate the rigor, consistency and robustness of cell-free real-time biomanufacturing by integration of on-board analytics to a machine learning driven approach that has the potential to bring exceptional regulatory rigor to the process.

SUMMARY OF THE INVENTION

The present invention provides for an integrated, portable and compact bioprocessing system and method for the production of proteins with built-in confirmation of purity and consistency of produced protein.

In one aspect, the present invention provides a portable and compact cell-free bioprocessing system for the production of on-demand synthesized protein for point-of-care delivery, the system comprising:
a. a protein expression module for producing the on-demand synthesized protein; and
b. a protein purification module for purification of the demand synthesized protein, wherein each module is associated with on-board analytics and wherein the on-board analytics are integrated to a machine learning system to analyze properties of the bioprocessing system during the production and synthesis of the protein to provide data on the purity, potency and quality of the on-demand synthesized protein.

In the present invention, the protein expression module comprises at least one dialysis cassette or reactor for inclusion of cell lysate, reaction mixture and DNA or mRNA for production of the on-demand synthesized protein. The cell lysate may be from CHO cells or $E.\ coli$ cells. Importantly the lysate can be combined with a buffer in a mixer discussed further herein. Besides the cell lysate other reaction component are include in the production module such as amino acids, nucleotides, co-factors, enzymes, ribosomes, tRNA, polymerases and transcriptional factors. Still further, the reaction mixture may include components selected from the group consisting of salts, polymeric compounds, cyclic AMP, inhibitors for protein or nucleic acid degrading enzymes, inhibitors or regulators of protein synthesis, oxidation/reduction adjusters, non-denaturing surfactants, and buffer components.

The purification module comprises a metal ion affinity chromatography column for initial purification and an ion-exchange column for a polishing step of the expressed target protein. Further the purification module may comprise a multiplicity of programmable syringe pumps, UV sensors and pressure sensors to monitor the two-step purification process.

The on-board analytics comprise multiple sensors for collecting data during the production process to be analyzed by a machine learning system, including but not limited to a cloud based system or an integrated physical server connected to the system or a near-by server with access through a smartphone. The multiple sensors are used to measure for dissolved oxygen, pH, absorbance, pressure and temperature. Preferably, the machine learning system uses a blind source separation (BSS) algorithm such as independent-component analysis (ICA) that extracts independent source signals when the source signals are active simultaneously and is a BSS algorithm depending on using the Artificial Neural Networks.

In another aspect of the present invention provides for a portable, cell-free bioprocessing system for on-site synthesis and delivery of an expressed target protein and verification of purity and consistency of the expressed target protein, the system comprising:
a. a protein expression module wherein the protein expression module comprises at least one dialysis cassette including cell lysate, reaction mixture and DNA or RNA for a target protein;
b. a purification module, wherein the purification module comprises a metal ion affinity chromatography column for initial purification and an ion-exchange column for a polishing step of the expressed target protein; and
c. an artificial intelligence (AI) machine learning module to collect and store data of real-time testing of the expressed target protein to provide an output comparison to previously prepared proteins in the system.

In yet another aspect, the purification module comprises a multiplicity of programmable syringe pumps (2 to 6), at least two UV sensors from about 3 to 5 pressure sensors (preferably 4) to monitor the two-step purification process, which uses an immobilized metal ion affinity chromatography (IMAC) column as a first step, and an ion-exchange resin containing positively charged groups, such as diethylaminoethyl groups (DEAE) column for the second (polishing) step. The pumps operate in the pressure range of 0.2-30 psi and dispense at a rate of 0.004 to 3.0 ml min$^{-1}$. Importantly, the system is designed to provide flexibility and compatibility, allowing for customization of the script, columns, buffers and flow rates according to the requirements of the user.

In a further aspect, the present system provides for data collection to be analyzed by machine learning to provide a fingerprint profile for each batch of a specific protein thereby providing information on product quality and potency of the produced protein thereby replacing off-line analysis tools such as NMR and Mass spectroscopy. The data is extracted from each run, collected and analyzed by a mathematical or computational model for informational processing. Output date provide statistical analysis on the properties of the produced protein when compared to previous inputs thereby providing a fingerprint of the produced protein relative to previously produced proteins.

In yet another aspect, the present invention provides for a method of analyzing the purity and quality of a protein produced in a portable, cell-free bioprocessing system for on-site synthesis and delivery of an expressed protein, the method comprising:
a. providing pressure and UV sensor data during the production process for the produced protein;
b. transmitting the data to a computer aided classification system;
c. extracting features from the data with the computer aided classification system for classifying the protein and process conditions, wherein extracted features characterize the produced protein and such sample characterization is compared to characterization of previously extracted features to provide classified features of the produced protein;
d. applying an unsupervised clustering process to the classified features to provide a plurality of output clusters to provide enhanced identification of the produced protein.

In another aspect, the present invention provides for a portable system and method for on-demand production of a therapeutic protein, wherein the therapeutic protein exhibits increased potency due to the timely synthesis and substantially immediate delivery of protein. Preferably, the newly synthesized proteins are delivered to a patient within one hour, to one day, to two weeks. Preferably any refrigeration is at a temperature above freezing from 0 to 6° C. Any freezing of the proteins is preferably a single event with temperatures ranging from about −2° C. to about −10° C.

In yet another aspect, the present invention provides for a portable system and method for on-demand production of a protein, wherein the produced protein can be delivered continuously or as a bolus as it is produced and as it happens physiologically, that being, where the body produces needed proteins over an extended time in vivo and when needed.

To achieve at least the above aspects, in whole or in part, there is provided a bioprocessing system comprising a production module for producing a protein, a purification module for receiving the protein from the production module for purifying the protein from reagents and an artificial neural network for providing data on the produced protein relative to previously produced proteins. The bioprocessing system may further comprise a processor for controlling and/or monitoring at least the production module and/or the purification module. The processor is communicatively connected to at least the production module and/or purification module to control the timing, temperature and other parameters necessary for optimizing the production and purification of the synthesized proteins to provide a sufficient amount of or a therapeutic dosage of the synthesized protein. Such length of time in the production module and/or purification module may be used to affect the potency and/or activity of the synthesized protein and such data is easily collected and process with the included access to the artificial neural network.

The system may further comprise the use of a smartphone in the analysis process. The numerical or analysis data is easy transferred to a smart phone app, transferred through a smartphone to a server that has a program to evaluate the data and further processing of a classification of data methods by an artificial intelligence algorithm with a final integration of data into an output that is transferred back to the user and system. The process involves the association of data of the testing results and outputs for final review that can include the visual data in bar graphs, frequency graphs, and/or audio signals.

Additional advantages, aspects, and features of the invention will be set forth in part in the description which follows and in part will become apparent to those having ordinary skill in the art upon examination of the following or may be learned from practice of the invention. The aspects and advantages of the invention may be realized and attained as particularly pointed out in the appended claims.

BRIEF DESCRIPTION OF THE FIGURES

FIG. 1A is a photograph of the suitcase-sized system and the actual components with dimensions.

FIG. 2A shows UV1 traces showing the first stage (affinity column) purification.

FIG. 3 Cont. (i) shows (C) and (D) showing the corresponding pressure profiles from the integrated pressure sensors measuring the pressure at the back of each of the Bio-MOD syringe pumps; FIG. 3 Cont. (ii) shows (E) and (F) showing the corresponding silver stained SDS-PAGE. Each lane was loaded with 20 μL of samples taken from 100 μL fractions of polished samples collected in the polishing window.

FIG. 12A shows the fluorescence spectra of the acrylodan-labelled GBP showing quenching of fluorescence in the presence of glucose; FIG. 12B shows the binding isotherm for glucose in GBP; FIG. 12C shows the ELISA assay of harvest and purified fractions of EPO run 085. The measures of centre and error bars represent the mean and s.e.m. for n=3.

DETAILED DESCRIPTION OF THE INVENTION

Figure 1:
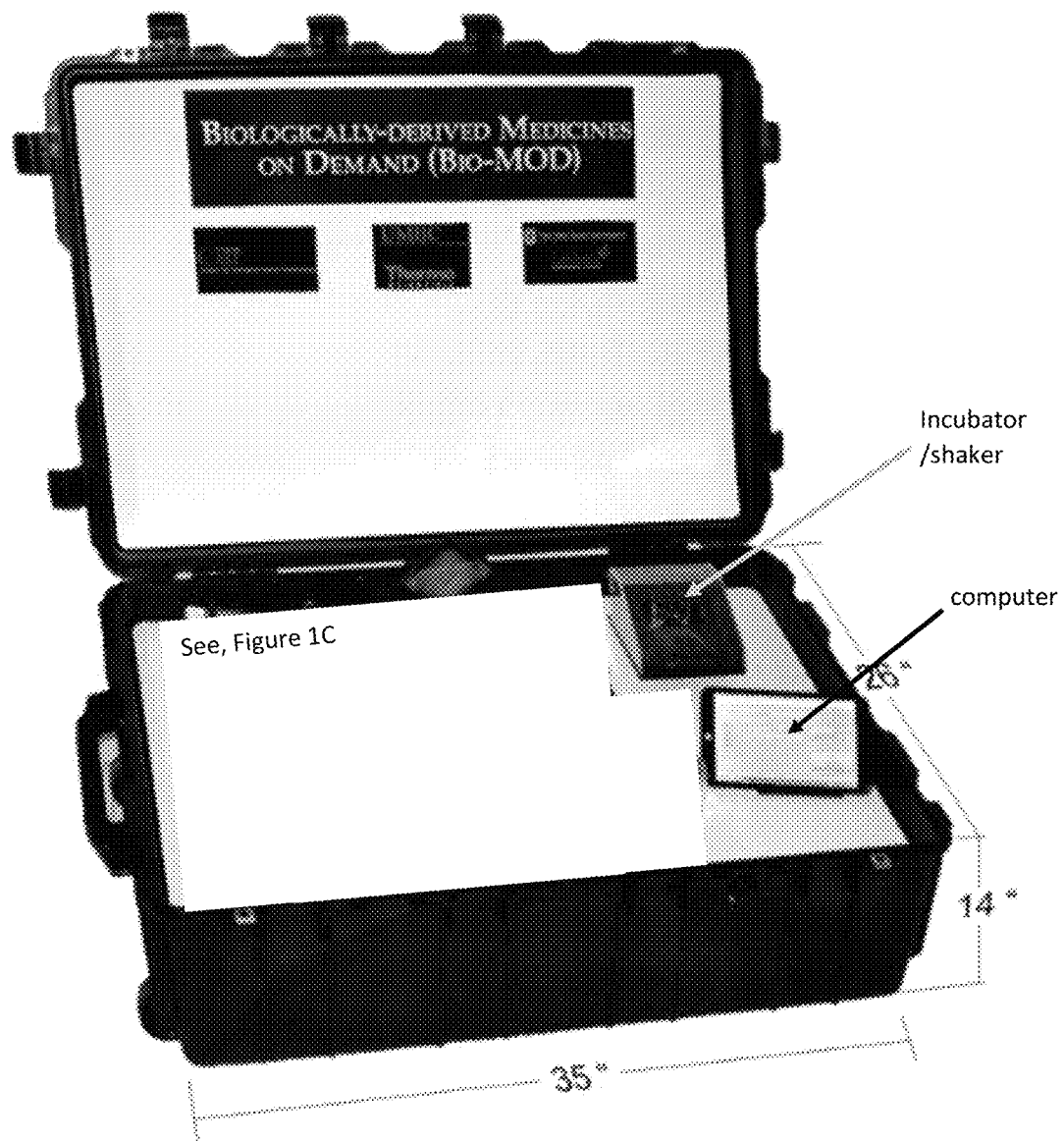
FIGS. 1A, B, C and D show the Biologically-derived Medicine on "Bio-MOD" Demand System.
FIG. 1B shows a process schematic wherein the system has access to a machine learning system to evaluate the end product.
FIG. 1C shows the schematic of the single-use expression and 2-step (affinity and ion-exchange) purification device of the present invention. The components shown in FIG. 1C include incubator/shaker holding the cassette (10,000 MWCO bioreactor); temperature-controller; robotic syringe pumps (i-v) which dispense the lysate and buffers: (i) 10-mL syringe, (ii-v) 60-89 mL syringes; steady lysate extractor or holder for cassette reactor; 5 μm syringe filter (Millex®-SV PVDF membrane, Merck Millipore Ltd., Cork, Ireland); microfluidic mixer developed in-house; two-way pinch valves (shown as a, b, and c); 1 mL His-Pur™ Co affinity column (ThermoFisher Scientific, Rockford, Ill.); UV sensor #1: in-line stainless steel standard flow cell C (part #79853-60000 in the Agilent 1050 variable wavelength detector #79853C). The cell has a pressure rating of 40 bar, a path length of 8 mm, and a volume of 14 μL. The built-in sensor uses Seti UVTOP TO18 LEDs at wavelengths 260 nm and 280 nm for dual wavelength light source, and Thor labs FGA71 photodiode for the detector. The board is custom-designed, utilizing a Texas Instruments MSP430F4x micro100 controller; 5 mL HiTrap™ DEAE desalting polishing column (GE Healthcare Bio-Sciences, Pittsburgh, Pa.); UV sensor #2 identical to UV sensor; polished sample collection compartment; waste; tablet computer/controller for collecting information and comprising a machine learning system (not shown)
FIG. 1D shows the microfluidic mixer of FIG. 1C showing the picture of the mixer showing placement of the inlet and outlet and the basic mixing design with mixing profile.

The Biological derived Medicines on Demand (Bio-MOD) system, as shown in FIGS. 1A, B, C and D, is designed for the production of a variety of therapeutic proteins in single or multiple small doses whenever and wherever they are needed. These point-of-care settings may range from the patient's bedside, a doctor's office, a local pharmacy, the battlefield, disaster areas, or very remote locations. The Bio-MOD device produces these proteins using in vitro translation (IVT) (8,9) (also called cell-free protein synthesis) where cell lysates are used to rapidly express proteins rather than intact living cells. The goal of the Bio-MOD technology is to combine IVT from lyophilized cell lysates with microfluidic purification methods to produce highly purified products in a few hours using an automated platform with built-in diagnostics including the use of machine learning to monitor process consistency. Essentially, this manufacturing technology can be compared to a GMP facility in a box.

The major advantages and focus of the present invention are centered on patient safety and the incorporation of in-process testing, statistical analysis, sterility/potency validation and feedback mechanism for quality assurance. As such, the present invention provides for additional detailed characterization of individual lots to demonstrate the rigor, consistency and robustness of cell-free real-time biomanufacturing. A major advance of the disclosed point-of-care manufacturing approach is the integration of on-board analytics to a cloud-based, machine-learning CMC (Computational Medicine Center) approach to provides needed governmental quality assurance.

The system is designed to have modular components to provide flexibility and compatibility, allowing for customization of the script, columns, buffers and flow rates according to the requirements of the user. The software controls the device through a conventional USB interface, where the overall power requirement is less than 90 W. The current system is a stand-alone deployable unit that can operate for up to three end-to-end cycles of protein production per day onsite. The inherent long-term stability of the lyophilized IVT components makes them ideal for on-demand and on-site protein production and freedom from a cold-chain.

The Bio-MOD 3.0 systems has five programmable syringe pumps, two UV sensors and four pressure sensors to monitor the two-step purification process, which uses an immobilized metal ion affinity chromatography (IMAC) column as a first step, and an ion-exchange (DEAE) column for the second (polishing) step. The pumps operate in the pressure range of 0.2-30 psi and dispense at a rate of 0.004 to 3.0 ml min-1. With standard biocompatible, disposable connectors and fluid flow restrictors, the bioprocess fluid train was tested to withstand up to ~30 psi during operation. An off-the-shelf, single-use 1 ml IMAC column and a 5 ml DEAE column comprise the current purification scheme. The system is designed to have modular components to provide flexibility and compatibility, allowing for customization of the script, columns, buffers and flow rates according to the requirements of the user. The software program (written in LabVIEW) consists of a user interface to select either a preloaded or a customized script, which initiates a run. A single button push initiates the entire operation from priming of the fluid train to collection of the purified protein in a sterile vial, in theory, ready for immediate administration to the patient. A dashboard is available to monitor the various sensor data in real time, which are logged into a file for data collection and post-run analysis. The software controls the device through a conventional USB interface. The overall power requirement is <90 W. The system is a stand-alone deployable unit that can operate for up to three end-to-end cycles of protein production per day onsite. Interchangeable process analytical technology (PAT) has been implemented as plug-and-play sensors for in-line absorbance, pressure and temperature sensors. With PAT, the Bio-MOD incorporates self-monitoring software through all phases of the Bio-MOD set-up and purification, making the device simple and user friendly even for non-experts.

For set-up and priming of the fluid train, the user commences a simple auto-priming procedure where the Bio-MOD monitors the flow path confirming that the priming is performed properly and free of bubbles. Depending on the desired purification process, three to four interactive check points (depending on choice of purification scheme) make the user aware of any problems with leaks or bubbles in the priming of the fluid train, and aid in identifying a quick fix such as increasing the priming cycle to flush the system. All purification system parameters such as buffer conditions, column residence times and flow rates were initially optimized using a standard Dionex Ultimate 3000 HPLC system (Thermo Fisher Scientific, Bannockburn, Ill.). These parameters were then translated to the automated Bio-MOD system.

Cell-free protein (IVT) synthesis offers a major paradigm shift for the production of biopharmaceuticals. Traditional biotechnology employs millions of miniscule bioreactors, the cells, distributed sparsely throughout the macroscopic bioreactor, typically at 5-10% of the total volume. Biosynthetic components are condensed at high concentrations within these individual chambers. With cell-free approaches, these catalytic components become distributed evenly throughout the entire reactor volume, but typically at 5-10% of intracellular concentrations. Although the resultant biopharmaceutical volumetric productivities are similar, tremendous advantages are gained because now all metabolic resources can be focused on producing a single protein, instead of at least several hundred, and importantly access to the actual reaction chamber.

Protein folding is more effective because only a single protein is being produced and because the folding environment can be customized specifically for that product. Further, because the ribosomes are spaced farther apart, the risk that the emerging polypeptides will inappropriately interact is reduced. Because translational elongation factors are diluted, polypeptides also emerge more slowly from the ribosomes so that co-translational folding pathways are encouraged. Finally, direct access to the translation and folding environment allows optimization of foldase and chaperones concentrations as well as adjustment of solution properties such as the ionic strength and —SH/S—S redox potential. For example, the production of proteins that are poorly soluble or suffer from a hydrophobically-mediated kinetic trap in their folding pathway can be accumulated to much higher concentrations using lower ionic strength reaction mixtures. Also, proteins with multiple disulfide bonds can often be folded more effectively by optimizing the —SH/S—S redox potential and protein disulfide concentration. Finally, folding is often improved by customizing the chaperones type and concentration. Most of these measures are not possible at all or are difficult to implement with cell-based production.

In recent studies, expression of proteins using freeze-dried cell-free extracts has been described for portable production of peptides and vaccines (10, 11), as well as the conversion of digital sequences to nucleotide sequences using an automated DNA synthesizer and liquid handling system (12). The present invention exceeds these efforts of rapid protein expression with the incorporation of highly effective protein purification into a portable system, as well as onboard quality control through the use of machine learning. The result is the manufacture of a pure and potent biologic ready to be dispensed at the point-of-care. In addition, the DNA synthesizer described in (12) can be plugged into the Bio-MOD system for protein manufacturing starting with digital sequences.

Figure 1B:
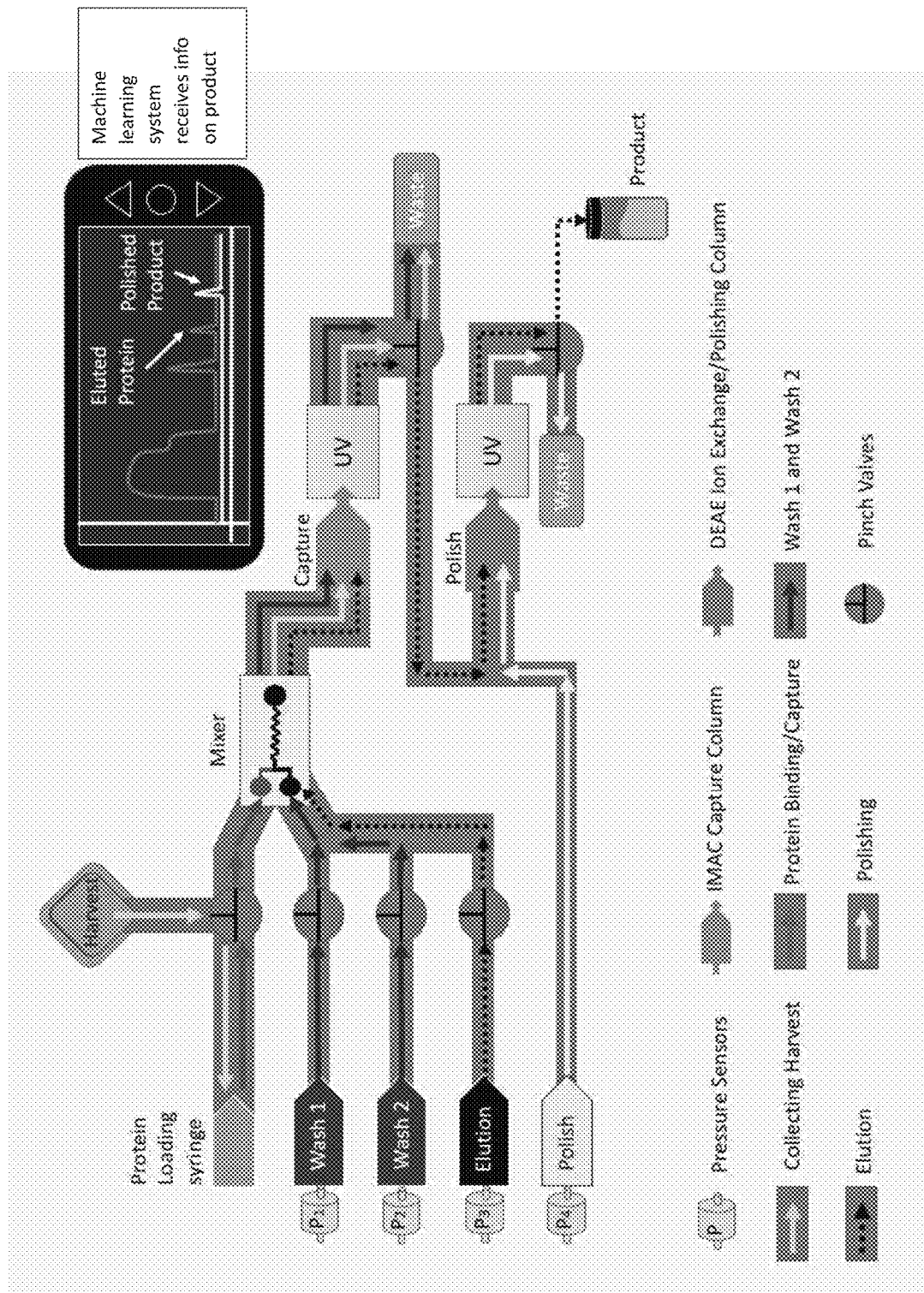
Figure 1C:
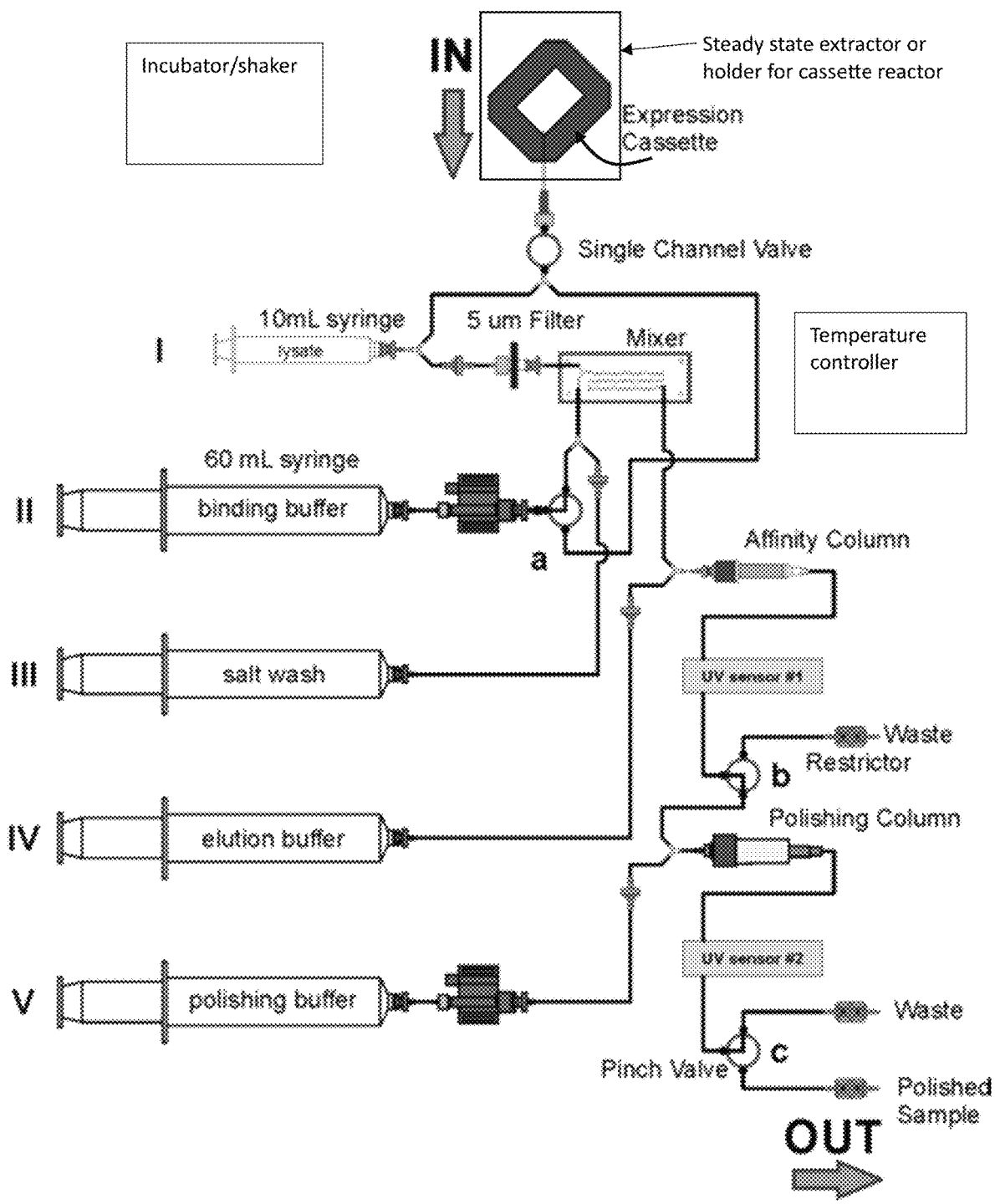
Figure 1D:
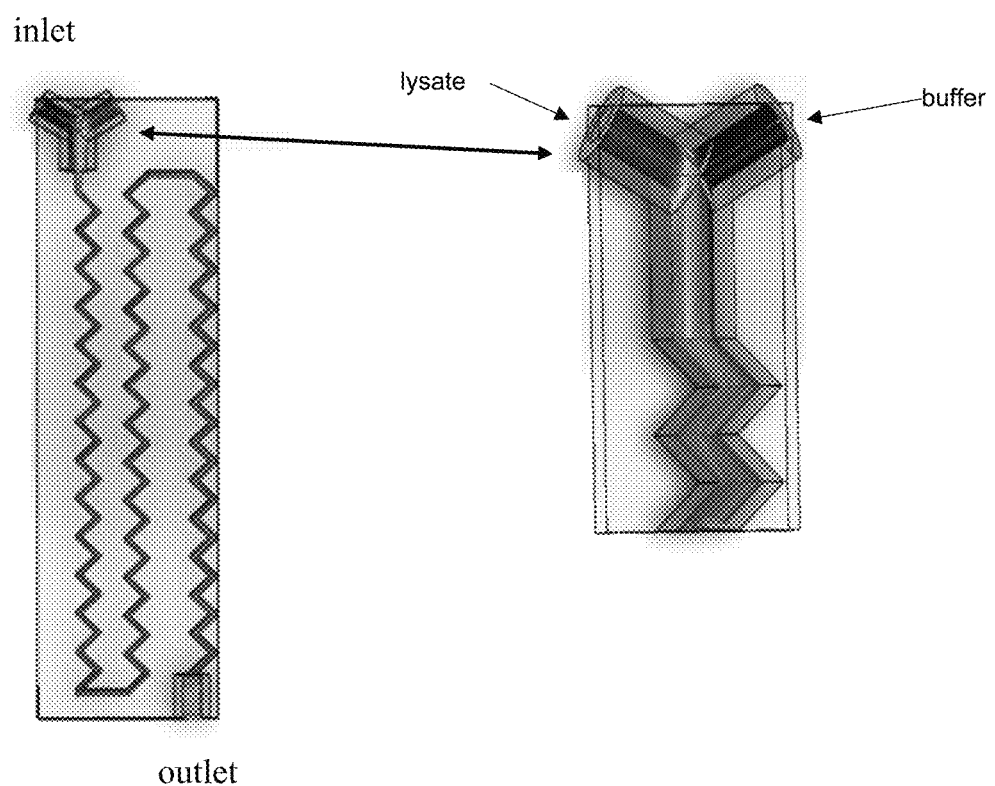

The Bio-MOD platform shown in FIGS. 1A, 1B and 1C has two modules: the protein expression module and the protein purification module, each with associated analytics. The hardware is designed in two parts with fixed hardware (pumps, sensor, tablet computer) and a single-use bioprocess train (reactor, syringes, tubing, microfluidic mixers, capture and polishing columns). The system is fully automated with built-in software and programmable syringe pumps with pressure sensors for the delivery of lysate and buffers. Protein expression is currently carried out in dialysis cassettes. Once loaded with the IVT reaction, which is composed of the cell lysate, reaction mix and cDNA for the target protein, the cassette is immersed in dialysis buffer inside a sealed bag, hereafter called the "reactor."

A quick review of protein synthesis is provided herein where a protein is expressed in three main steps: replication, transcription and translation. DNA multiplies to make multiple copies by a process called replication. Transcription occurs when the double-stranded DNA is unwound to allow the binding of RNA polymerase producing messenger RNA (mRNA). Transcription is regulated at various levels by activators and repressors, and also by chromatin structure in eukaryotes. In prokaryotes, no special post-transcriptional modification of mRNA is required. However, in eukaryotes, mRNA is further processed to remove introns (splicing), to add a 'cap' (M7 methyl-guanosine) at the 5' end and to add multiple adenosine ribonucleotides at the 3' end of mRNA to generate a poly(A) tail. The modified mRNA is then translated.

The translation or protein synthesis is also a multi-step process with Initiation, Elongation and Termination steps and is similar in both prokaryotes and eukaryotes. The difference is that in eukaryotes, proteins may undergo post-translational modifications, such as phosphorylation or glycosylation. The translation process requires cellular components such as ribosomes, transfer RNAs (tRNA), mRNA and protein factors as well as small molecules like amino acids, ATP, GTP and other cofactors.

The difference between in vivo and in vitro (cell-free) protein expression is that in cell-free expression, the cell wall and the nuclei are no longer present. To obtain the cell extract for cell-free protein expression, cells (E. coli, wheat germ, mammalian cells) are subjected to cell lysis followed by separation of the cell wall and nuclear DNA. The desired protein is synthesized by adding a DNA or mRNA template into the cell extract together with a reaction mix comprising of biological extracts and/or defined reagents. The reaction mix is comprised of amino acids, nucleotides, co-factors, enzymes and other reagents that are necessary for the synthesis, e.g. ribosomes, tRNA, polymerases, transcriptional factors, etc. When DNA is used as template (i.e. linked reaction), it is first transcribed to mRNA. Alternatively, mRNA could also be used directly for translation.

The template for cell-free protein synthesis can be either mRNA or DNA. Translation of stabilized mRNA or combined transcription and translation converts stored information into a desired protein. The combined system, generally utilized in E. coli systems, continuously generates mRNA from a DNA template with a recognizable promoter. Either endogenous RNA polymerase is used, or an exogenous phage RNA polymerase, typically T7 or SP6, is added directly to the reaction mixture. Alternatively, mRNA can be continually amplified by inserting the message into a template for QB replicase, an RNA dependent RNA polymerase. Purified mRNA is generally stabilized by chemical modification before it is added to the reaction mixture. Nucleases can be removed from extracts to help stabilize mRNA levels. The template can encode for any particular gene of interest.

Salts, particularly those that are biologically relevant, such as manganese, potassium or ammonium, may also be added. The pH of the reaction is generally run between pH 6-9. The temperature of the reaction is generally between 20° C. and 40° C. These ranges may be extended.

In addition to the above components such as cell-free extract, genetic template, and amino acids, other materials specifically required for protein synthesis may be added to the reaction. These materials may include salts, polymeric compounds, cyclic AMP, inhibitors for protein or nucleic acid degrading enzymes, inhibitors or regulators of protein synthesis, oxidation/reduction adjusters, non-denaturing surfactants, buffer components, spermine, spermidine, etc.

The salts preferably include potassium, magnesium, ammonium and manganese salts of acetic acid or sulfuric acid, and some of these may have amino acids as a counter anion. The polymeric compounds may be polyethylene glycol, dextran, diethyl aminoethyl dextran, quaternary aminoethyl and aminoethyl dextran, etc. The oxidation/reduction adjuster may be dithiothreitol (DTT), ascorbic acid, glutathione and/or their oxides. Further DTT may be used as a stabilizer to stabilize enzymes and other proteins, especially if some enzymes and proteins possess free sulfhydryl groups. Also, a non-denaturing surfactant such as Triton X-100 may be used at a concentration of 0-0.5 M. Spermine and spermidine may be used for improving protein synthetic ability, and cAMP may be used as a gene expression regulator.

The current onboard protein expression module is equipped with a Peltier heating source, temperature sensor, and muffle-fan for a uniform and continuous distribution of heat. Both the temperature and shaking speed are programmable via LabVIEW software program using a computer tablet. The protein purification module has two built-in flow cells, each equipped with a UV sensor for monitoring the 2-step purification process involving affinity chromatography and ion-exchange chromatography for polishing. In addition, four pressure sensors are incorporated behind each syringe pump plunger for continuous system pressure monitoring. These along with system temperature form the current process analytical technologies (PAT) sensors that are already proving their value in demonstrating process consistency.

FIG. 1C shows the Bio-Mod system has five programmable syringe pumps, two UV sensors and four pressure sensors to monitor the two-step purification process, which uses an immobilized metal ion affinity chromatography (IMAC) column as a first step, and an ion-exchange (DEAE) column for the second (polishing) step. A dedicated miniaturized shaker that is closer in speed to the standard benchtop is used for integration into the system. The pumps operate in the pressure range of 0.2-30 psi and dispense at a rate of 0.004 to 3.0 ml min-1. With standard biocompatible, disposable connectors and fluid flow restrictors, the bioprocess fluid train was tested to withstand up to ~30 psi during operation. An off-the-shelf, single-use 1 ml IMAC column and a 5 ml DEAE column comprise the purification scheme. The system is designed to have modular components to provide flexibility and compatibility, allowing for customization of the script, columns, buffers and flow rates according to the requirements of the user. The software program (written in LabVIEW) consists of a user interface to select either a preloaded or a customized script, which initiates a run. A single button push initiates the entire operation from priming of the fluid train to collection of the purified protein in a sterile vial, in theory, ready for immediate administration to the patient. A dashboard is available to monitor the various sensor data in real time, which are logged into a file for data collection and post-run analysis. The software controls the device through a conventional USB interface. The overall power requirement is <90 W. The Bio-MOD system is a stand-alone deployable unit that can operate for up to three end-to-end cycles of protein production per day onsite. Interchangeable process analytical technology (PAT) has been implemented as plug-and-play sensors for in-line absorbance, pressure and temperature sensors. With PAT, the Bio-MOD incorporates self-monitoring software through all phases of the Bio-MOD set-up and purification, making the device simple and user friendly even for non-experts. For set-up and priming of the fluid train, the user commences a simple auto-priming procedure where the Bio-MOD monitors the flow path confirming that the priming is performed properly and free of bubbles. Depending on the desired purification process, three to four interactive check points (depending on choice of purification scheme) make the user aware of any problems with leaks or bubbles in the priming of the fluid train, and aid in identifying a quick fix such as increasing the priming cycle to flush the system.

All purification system parameters such as buffer conditions, column residence times and flow rates were initially optimized using a standard Dionex Ultimate 3000 HPLC system (Thermo Fisher Scientific, Bannockburn, Ill.). These parameters were then translated to the automated Bio-MOD system.

Figure 5:
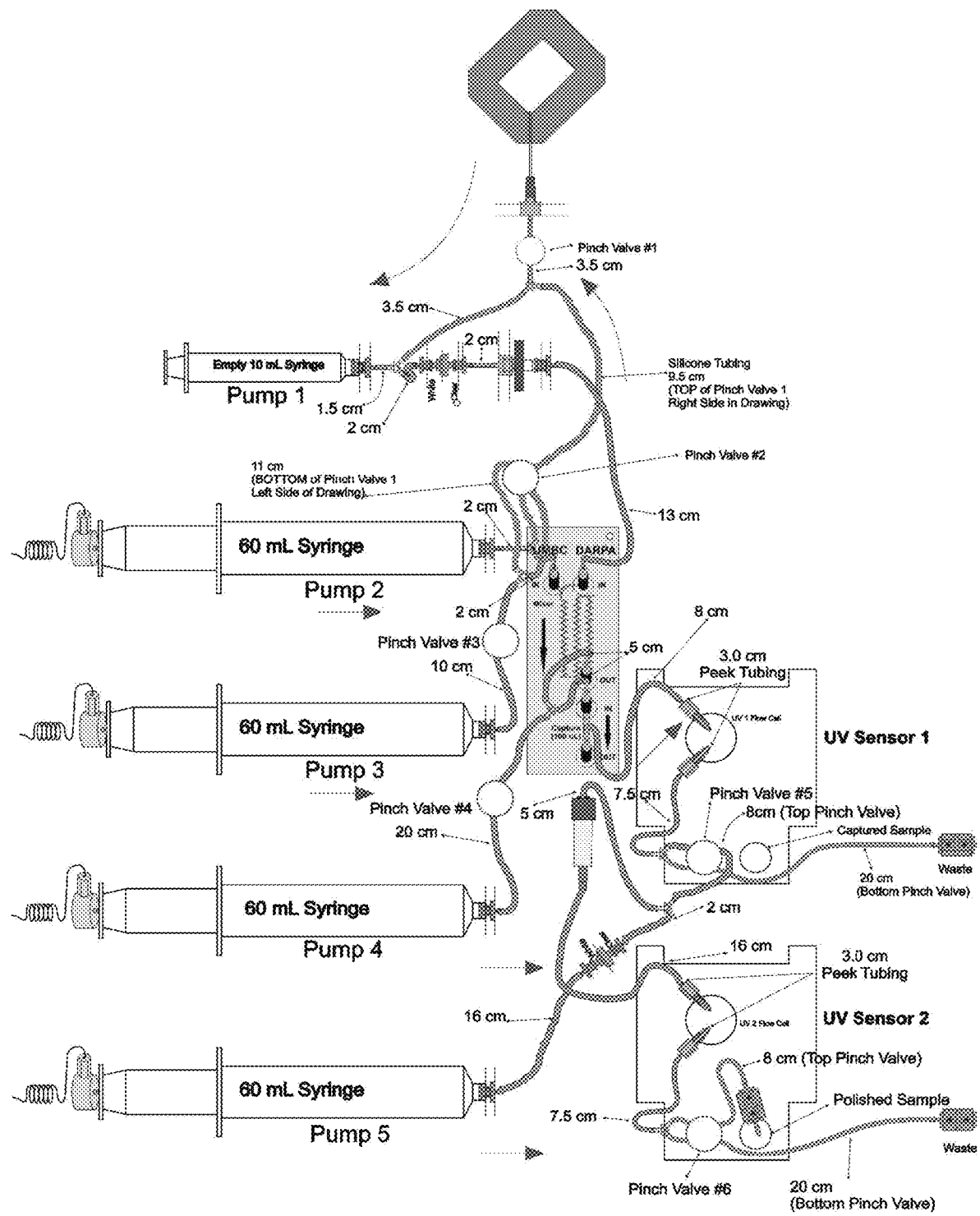
FIG. 5A shows the components and process schematic of the single-use parts in the current Bio-MOD. All materials in contact with the process have been validated for leachables and extractables.
FIG. 5B provides and explanation of each component.
FIG. 5C shows how the process train can be modified to operate as a continuous production platform, thereby allowing continuous manufacturing to be operationalized.
Figure 5:
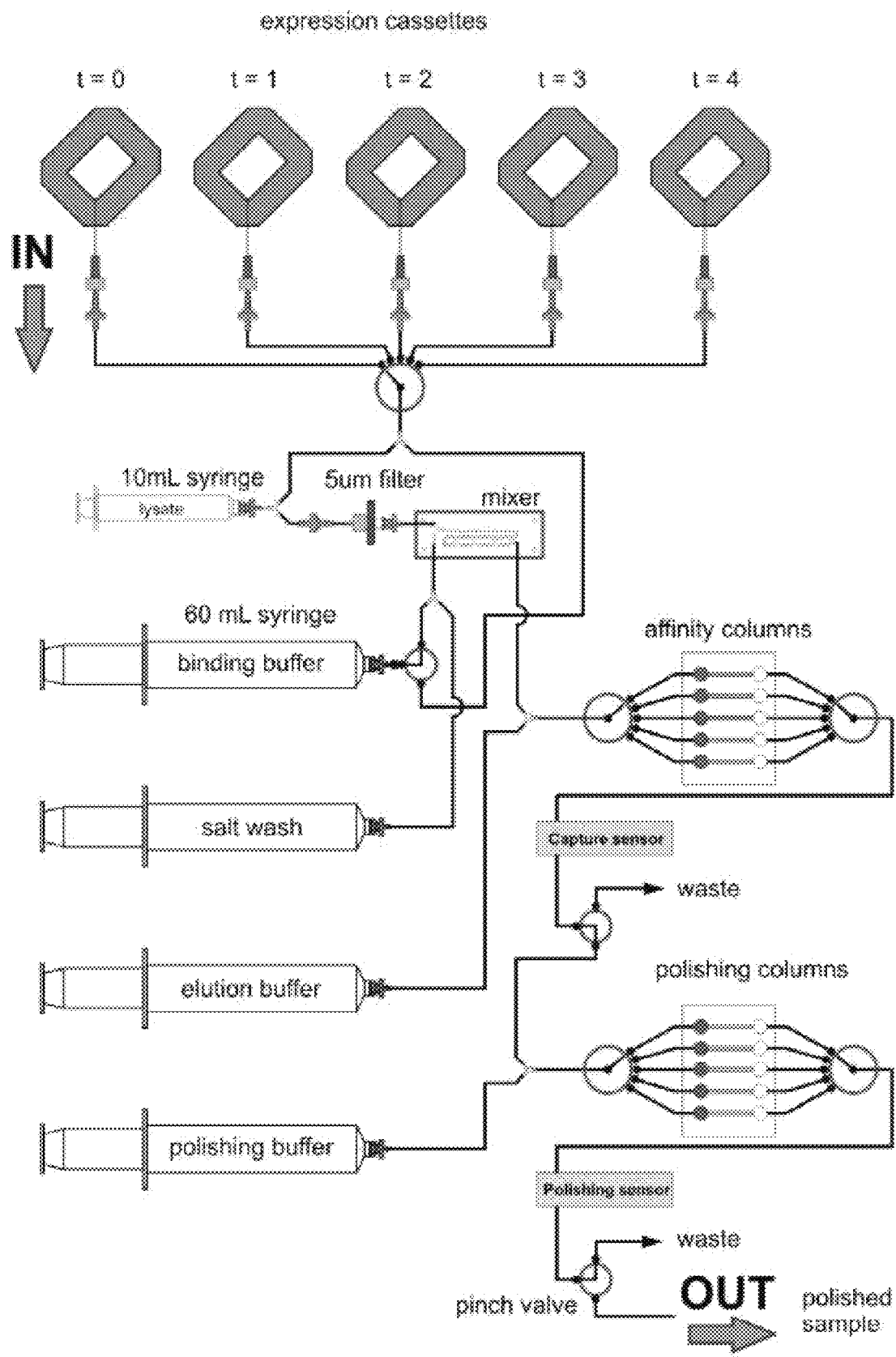

The components and process schematic of the single-use parts in the current Bio-MOD are clearly defined in FIG. 5A. FIG. 5B provides clarification on all respective parts. Cost of disposable train <$500. FIG. 5C shows how the process train can be modified to operate as a continuous production platform, thereby allowing continuous manufacturing to be operationalized.

Such Bio-MOD system has been thoroughly validated and demonstrated for proof of operation with several proteins (7) and as discussed below. Importantly, all materials in contact with the process have been validated for leachables and extractables.

Maximizing yields from the expression system is important and currently, most cell-free expression is carried out in batch mode, but continuous cell-free expression is also possible. Improvements to achieve the highest possible yields and purification recoveries of >70% overall of the final product can be accomplished by rocking the chamber to improve mixing and mass transfer (4). Notably, critical process parameters (pH, DO, temperature) are considered to be important for monitoring during the expression and thereby adding another layer of robustness during the process monitoring. For example, use of a dialysis cassette with integrated sensors as part of the expression module. Further, optimization of the Bio-MOD can be achieved by co-expression of chaperones, addition of amino acids, energy substrates etc, as recently described in (4,5,7,13).

The automated production of the proteins in the Bio-MOD system was implemented for the protein expression of G-CSF (typically 2.0 ml) and several other proteins described later herein were executed in a 10 or 20 kDa MWCO dialysis cassette and incubated in a Sartorius incubator at 30° C. and 150 r.p.m. for 6 h. The cassette containing the harvest was removed from the incubator and placed in the purification module, Pump I was programmed to withdraw 2.1 ml from the dialysis cassette to ensure all of the 2.0 ml harvest is collected. The harvest was passed through a 5 μm filter to remove protein aggregates before reaching the in-house-developed microfluidic mixer (FIG. 1C), where the harvest was mixed with the loading/binding buffer. By simultaneously operating both pump I and pump II at 0.2 ml min$^{-1}$ pushing fluids towards the microfluidic mixer, the harvest was diluted five times with binding buffer in a continuous manner. A unidirectional check valve was employed to prevent backflow of the harvest or the binding buffer from the flush lines. To maximize product recovery, the filter and fluidics were rinsed with 1 ml binding buffer. The diluted harvest was loaded onto a pre-saturated 1 ml HisPur Cobalt column at a rate of 0.2 ml min$^{-1}$ to maximize product capture. After that, the column was washed with 1×PBS by operating pump II. A second wash with a high salt concentration using pump III removed a significant portion of impurities in the affinity column due to non-specific binding. The product was eluted from the column by switching to pump IV, which dispensed the elution buffer. The entire purification process was monitored in real time by measuring the UV absorbance at 280 nm. This was achieved by positioning a standard HPLC flow cell fitted with a custom-made UV sensor after the affinity column. The sensor is comprised of an LED as a UV light source and a photodiode to detect the transmitted light, along with custom circuit boards to control these components. The UV sensor is integrated with the software module allowing feedback-based control of other components such as the two-channel pinch valves.

Figure 11:
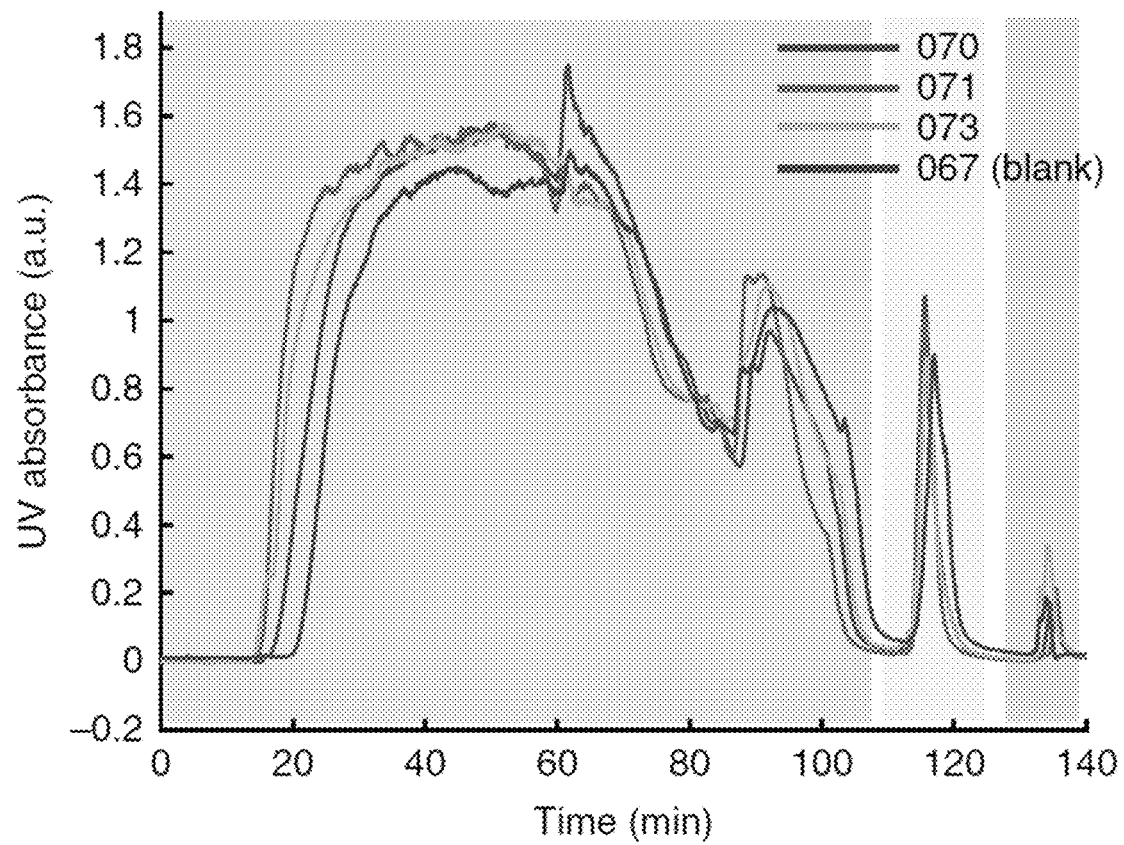
FIG. 11A shows G-CSF-His produced in the Bio-MOD, wherein the UV1 traces shows the first stage (affinity column) purification. Shaded areas correspond to the different stages: column loading (green), salt wash (blue) and product elution (pink)
FIG. 11B shows UV2 traces showing the second stage (polishing column) purification. Shaded area corresponds to the product collection window (for runs 070, 071 and 073; 067 is the blank)
FIG. 11C shows the corresponding silver-stained SDS-PAGE.
FIG. 11D shows Western blot using anti-G-CSF antibody. The higher molecular weight band is due to aggregation after storing the samples for several days at neutral pH.
FIG. 11E shows the bioactivity of G-CSF-His runs 070, 071 and 073 along with blank run 067. Negative control samples were inactivated by boiling at 100° C. for 10 min. The measures of centre and error bars represent the means and s.e.m. for n=3.
Figure 11:
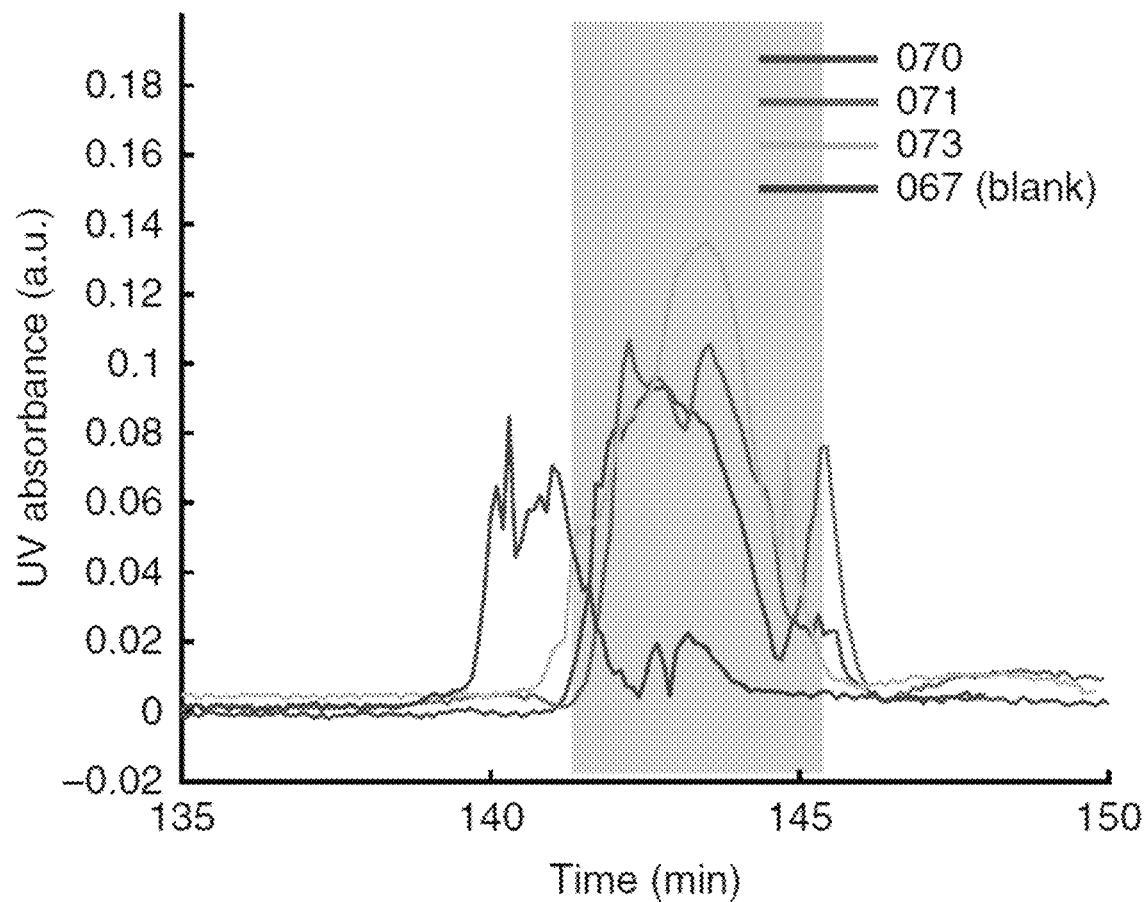
Figure 11:
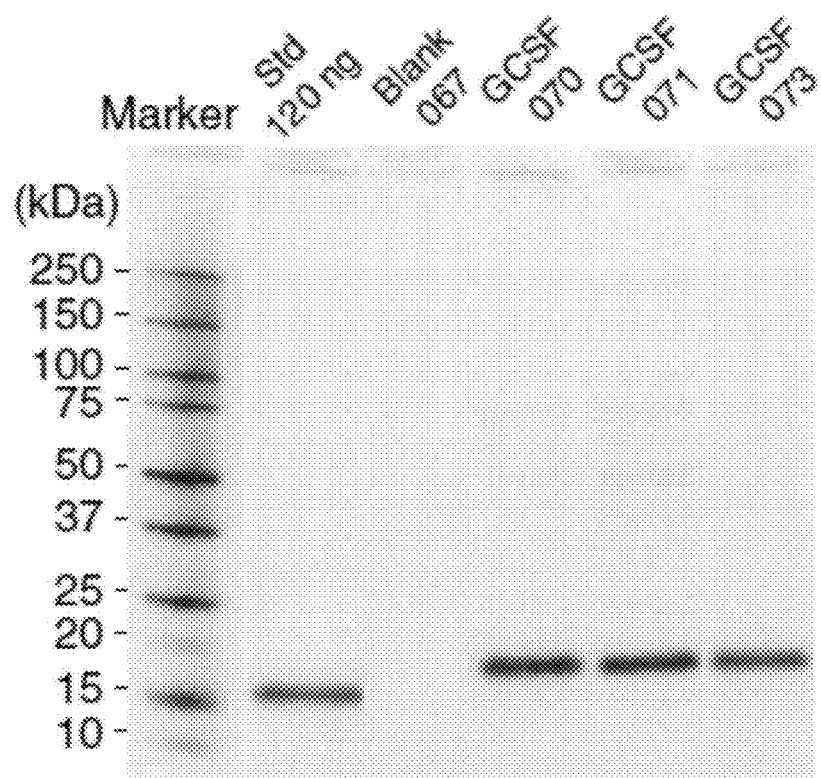
Figure 11:
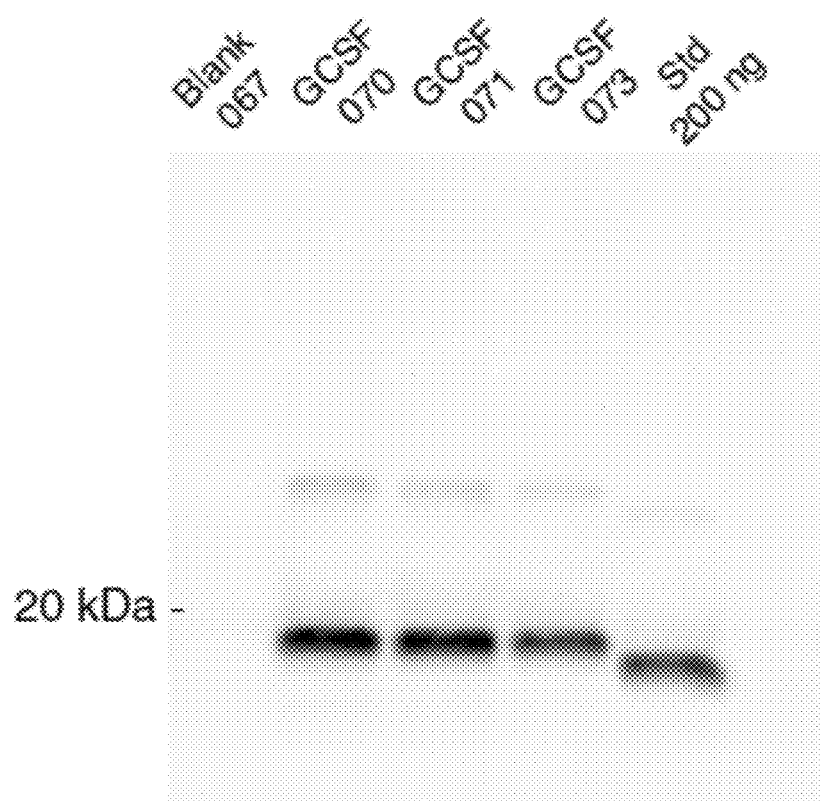
Figure 11:
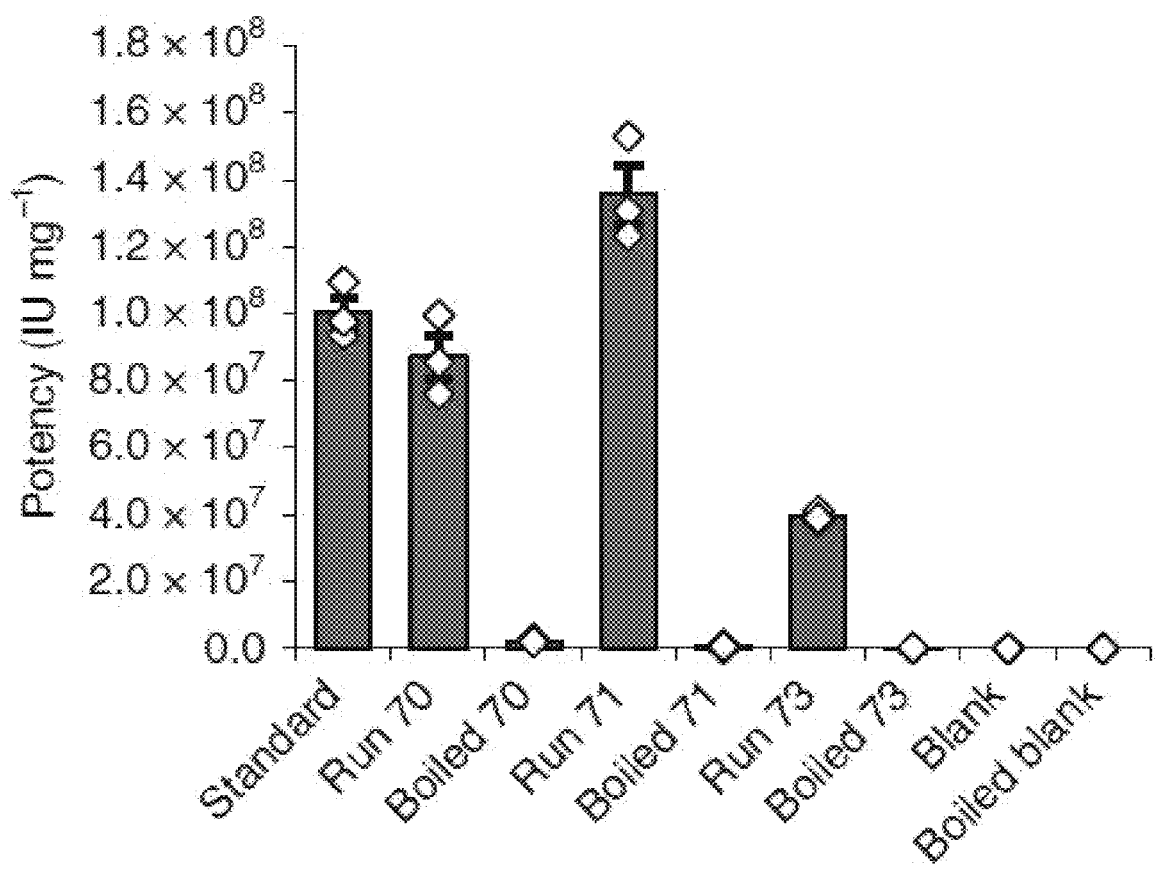

The process algorithm detects the change in slope of the UV trace during elution of the product. With the addition of a polishing step, the elution peak from the affinity column was automatically directed to a pre-saturated 5 ml HiTrap DEAE fast flow column (GE cat. no. GE17-5154-01). Pump V dispenses the polishing buffer (20 mM phosphate buffer with 50 mM arginine) at 1 ml min$^{-1}$ through the ion-exchange column. G-CSF-His is not retained in the DEAE column (product is present in the void volume). Thus, the start and end points of product collection were automatically calculated based on the post-UV flow cell volume, tube length and flow rate, ensuring precise control of the pinch valve. Finally, the polished product was collected in a vial for further off-line analysis. Three independent runs (runs 070, 071 and 073) to produce G-CSF-His were done with a corresponding negative control (run 067). The entire time needed for the end-to-end production run including protein expression and purification was about 8.5 h. Traces from UV sensor 1 (FIG. 11A, affinity column) and UV sensor 2 (FIG. 11B, polishing column) of G-CSF-His produced in the Bio-MOD have very similar profiles.

The quality and activity of the G-CSF-His was characterized offline. Purity was found to be approximately ~98% as determined by high sensitivity silver stained SDS-PAGE (FIG. 11C and Table 1), with a clear improvement in results due to polishing. This level of purity conforms to that typically expected by regulatory agencies for investigational trials of parenteral biologics (https://go.nature.com/21zJyYD). Increased purity beyond this level can be achieved by incorporating additional polishing steps using strategies similar to those employed for biologics produced in cell-based expression systems. Additionally, the high-sensitivity silver-stained SDS-PAGE showed consistent purity and concentration at the end of the ion-exchange purification for G-CSF-His (runs 070, 071 and 073). An average yield of ~110 µg was calculated based on the integrated signal density of the protein bands in the silver stains. These values were used in the determination of activities in FIG. 11E and Table 1 (shown below).

The identity of the IVT-expressed G-CSF samples was confirmed by western blot analysis using anti-G-CSF antibody showing a product band at ~19 kDa which is slightly higher than the native (standard) G-CSF band at ~17 kDa. This was expected due to the presence of the 6×His tag and the additional amino acids from the IVT vector ('M-A-T-T-H' at the N-terminal and 'L-E' preceding the His-tag sequence). The activity of the Bio-MOD derived human G-CSF-His was queried using a standard cell proliferation bioassay, with the results showing that the activity of the Bio-MOD-produced G-CSF-His is at an order of magnitude higher than the single-step purified G-CSF-His. The activity of polished G-CSF-His produced using the Bio-MOD system (FIG. 11E and Table 1) is on par with that of the originator molecule, Amgen's Neupogen and the biosimilar Zarxio from Sandoz, which have specific activities of $1.0 \pm 0.6 \times 10^8$ IU mg-1 (or 0.4 to $1.6 \times 10^8$ IU mg-1) (https://go.nature.com/2KlCRr6). Table 1 summarizes the yield, purity and activity of polished G-CSF-His purified in the Bio-MOD system.

TABLE 1

Yield, purity and activity of polished G-CSF-His in the Bio-MOD

| Run no. | Yeild (µg) | | | Purity (%) | Actvity (IU mg$^{-1}$) |
|---|---|---|---|---|---|
| | Silver-stained SDS | CE-SDS | ELISA | | |
| 070 | 130 + 17 | 123 + 19 | 156 + 9 | 98.0 | $0.69 \pm 0.06 \times 10^8$ |
| 071 | 96 + 14 | 105 + 35 | 104 + 7 | 98.5 | $1.10 \pm 0.04 \times 10^8$ |
| 073 | 108 + 16 | 77 + 12 | 105 + 11 | 97.1 | $0.42 \pm 0.03 \times 10^8$ |

Average activity of reference standard (WHO, NIBSC cat. no. 09/136) = $(1.0 \pm 0.06) \times 10^8$ IU mg$^{-1}$. The measures of centre and errors represent the mean and s.e.m. of triplicate measurements.

Figure 2A:
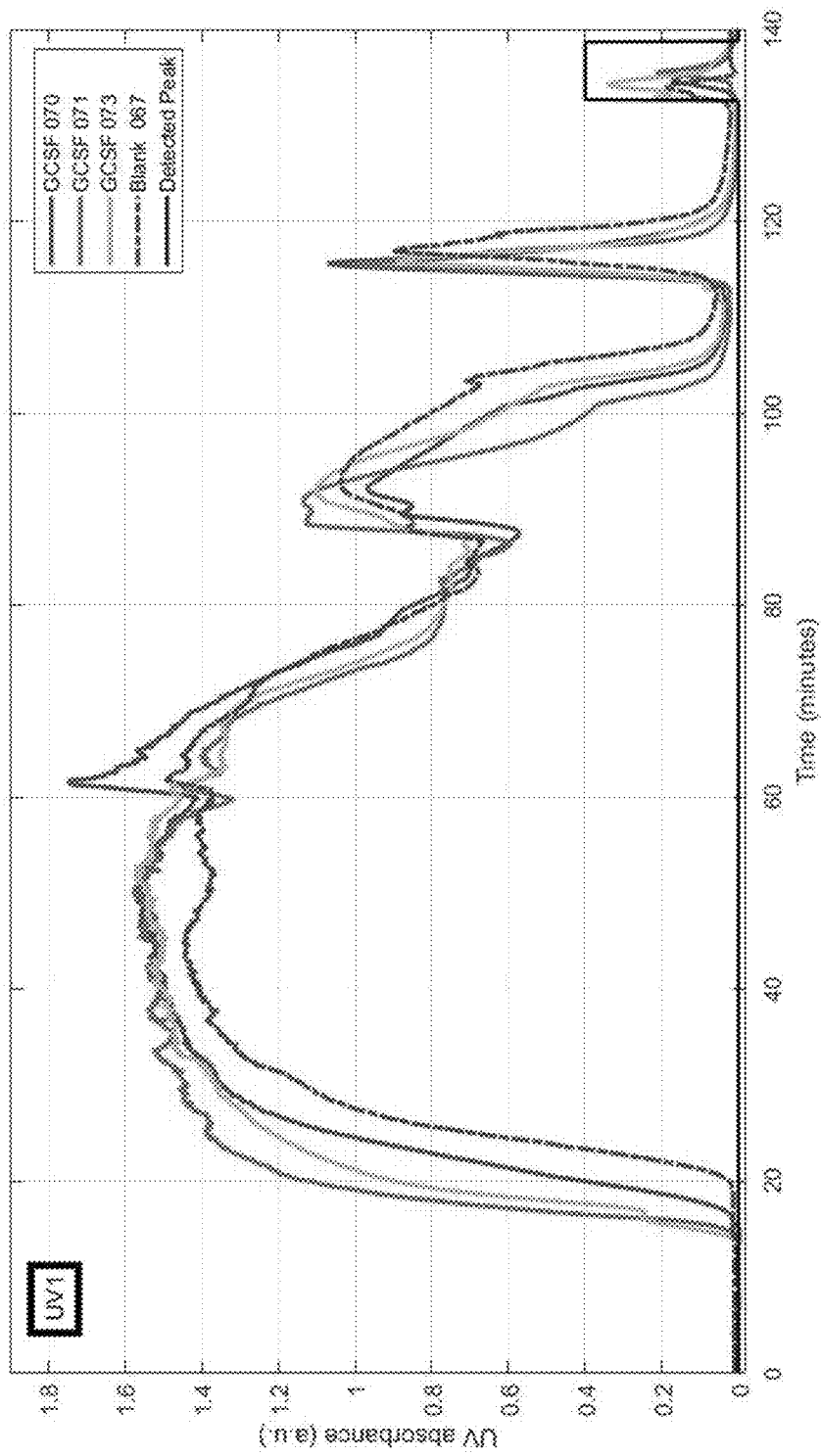
FIGS. 2A, B and C show GCSF-His produced in the Bio-MOD.
Figure 2B:
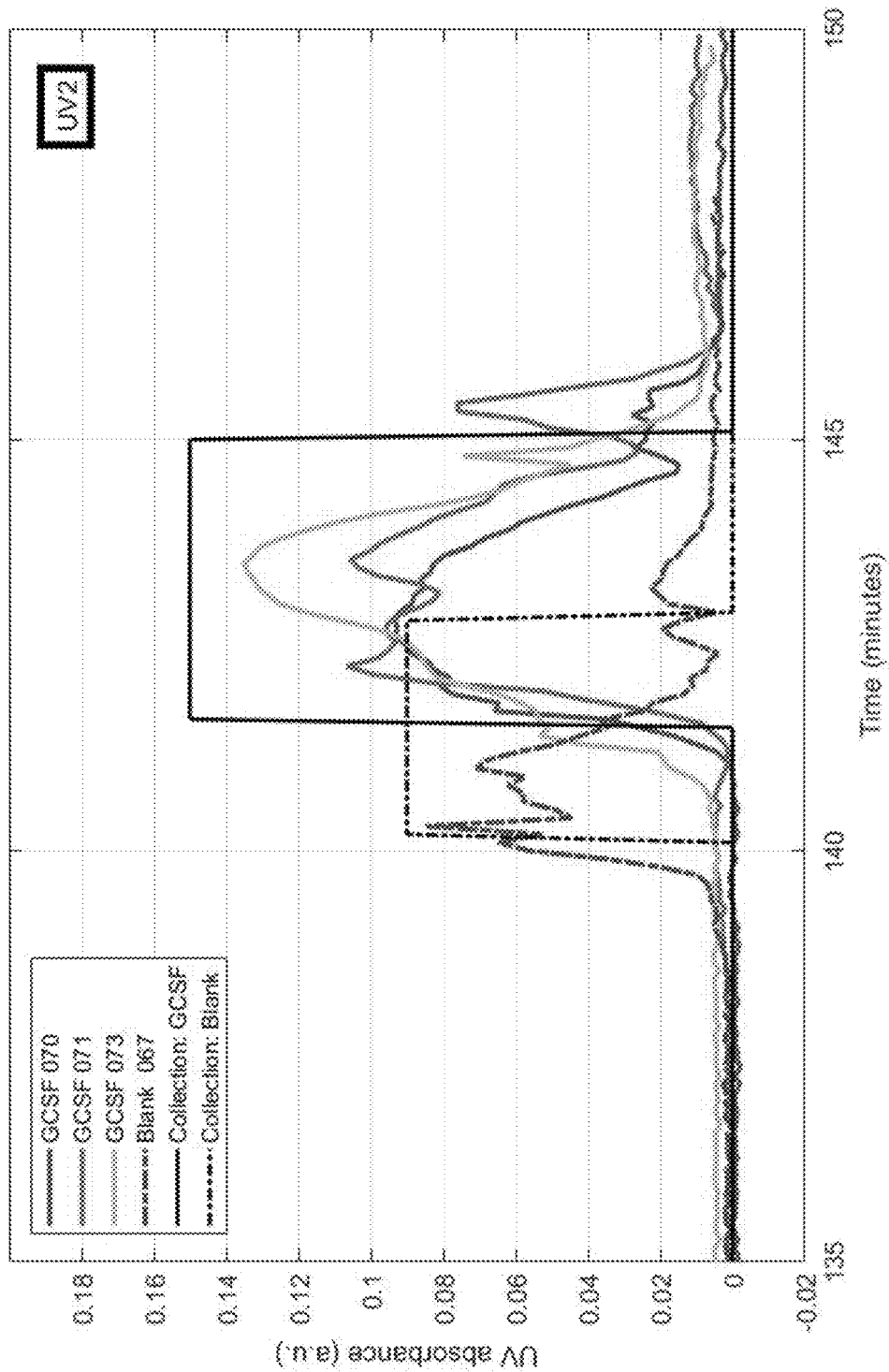
FIG. 2B shows UV2 traces showing the second stage (polishing column) purification. Box corresponds to the product collection window for runs 070, 071, and 073, dashed box run 067 is the blank)
Figure 2C:
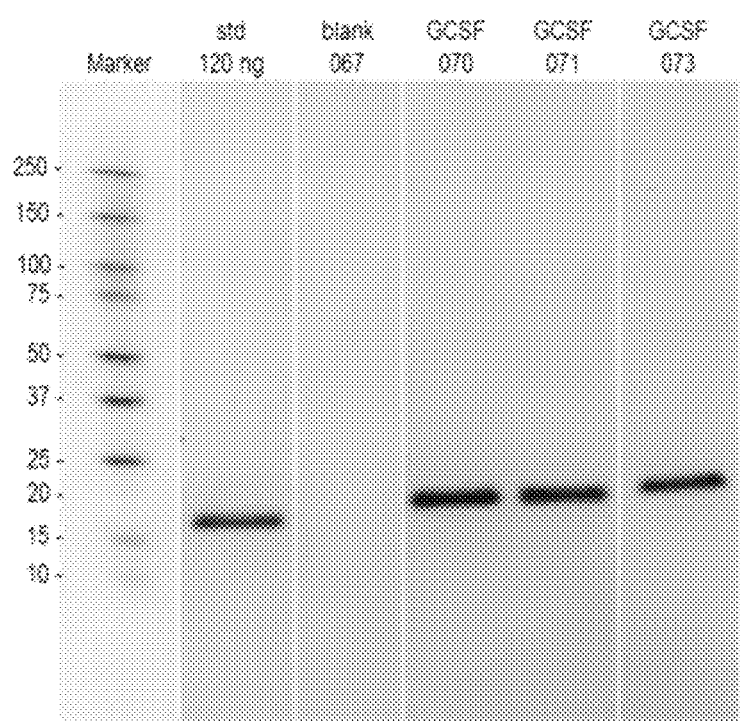
FIG. 2C shows corresponding silver stained SDS-PAGE. Average purity was 98%. The activity obtained was $0.74 \pm 0.04 \times 10^8$ IU/mg, which is in the range of Neupogen's label activity of $1.0 \pm 0.6 \times 10^8$ IU/mg (or 0.4 to $1.6 \times 10^8$ IU/mg).

G-CSF was chosen to work with for the following reasons: i) it is an approved therapeutic with several variations on the market; ii) Extensive literature data are available (18-21); iii) it is FDA-approved for mitigation of radiation exposure using the animal rule; and iv) significant preliminary data is available on its manufacture in the Bio-MOD system (7). As shown in FIG. 2, G-CSF was produced with acceptable purity and potency with the present Bio-MOD system and was shown that 770 ug of pure G-CSF was made (adult dose of Neupogen is 300 ug). Specifically FIG. 2 shows (A) UV1 traces showing the first stage (affinity column) purification and (B) UV2 traces showing the second stage (polishing column) purification. Box corresponds to the product collection window for runs 070, 071 and 073, dashed box run 067 is the blank). (C) Corresponding silver stained SDS-PAGE. Average purity was 98%. The activity obtained was $0.74 \pm 0.04 \times 10^8$ IU/mg, which is in the range of Neupogen's label activity of $1.0 \pm 0.6 \times 10^8$ IU/mg (or 0.4 to $1.6 \times 10^8$ IU/mg).

Figure 3:
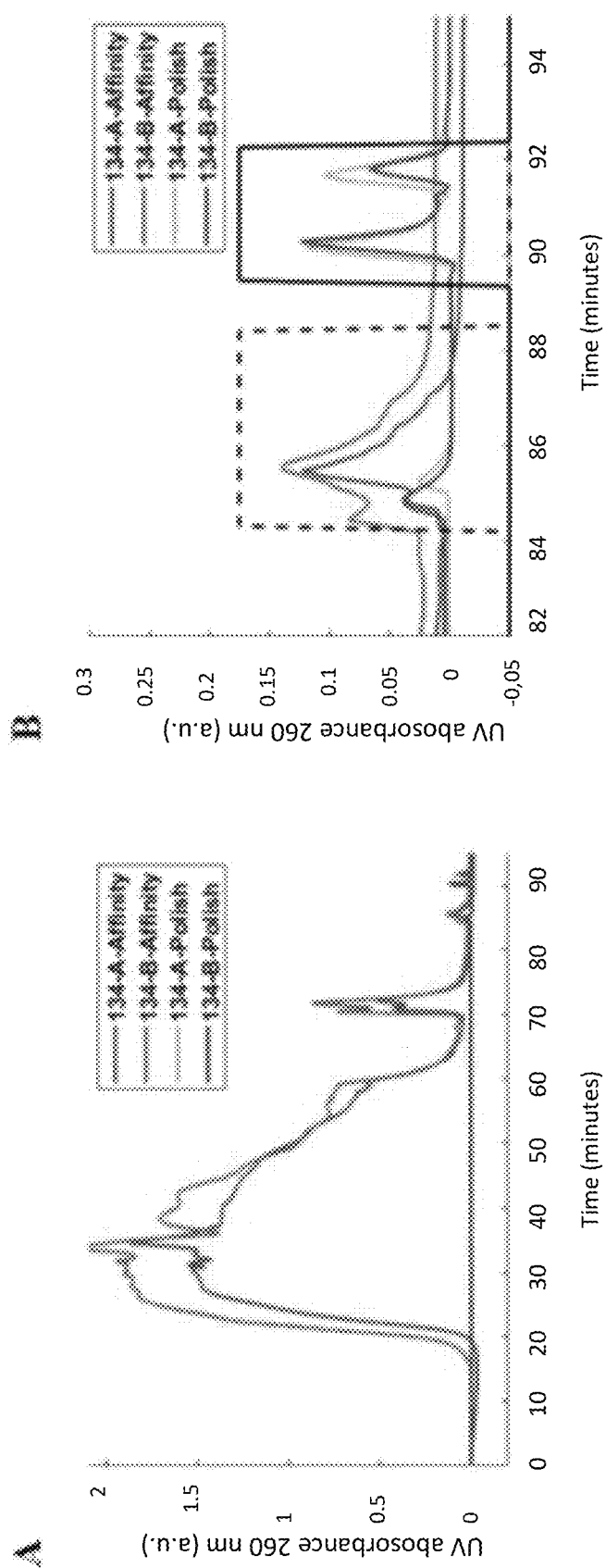
FIG. 3 shows comparison of GCSF-His produced in two identical Bio-MODs. (A) shows UV traces from purification runs on two identical Bio-MOD devices; (B) shows a magnified view of the detected affinity (dashed line window) and polishing (solid line window) elution peaks; 100 polishing fractions were collected from within the detected polishing collection window.
Figure 3:
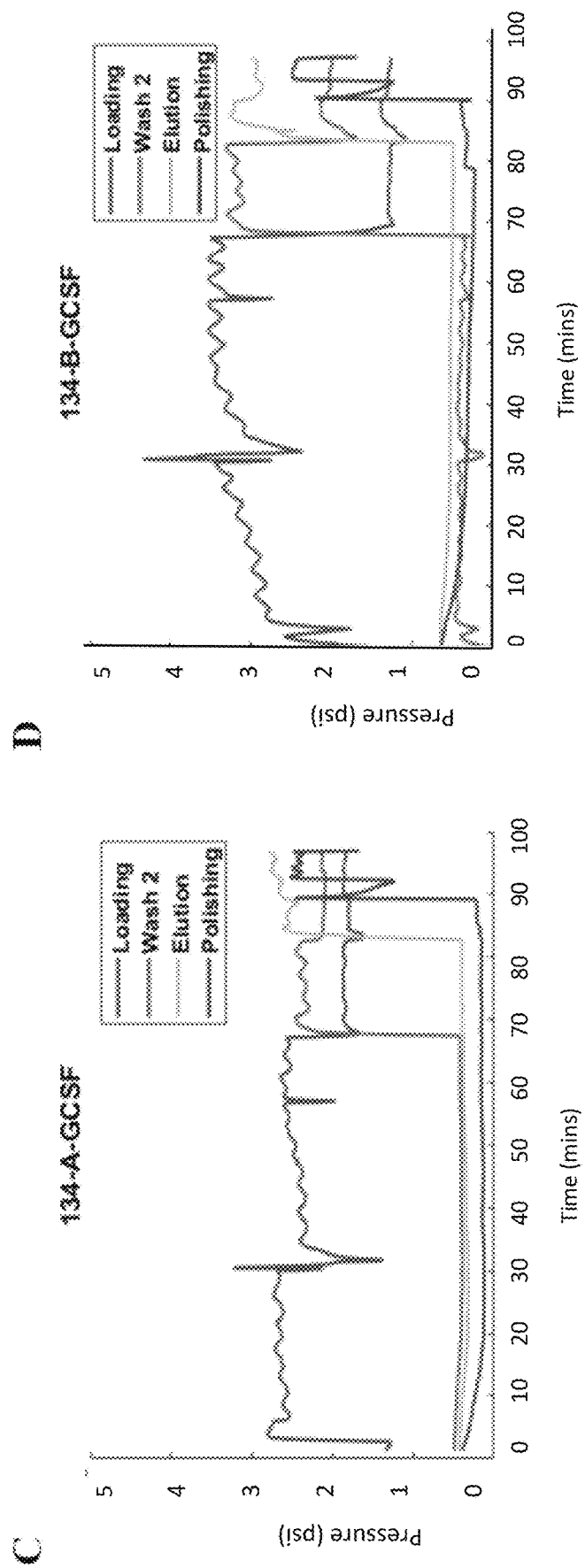
Figure 3:
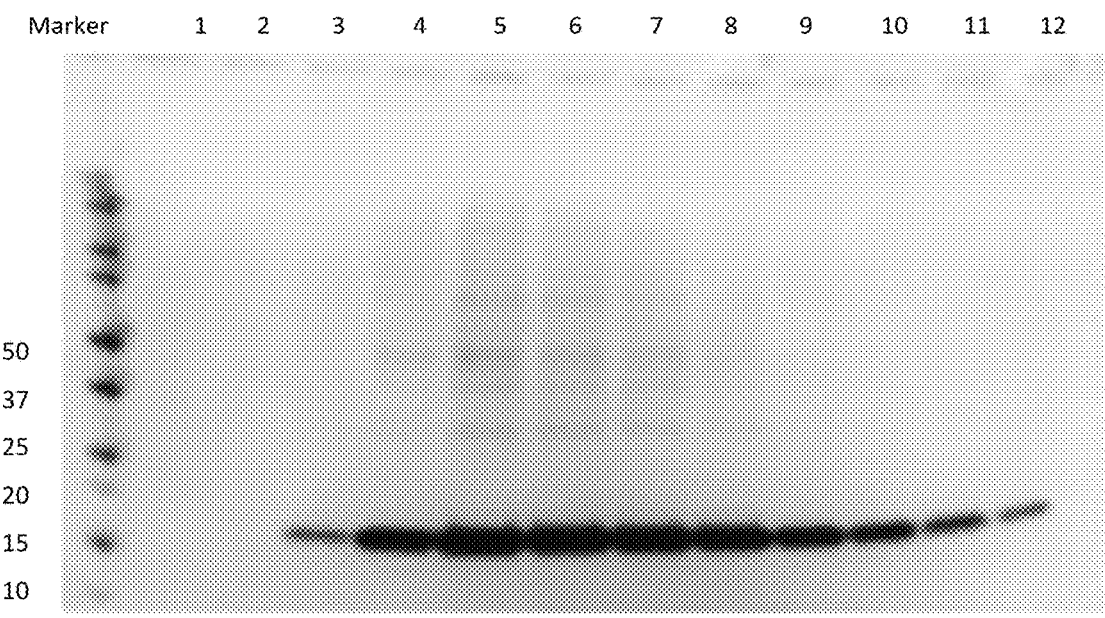
Figure 3:
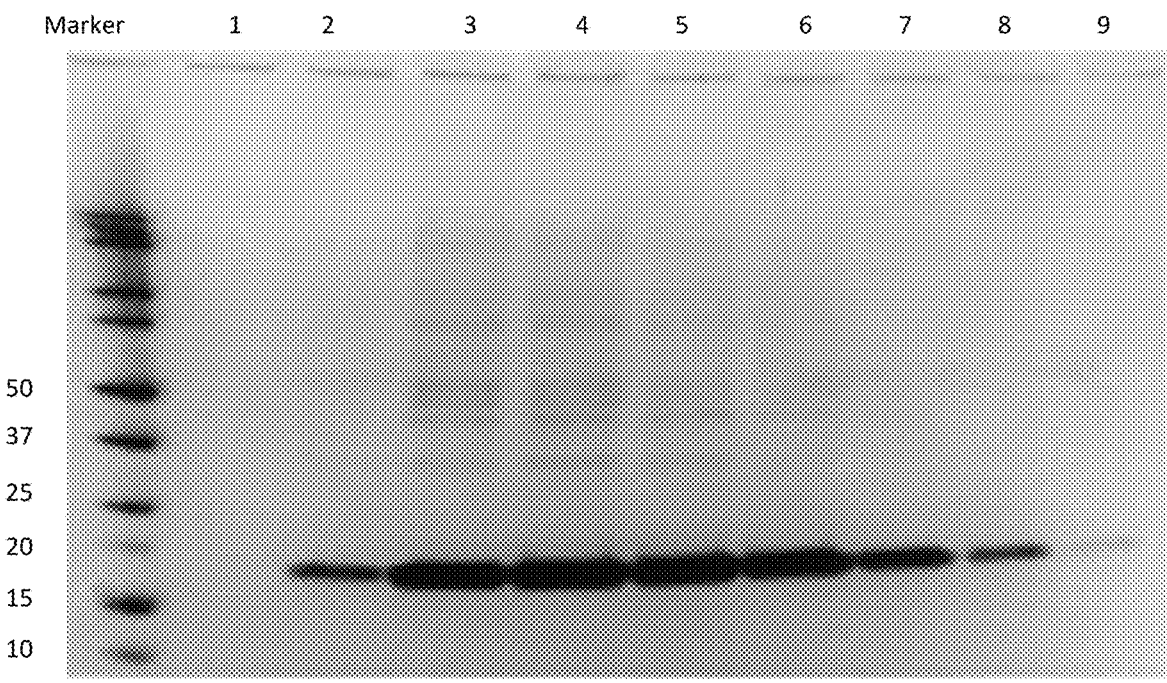

Notably, FIG. 3 shows the comparison of G-CSF-His produced in two identical Bio-MODs. (A) shows UV traces from purification runs on two identical Bio-MOD devices. (B) shows a magnified view of the detected affinity (dashed line window) and polishing (solid line window) elution peaks; 100 µL polishing fractions were collected from within the detected polishing collection window. (C) and (D) show the corresponding pressure profiles from the integrated pressure sensors measuring the pressure at the back of each of the Bio-MOD syringe pumps. (E) and (F) show the corresponding silver stained SDS-PAGE. Each lane was loaded with 20 µL of samples taken from 100 µL fractions of polished samples collected in the polishing window. In-line conductivity sensors are also considered for incorporation in the purification module along with other analytics, as described herein below.

Additionally, numerous types of lyophilized cell extracts can be used in the Bio-MOD system, including but not limited to *E. coli*, Vibrio, CHO and Tobacco (plant) cell extracts for use both batch and continuous manufacturing approaches. Further, numerous types of purification can be conducted including using a i) His-tag; ii) immobilized metal affinity chromatography (IMAC) followed by Ion exchange chromatography (IEC); iii) tagless intein-based purification; iv) tagless production and purification using chromatofocusing and polishing with IEC; and v) affinity purification using a G-CSF receptor as the capture agent (this has the added advantage of serving as a self-referenced potency assay).

Figure 4:
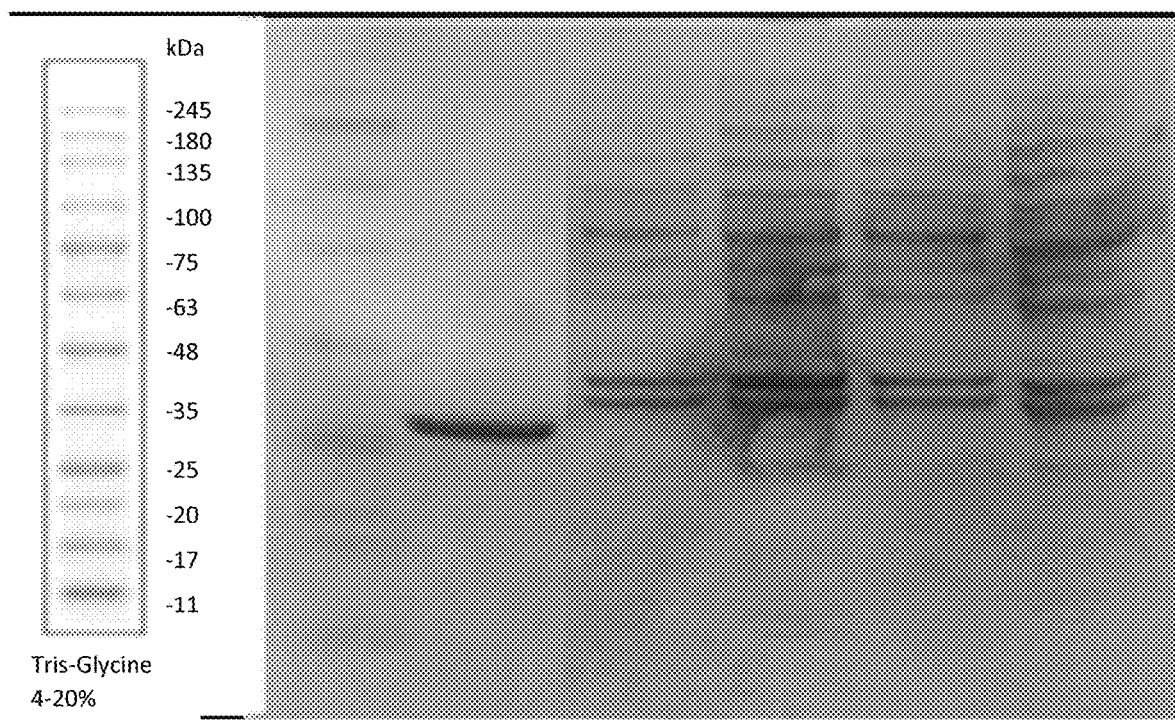
FIG. 4A shows the verification of expression of Ranibizumab in *E. coli* expression host; Lane 1: Protein marker—Blue-green color 25 KD, Lane 2: Standard, Lane 3 to 6: Rani Rani clone 1,2,3,4 respectively.
FIG. 4B shows the HPLC data confirming expression of light and heavy chain of Ranibizumab.

As shown above, G-CSF was produced with acceptable purity and potency with the present Bio-MOD system. In response other proteins have been produced including Ranibizumab, also known as Lucentis, which is a 48 kDa humanized monoclonal antibody fragment. Normally, this protein is produced as inclusion bodies in *E. coli*. In the present invention, the whole antibody fragment was successfully cloned under the T7 promoter such that there is a Shine-Dalgarno sequence in between the light and heavy chains for the equal expression of both chains. The native Ranibizumab gene was accessed from GenBank was synthesized and cloned into the pET-15b vector. The ligated plasmid-Ranibizumab mixture was transformed into competent *E. coli* DH5α cells and selected on Luria broth (LB) plates containing 100 µg/mL ampicillin at 37° C. The positive transformants were verified by restriction digestion and sequencing. The positive clones were further transformed into BL21(DE3) pLys S cells and their expression was confirmed by SDS PAGE and HPLC analysis (shown in FIG. 4).

Figure 4B:
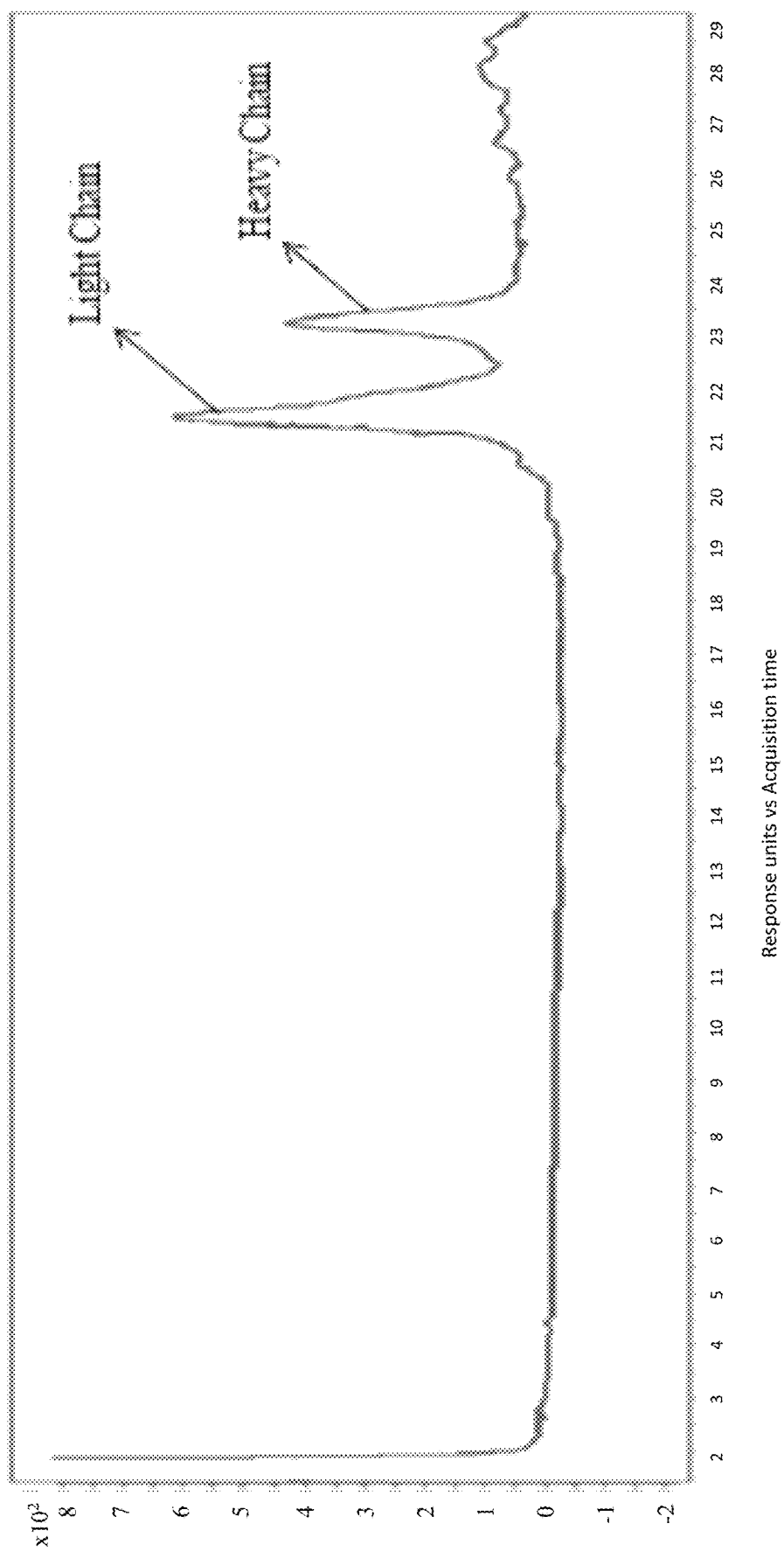

FIG. 4A shows the verification of expression of Ranibizumab in *E. coli* expression host. Lane 1: Protein marker—Blue-green color 25 KD, Lane 2: Standard, Lane 3 to 6: Rani clone 1,2,3,4 respectively and FIG. 4B shows the HPLC data confirming expression of light and heavy chain of Ranibizumab. Optimization of media, induction concentration and temperature required for maximum possible protein production has been done at shake flask level. The highest protein titre of 0.3-0.4 mg/mL using HPLC was obtained in optimized modified SOC medium at 37° C. with 1 mM IPTG induction concentration.

The cell free expression of G-CSF in the Bio-MOD system demonstrates the ability to consistently manufacture pure and potent product and animal studies have been successfully conducted. Since the Ranibizumab (Lucentis™) Fab antibody fragment is a heterodimer with disulfide bonds within and between each dimer, the cell-free production of the present invention offers special advantages. First, experience suggests that folding is improved if some amount of light chain can accumulate before heavy chain production begins. This is easily achieved by first adding only the plasmid with the light chain gene and then, after an optimal delay, adding the heavy chain expression gene. Secondly, direct access to the reaction solution allows for adjustment of the —SH/S—S redox potential and the disulfide isomerase concentration for optimal folding. In addition, recent experience suggests that adjusting the ionic strength of the reaction solution can improve protein folding. This may be especially advantageous since heavy chain binding domains often present hydrophobic residues. Finally, direct access allows the addition of chaperones (such as Skp and FkpA) at optimal concentrations to further improve folding. Such features can be optimized to achieve high Lucentis concentrations and product quality.

To demonstrate feasibility of also producing a reagent protein the GBP was used as a model. GBP is a fluorescent biosensor for micromolar levels of glucose. The GBP produced in the Bio-MOD (runs 056 and 057) were confirmed by SDS-PAGE and western blot analysis. After offline labelling with the fluorescent dye acrylodan, a ~45% change in fluorescence at the highest glucose concentration (FIG. 12A) was observed, consistent with results using GBP expressed in *Escherichia coli*. The binding isotherm shown in FIG. 12B also agrees with GBP expressed in whole-cell methods.

Figure 12:
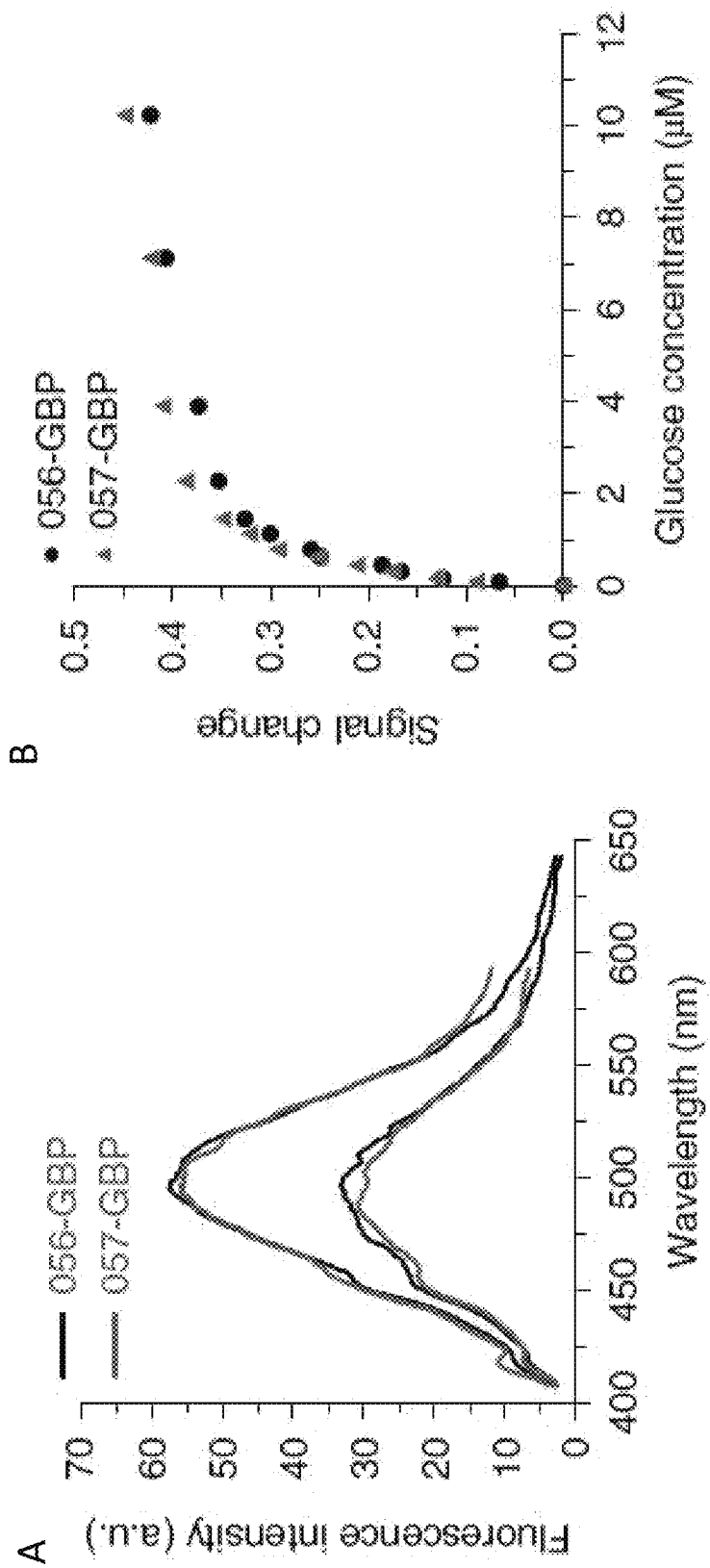
FIG. 12 shows the characterization of GBP and EPO produced by Bio-MOD.
Figure 12:
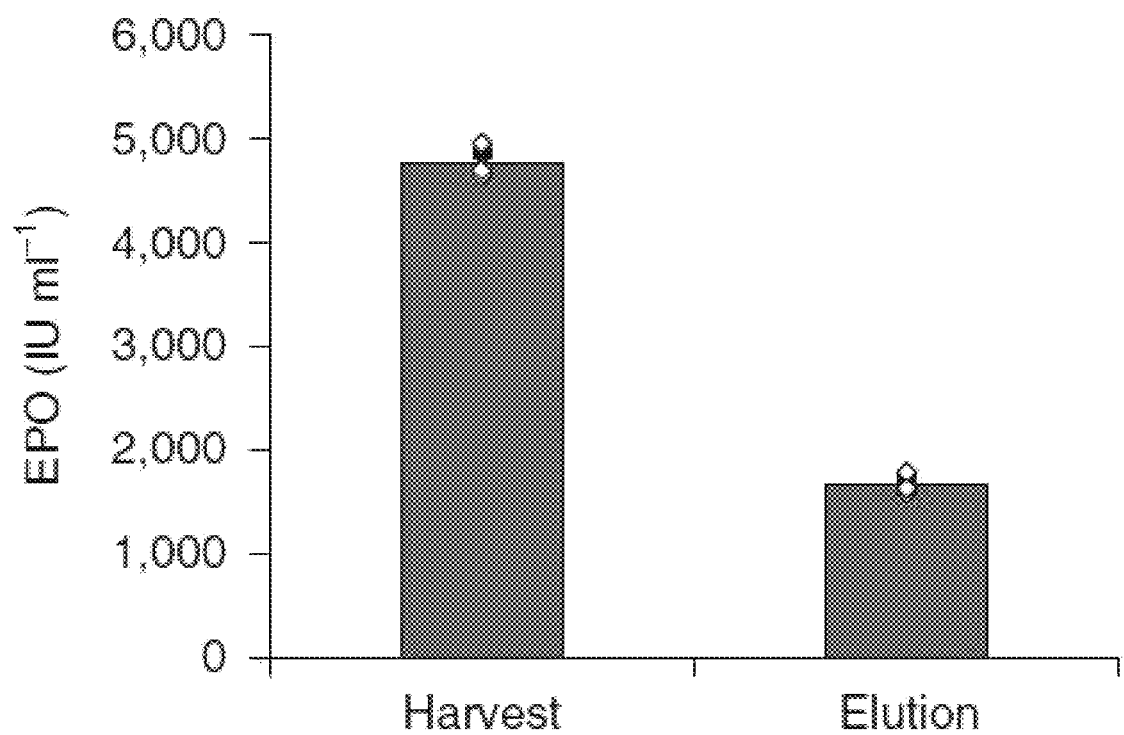

Post-translational modifications (PTMs) such as glycosylation are generally difficult to achieve in IVT due to the absence or decreased presence of the necessary organelles found in whole cells. To show the possibility of glycosylation in a Bio-MOD product, we chose EPO was chosen (40% glycosylated) as a model therapeutic. EPO is a hormone that stimulates the development of red blood cells and is used to treat anaemia in patients such as those undergoing dialysis. Supplementation of the cell-free lysate with CHO microsomes (30% of the total reaction mixture) resulted in successful glycosylation of EPO-His as evidenced by a shift in molecular weight from 25 to 20 kDa following treatment with peptide: N-glycosidase F (PNGase). A slowing down of the reaction by decreasing the reaction temperature and not supplementing the reaction with GADD34 (see Methods) also contributed to successful glycosylation. Enzyme-linked immunosorbent assay (ELISA) indicated proper protein folding after the affinity purification, as shown in FIG. 12C. In previous experiments, low levels of glycosylation in EPO were observed in CHO IVT lysate, which proves that the small amount of microsomes already present in the lysate survive lyophilization. Thus, in the future, microsomes can be added to the liquid CHO IVT lysate before lyophilization. This will ensure full portability of the reaction mix for the production of glycosylated proteins. The basic design and use of the Bio-MOD system presents a miniaturized, rigorous and controlled production process that can minimize natural variations associated with protein expression based on living cells. The software for the purification procedure in the Bio-MOD incorporates the highest level of self-monitoring, giving the user the ability to press 'start', verify proper loading, walk away and return to a purified sample. Real-time self-monitoring has the advantage of being able to distinguish the 'acceptable' versus the 'unacceptable' runs based on specific (UV or pressure) profiles established from multiple runs.

Figure 6:
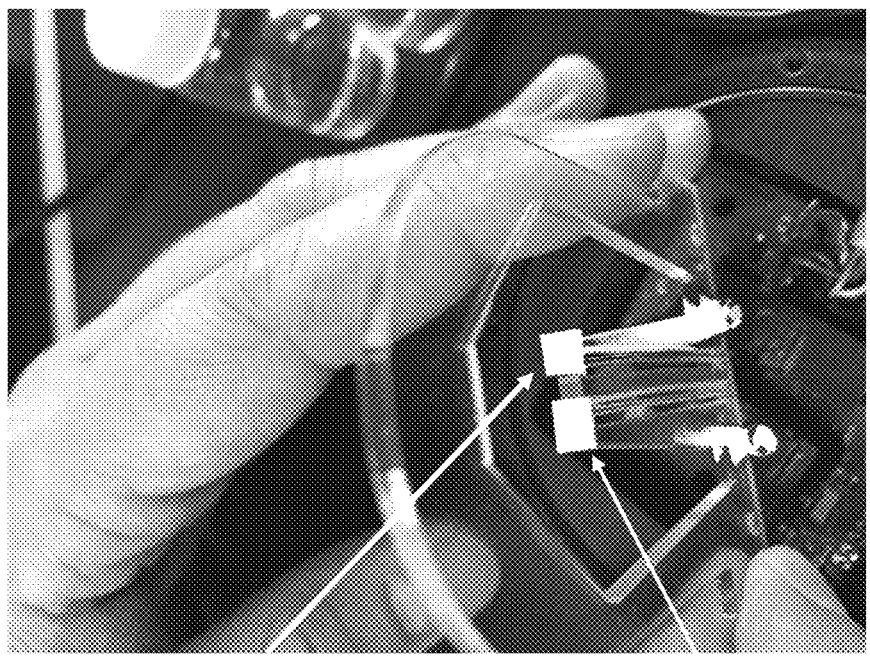
FIG. 6A shows a waveguide with dissolved oxygen and pH sensors designed to be inserted into dialysis cassette reactor.
FIG. 6B shows the consistency of DO and pH measurements in lysate in three independent minibioreactors. Arrow shows time of DNA addition.
Figure 6B:
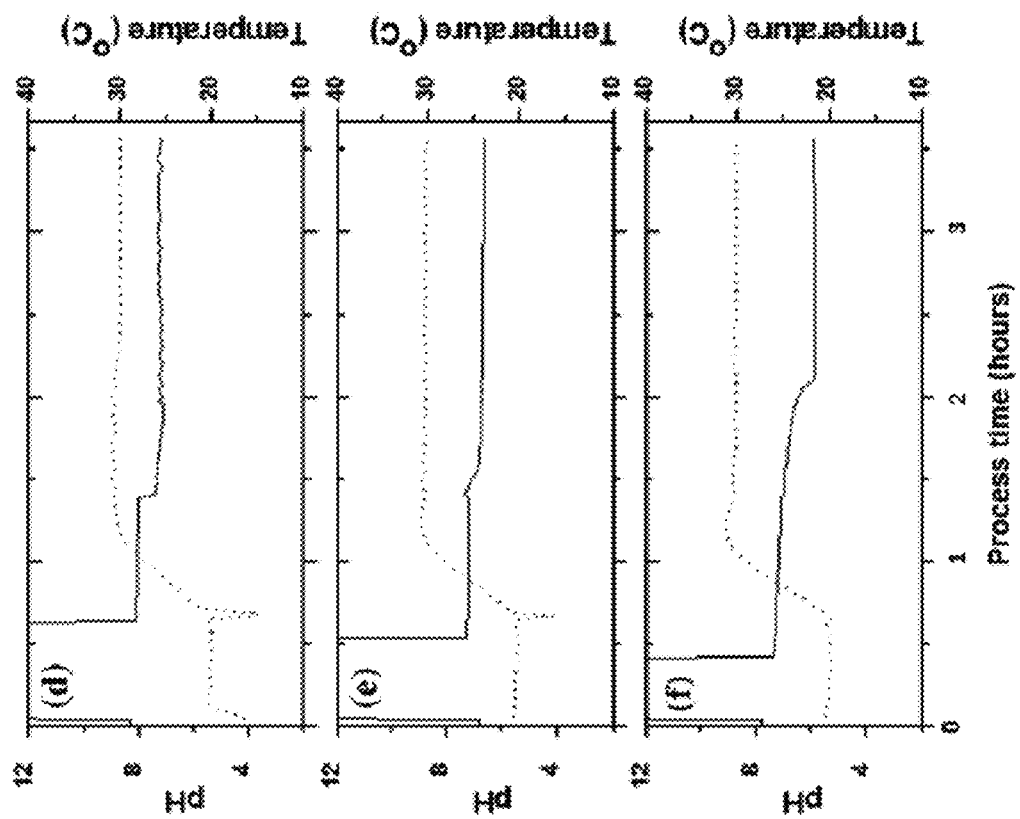
Figure 6B:
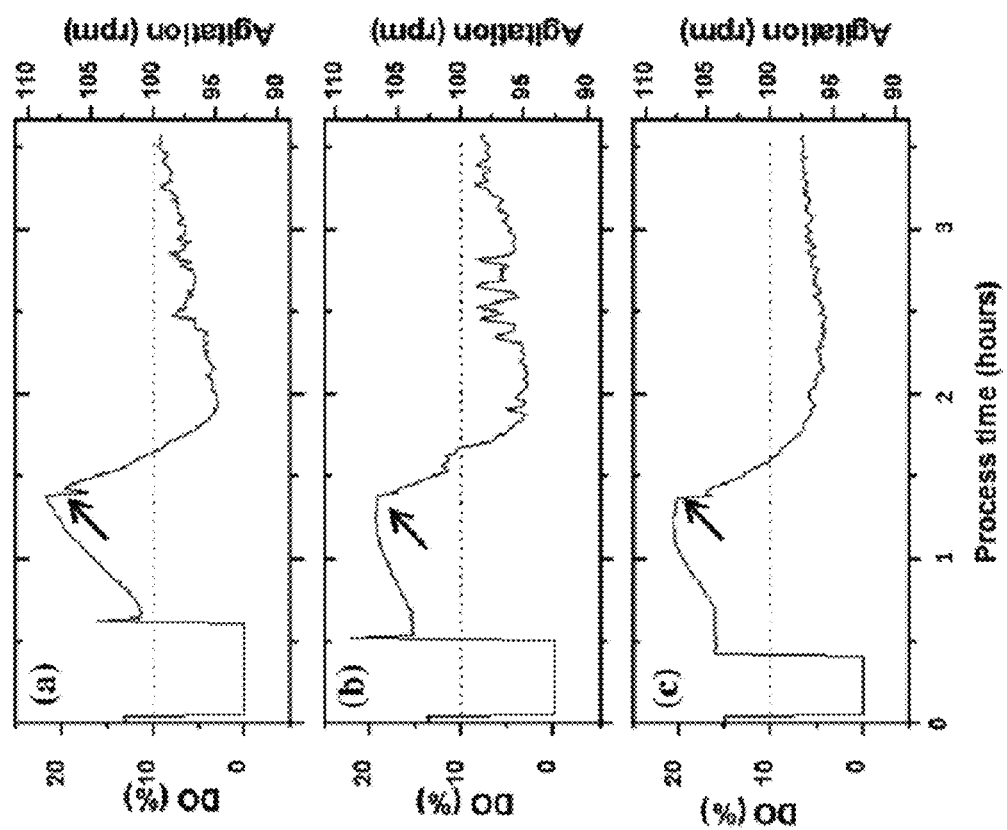

As discussed earlier, the point-of-care protein production platform described herein can use several purification methods. Usually, a histidine tag has been used for IMAC purification. For additional types of purification, chromatofocusing is considered an alternative non-affinity capture method as well as a potential polishing method. Prior work has demonstrated the utility of chromatofocusing for similar applications (14). Additionally, other options for use in the Bio-MOD platform include periodic countercurrent chromatography, simulated moving bed chromatography, and sequential multicolumn chromatography (15,16). By using a microfluidic approach, microcolumns can be fabricated and tested in conjunction with both batch and continuous cell-free expression in an optimized format by varying the column packings used, as well as the column geometry and interconnections. Design of Experiments (DoE) and Quality-by-Design (QbD) methods can be employed with the goal of achieving optimal performance and process control by exploiting a better fundamental understanding of the processes. Testing of such designs may employ simulations of the Bio-MOD system using the microfluidic module in COMSOL Multiphysics®, which is a finite element modeling environment currently available. (17). FIG. 6A shows the inclusion of waveguides for dissolved oxygen and pH sensors which are inserted I the dialysis cassette. Notably, FIG. 6B shows the consistency of dissolved oxygen and pH measurements in three independent minibioreactors. The arrows show time of the DNA addition (5).

Figure 7:
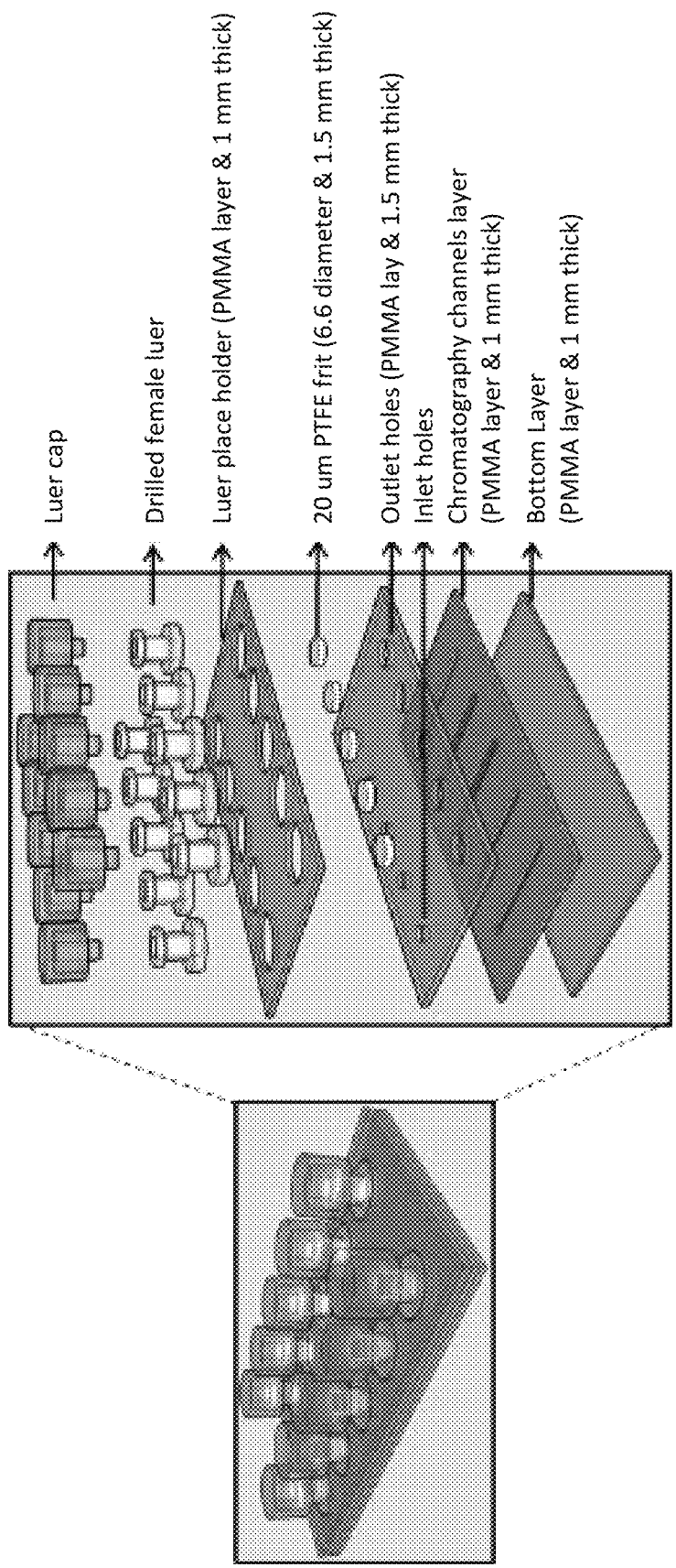
FIG. 7A show a CAD design of multiple column geometries.
FIGS. 7B and C show multi uniform columns made up of three layers of polymethyl methacrylate (PMMA); bottom base plate layer (each 1 mm thick), middle channel layer and top inlet/outlet layer (1.5 mm thick). The top layer contains a larger circular slot towards the outlet for PTFE frits. PTFE frits were added post bonding. This array consists of 5 columns of 100 μL volume
FIG. 7C shows customizable microscale column device (μCol) an array of columns with varied resin capacities (25-200 μL, from left to right) displaying the versatility of this.
FIG. 7D shows an integrated mixer, capture and polishing column.
FIG. 7E shows the Silver stain data, captured using 25 UL Cobalt micro column and polished using 500 μL micro column of the column in FIG. 7D.
FIG. 7F shows alternative continuous processing schemes.
Figure 7B:
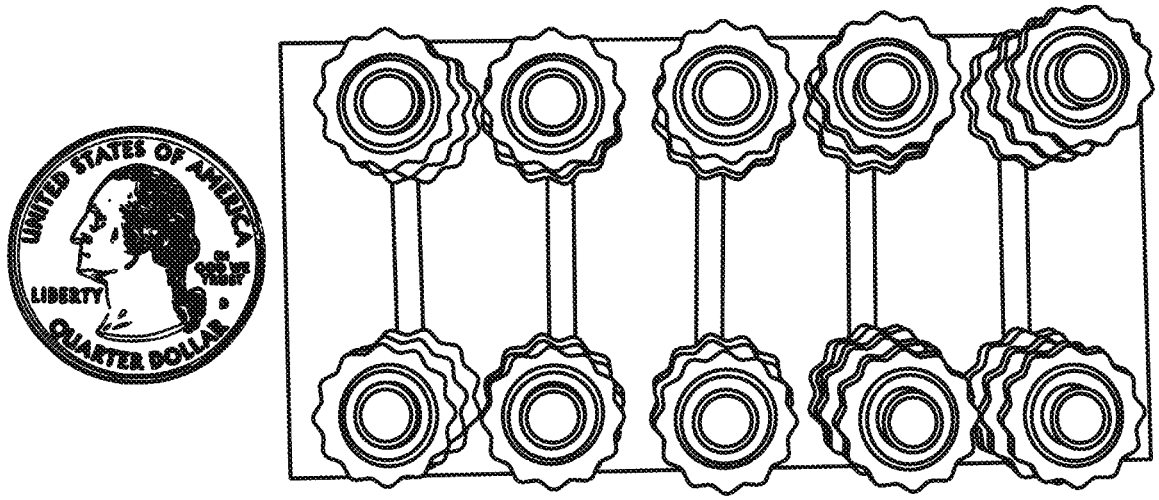
Figure 7C:
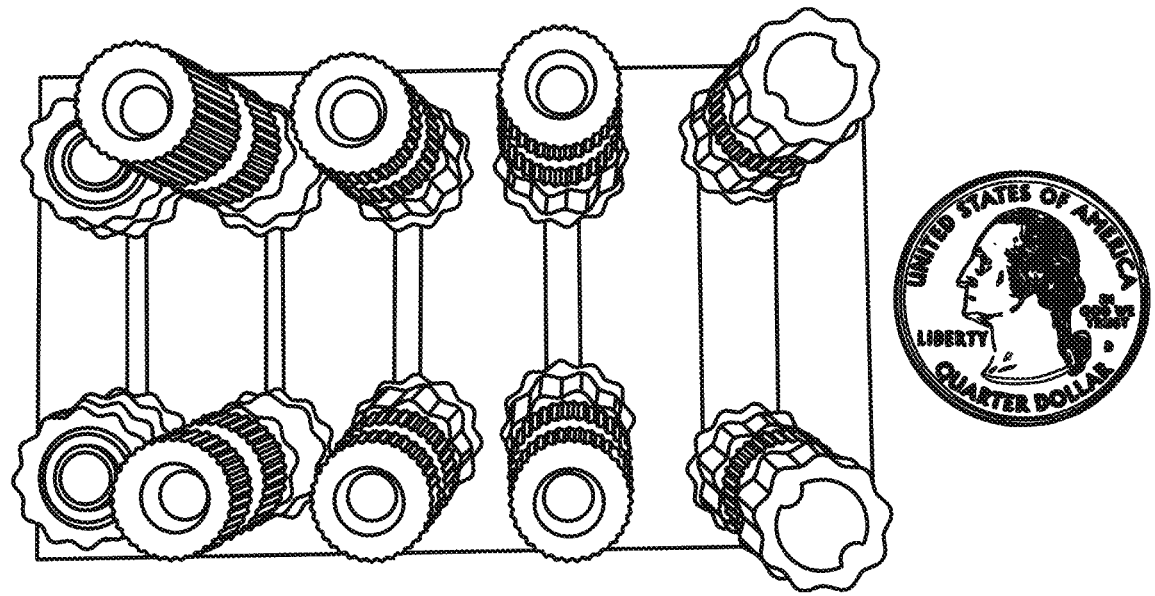
Figure 7D:
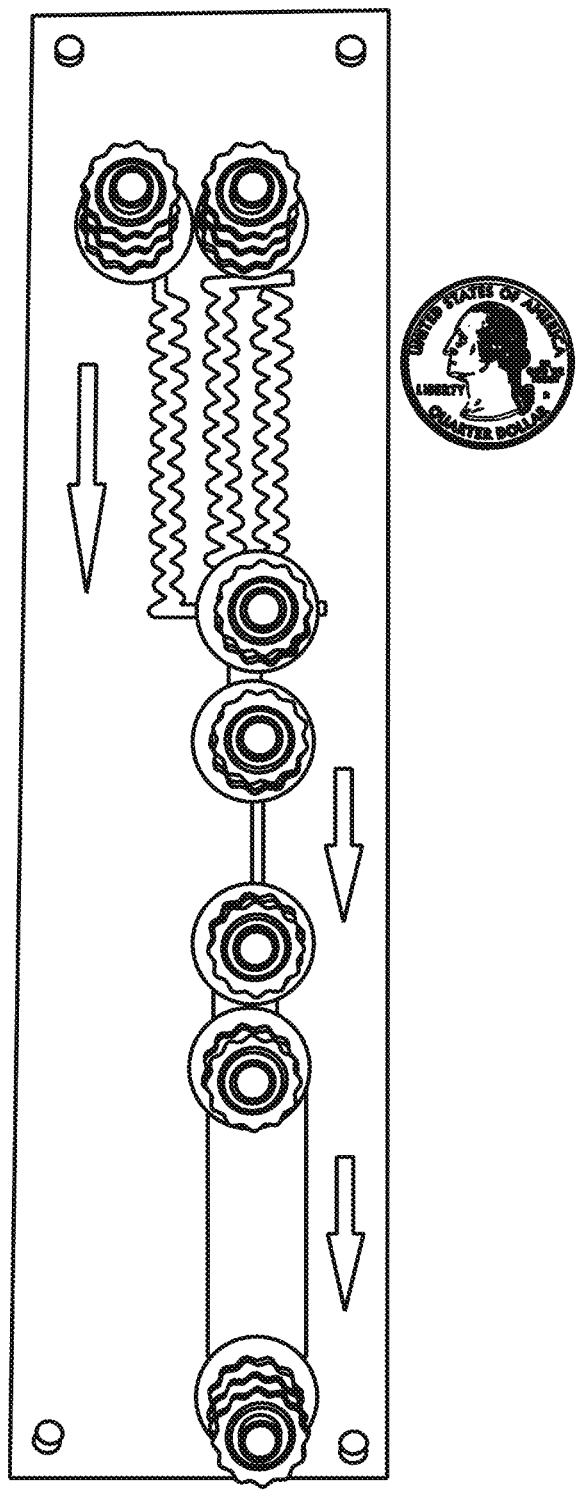
Figure 7:
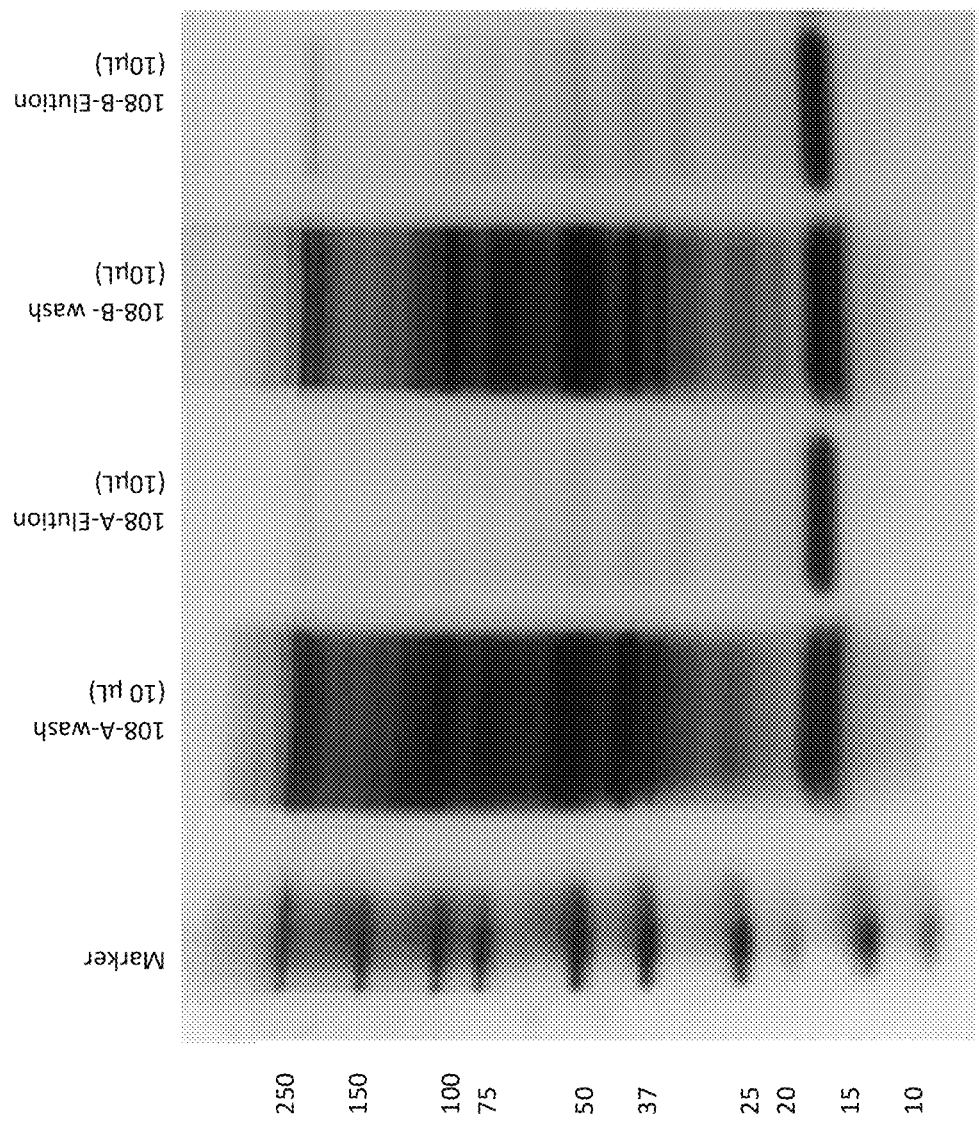
Figure 7:
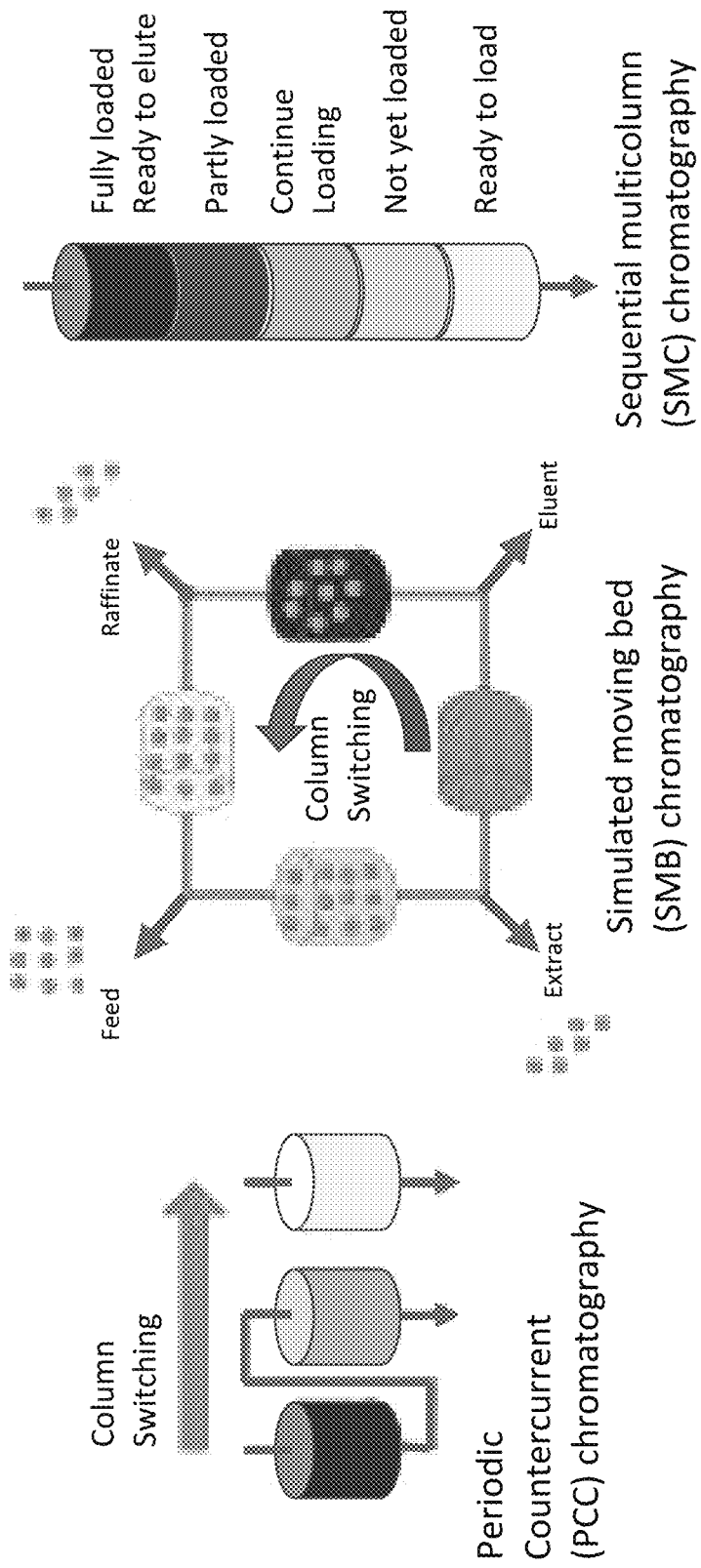
Figure 8:
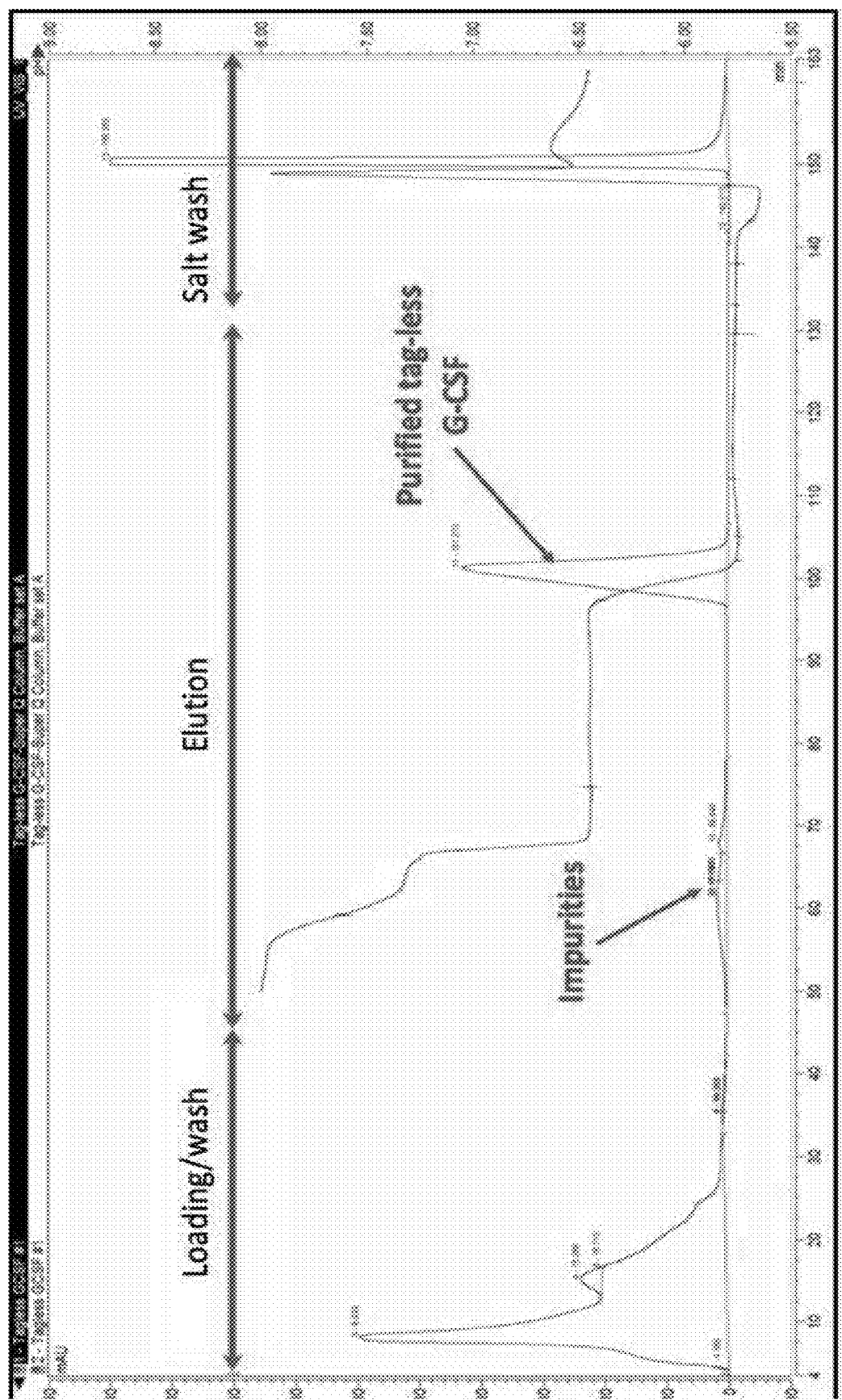
FIG. 8A shows chromatofocusing as a capture step for tag-less G-CSF expressed in *E. coli* lysate. Column: 0.7 mL Super Q Buffer A (Loading/wash): 10 mM MOPS, 10 mM Bicine, pH=7.90.
FIG. 8B shows the analysis of the collected fractions. Lane 1, molecular weight marker; lane 2, G-CSF Standard (50 ng); lane 3, G-CSF Standard (150 ng); lane 4, G-CSF Standard (200 ng); lane 5, impurities; lane 6, purified tag-less G-CSF (1 μL); Lane 7, purified tag-less G-CSF (35 μL)
FIG. 8C shows the results of analytical Size Exclusion Chromatography (SEC) of the purified tag-less G-CSF.
Figure 8:
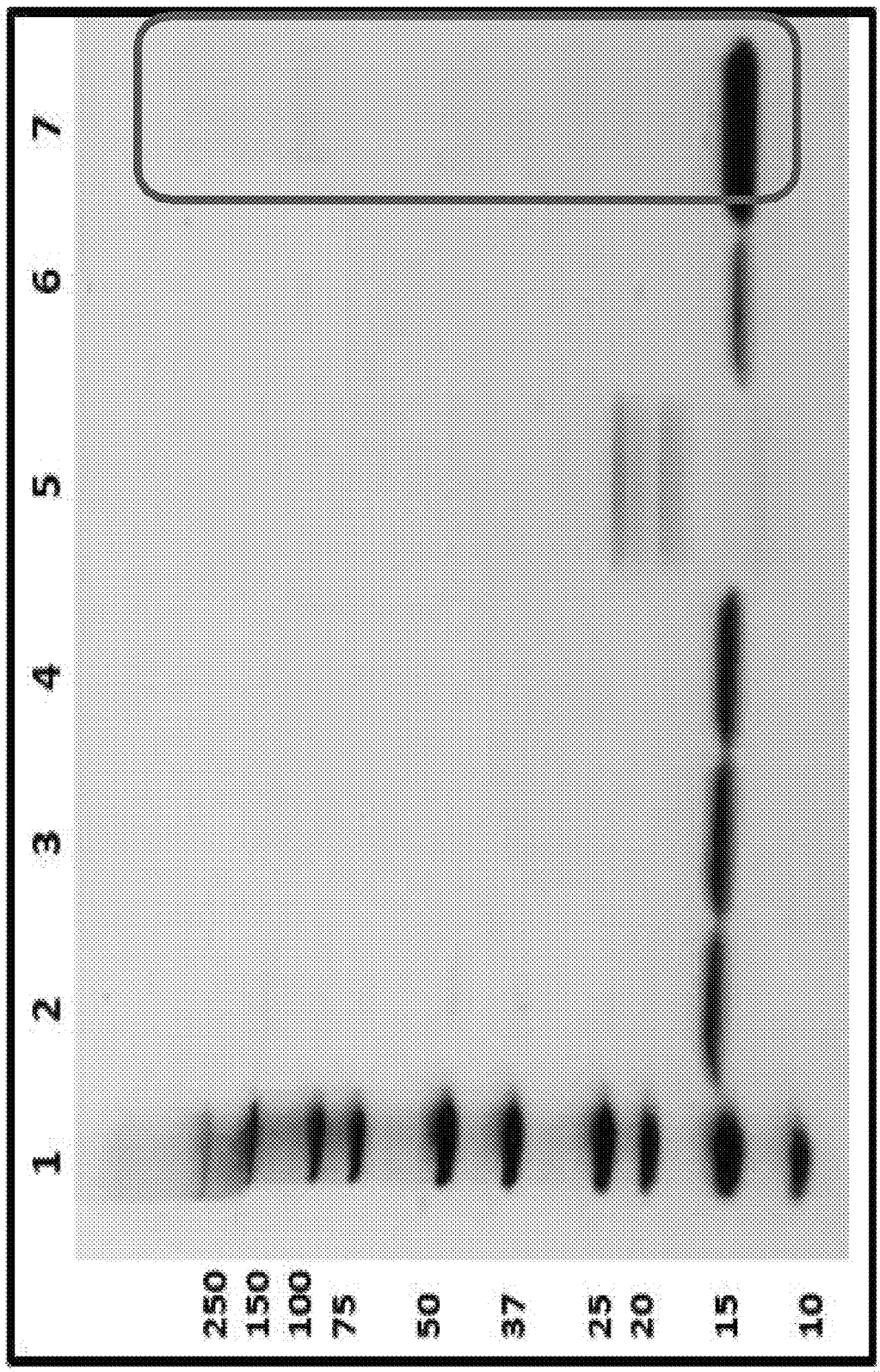
Figure 8:
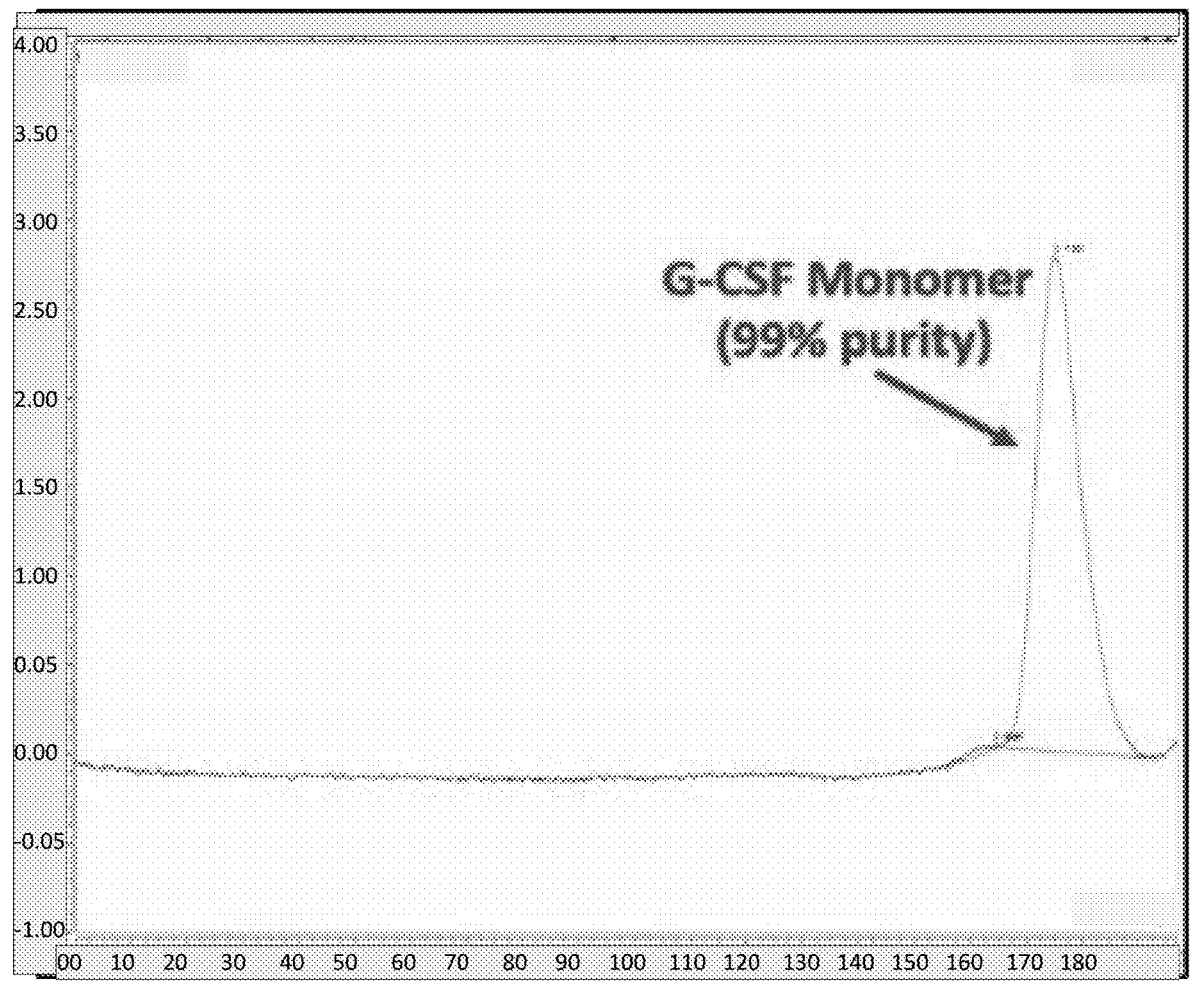

FIG. 7 illustrates some of the basic elements for purification including A. show a CAD design; B. Multi uniform columns; C. Varying capacity columns; D. Integrated mixer, capture and polishing column; E. Results from G-CSF capture and polishing using it, and F showing various continuous processing schemes. Additional steps may include additional purification steps prior to cell-free protein synthesis. This includes cell lysis and centrifugation steps to remove cell walls and aggregates. Also phase extraction can be applied along with affinity chromatography, and expanded centrifugation steps to better clarify extracts prior to use, simplify purification and decrease the risk of contamination. In the event that aggregates pose a problem, an additional size exclusion step can be added.

The present invention provides for not only a robust real-time release of drug to the patient but also in-line (rather than off-line) quality analysis of the produced protein with sensors. Real time sensors are included for determining product concentration and quality. Such sensors may include but not limited to silver stained gels, Labchip, HPLC, Blitz, ELISA, CD, UV-Vis, fluorescence and flow cytometry (potency). Importantly, in the present invention, the extracted data is included in a machine learning system and compared with previous results from off-line testing and other on-line testing. The process data for bio-derived medicines can include chromatography data: UV (260-280), fluorescence, pressure, conductivity, light-scatter, CD, etc. Such useful feature extraction from process control data is correlated to product quality through previous batch runs. The machine learning can them optimize extraction or choice of features that best describes changes in the process relevant to product quality.

The characteristics of protein detection and quantitation were evaluated. Sodium dodecyl sulfate-polyacrylamide gel electrophoresis (SDS-PAGE) analyses is used. Criterion TGX™ precast midi protein gel (4-20%) is used following standard protocol with a Criterion™ electrophoresis cell, both obtained from (Bio-Rad, cat. #1656001 and #5671093). For staining gels, ProteoSilver™ plus silver stain kit (Sigma-Aldrich, cat. #PROTSIL2) is used. Known concentrations of cell-derived glucose binding protein (GBP), G-CSF (Life Technologies) or bovine serum albumin (BSA) are loaded along each sample and used as standard reference for determining the purity and the concentration of purified protein. The area of each band is measured with ImageJ software and the concentration calculated relative to the standard curve. Percent purity is determined using the same image analysis software by taking the ratio of the area of the known, lowest detectable band vs. the total area, where the total area is equal to the area of the lowest detectable protein band plus area of impurities in an overloaded gel. 660 nm assay. Quantitative protein analysis is done using Pierce 660 nm protein assay kit (Thermo Scientific, Cat. #22660) following manufacturer's recommended protocol. Western Blot and ELISA. The G-CSF samples are diluted 10× with PBS. 20 µL aliquots and treated with 6 µL of 5× diluted Laemmli buffer dye, boiled at 100° C. for 5 minutes, then loaded to a pre-cast 12.5% tris-HCl gel (Bio-rad, Cat. #3450014) and run at 100V. Samples are then transferred to a nitrocellulose membrane (Bio-rad, Cat. #1620233) and left in 20-mL blocking buffer overnight. Primary antibody (Rabbit anti-G-CSF, Abcam, Cat. #9691) is added at a concentration of 1:3000 to 20 mL blocking buffer the next day, removed after an hour, and the blot is washed with PBST. Fresh blocking buffer (20 mL) is then added with a complementary HRP-conjugated secondary antibody (Goat Anti-Rabbit HRP, Abcam, Cat. #ab6721) at a concentration of 1:3000. Solution is removed after 1 hour, and the blot is washed with PB ST. Finally, a chemiluminescent substrate (Thermo Scientific, Cat. #34075) is added to the blot and imaged using a Thermo Scientific myECL™ Imager. The same antibody is used for an ELISA assay. Reversed-phase and size exclusion high performance liquid chromatography (RP-HPLC) of G-CSF IMAC-purified samples is analyzed on a Dionex Ultimate 3000 series HPLC system (Thermo Fisher Scientific, Bannockburn, Ill.) using a BioBasic C18 column (Thermo Scientific). Mobile phase A consists of 0.1% TFA in water while mobile phase B consists of 0.1% TFA in acetonitrile. Gradient elution of 30-100% B in 25 minutes at a flow rate of 0.5 mL/min is used.

G-CSF is a pleiotropic cytokine that is heavily involved in hematopoietic cell differentiation and function. The activity of G-CSF is studied. Multiple functions of G-CSF are compared directly to purified recombinant protein from commercial vendors by 1) quantifying JAK2/STAT3 signaling by Western blot and phospho-flow cytometry (18); 2) evaluating the differentiation of G-CSF-treated bone marrow precursors to granulocytes by flow cytometry, Wright-Giemsa staining for granulocytes, and gene expression using real-time quantitative reverse transcription PCR qRT-PCR (19, 20 and 3) assaying the polarization of tolerance-inducing blood monocytes by flow cytometry and ELISA (21). The latter two in vitro assays are directly related to potential therapeutic uses of G-CSF in the clinic for post-radiation recovery and tolerance-inducing therapies in autoimmunity, respectively.

Additional real-time analytics can also be conducted. For example, real-time sterility testing is conducted for detection of bacterial contamination using resazurin as indicator (22, 23). The dye is oxidized by NADH in the cells and converted into highly fluorescent rezorufin. The incubation is performed in a microfluidic chip and is monitored using a miniature fluorimeter. The rate of fluorescence increase is proportional to CFU in the sample. The method integrates a negative control to account for oxidation properties of the other possible reactive substances.

Figure 9:
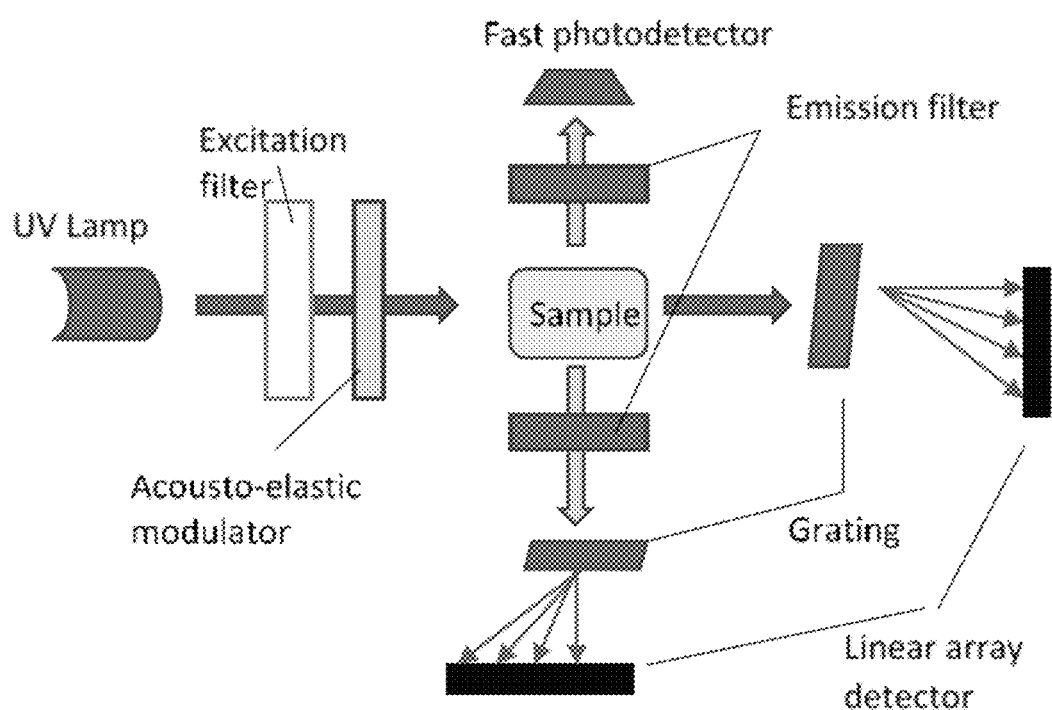
FIG. 9 shows the real-time multi-parametric sensor with absorbance, CD, fluorescence and lifetime measurement.

Product concentration is determined with a rapid, microfluidic ELISA technique previously used and demonstrated for Staphylococcal Enterotoxin B (SEB) (24-26). In addition, an in-line optical sensor is used for real time fingerprinting and quality assessment of the final product. This is shown conceptually in FIG. 9 and captures data on absorbance, CD, fluorescence and lifetime measurements. For example, G-CSF is interrogated optically in a flow cell of a UV sensor before it is collected in a vial for delivery to the patient. Absorption correlates with protein concentration and together with intrinsic fluorescence can be used for fingerprinting of the sample and for evaluation of its purity (27). Protein fluorescence is due to tryptophan residues ($\lambda$.ex=280 nm, $\lambda$.em=350 nm) and to a limited extent, tyrosine and phenylalanine. Another fingerprint can be obtained by measuring the intrinsic fluorescence lifetimes. These lifetimes are obtained by modulating the intensity of the light source and detecting the time lag as well as the amplitude change of the emission using a fast output detector. Cross correlation decreases the frequency of operation, permitting the use of simpler and less-expensive optical components. Because tryptophan fluorescence is highly dependent on environment, fluorescence wavelengths and lifetimes can inform on the structure and integrity of the protein structure (27). Yet another fingerprint can be obtained by in-line measurements of the circular dichroism. This will be done by keeping the intensity of the UV light source constant, while modulating its polarization using an acoustoelastic modulator. CD data provides real-time information on protein secondary structure and whether the protein product is folded correctly. The current off-line measurements are used to validate the in-line ones and feed the machine learning algorithms of the software for in-built PAT.

Process Software and Machine Learning Module:

To provide adequate controls and the need to have statistical analysis of each process and the product produced, machine learning is used in the Bio-MOD system. Notably, traditional product testing for therapeutic manufacturing involve analysis tools such as NMR, Mass Spec, Raman, NIR and more. Though some of these tools can be implemented at the output of the Bio-MOD (Raman, NIR, and Fluorescence), some methods are not as feasible (NMR, Mass Spec). Thus, to supplement the gap in product testing, the present Bio-MOD uses machine learning. Importantly, because of the sensor data and the fingerprint profiles that each batch provides, the results of each run, such as a series of training runs, can be used to populate information relating to product quality and potency. Such data is burned into a memory chip uniquely for each biologic to be made (for example G-CSF). The number of training runs is determined as the project progresses and based on statistical Analysis of variance (ANOVA) of all of the profiles. In order to incorporate various sensor fingerprints, the Bio-MOD system uses a multi-sensor data fusion approach, capturing statistical significance across the multi-sensor array. The data is pre-processed, and informative features are extracted using vector analysis methods.

The artificial intelligence (AI) deep learning module utilizes a trained classifier along with security protocol inputs to perform real-time release testing of the final sample. Model parameters and classification results are connected to a server in the cloud or a ground server, updating the learning model and validating the process with a verified database. Google has recently announced the availability of a secure, cloud-based AI platform that allows any user access to their new Tensor Processing Units (TPUs). This is a potential game changer for biologics manufacturing, since many of the relevant data are specific to temporal events (such as the spectrum of a peak eluting at a certain time, ran under a certain buffer composition, flow rate, pressure etc.) and are readily represented as matrices or tensors. For the Bio-MOD, TPUs is used to perform real-time matrix decomposition and artificial neural network implementation needed for feature extraction and parameter estimation used in the machine learning module.

Figure 10:
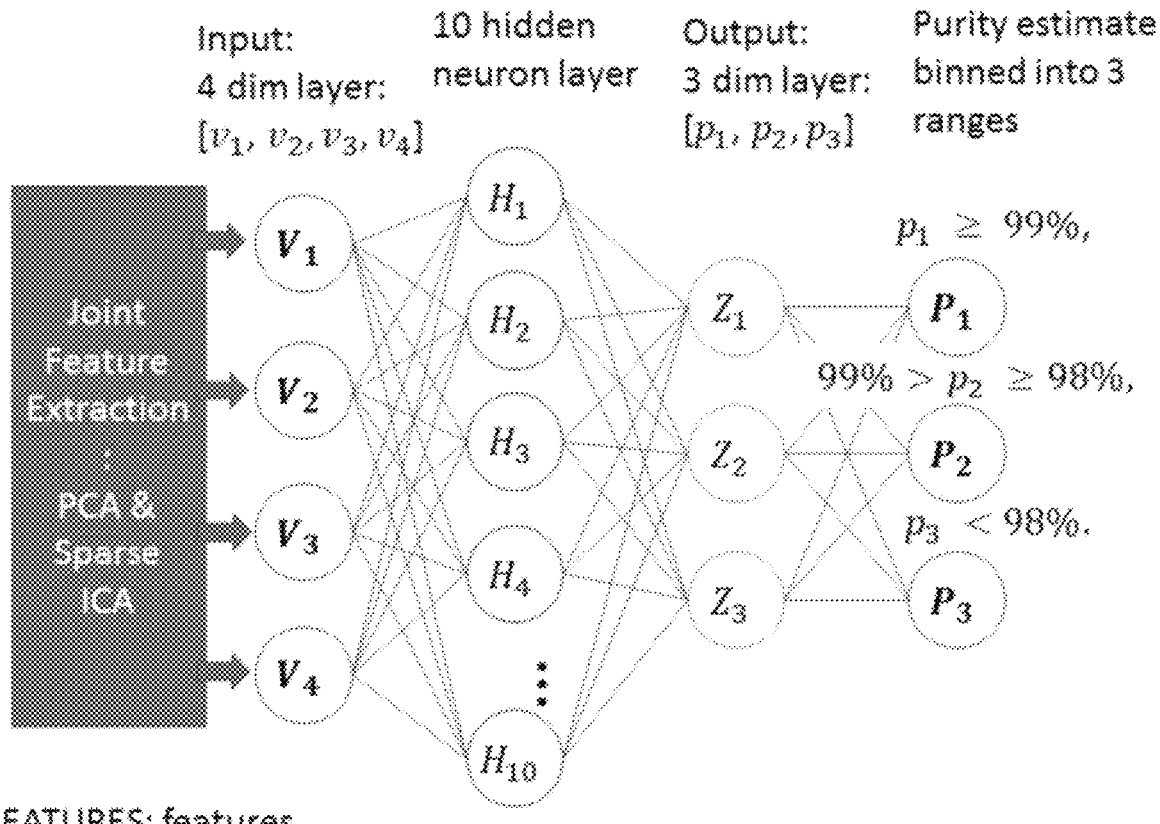
FIG. 10A shows result of using the ANN method wherein the top four principal component weights were extracted and input into a 2-layer feed forward ANN with a 10 hidden neuron layer.
FIG. 10B (i) and (ii) shows the product purity.
FIG. 10C shows attributes of the corresponding runs where binned into three ranges: (output layers $p_1$, $p_2$, $p_3$) greater than 99%, between 98% and 99%, and less than 98%.
FIG. 10D shows the high correlation of the ANN fit.
FIG. 10E is a schematic of the steps involved in the production of proteins including the use of machine learning.
Figure 10:
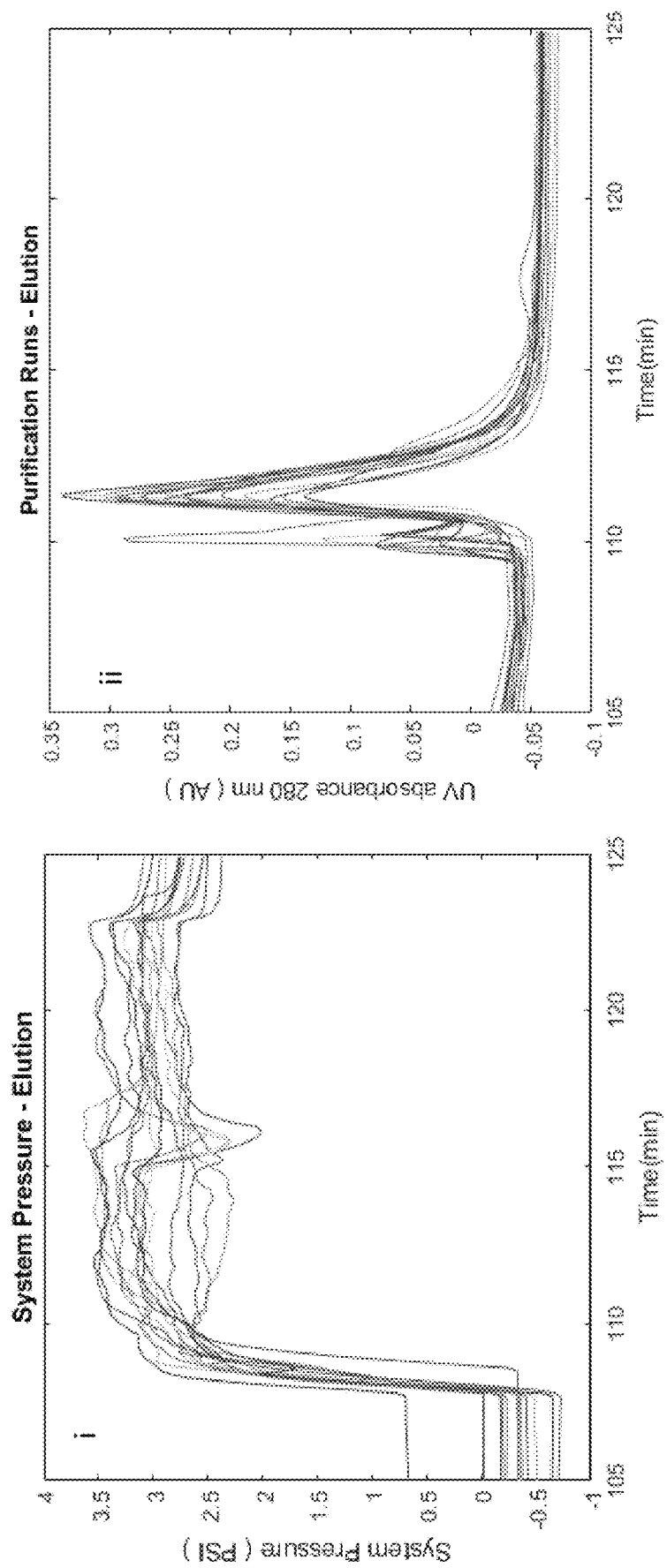
Figure 10:
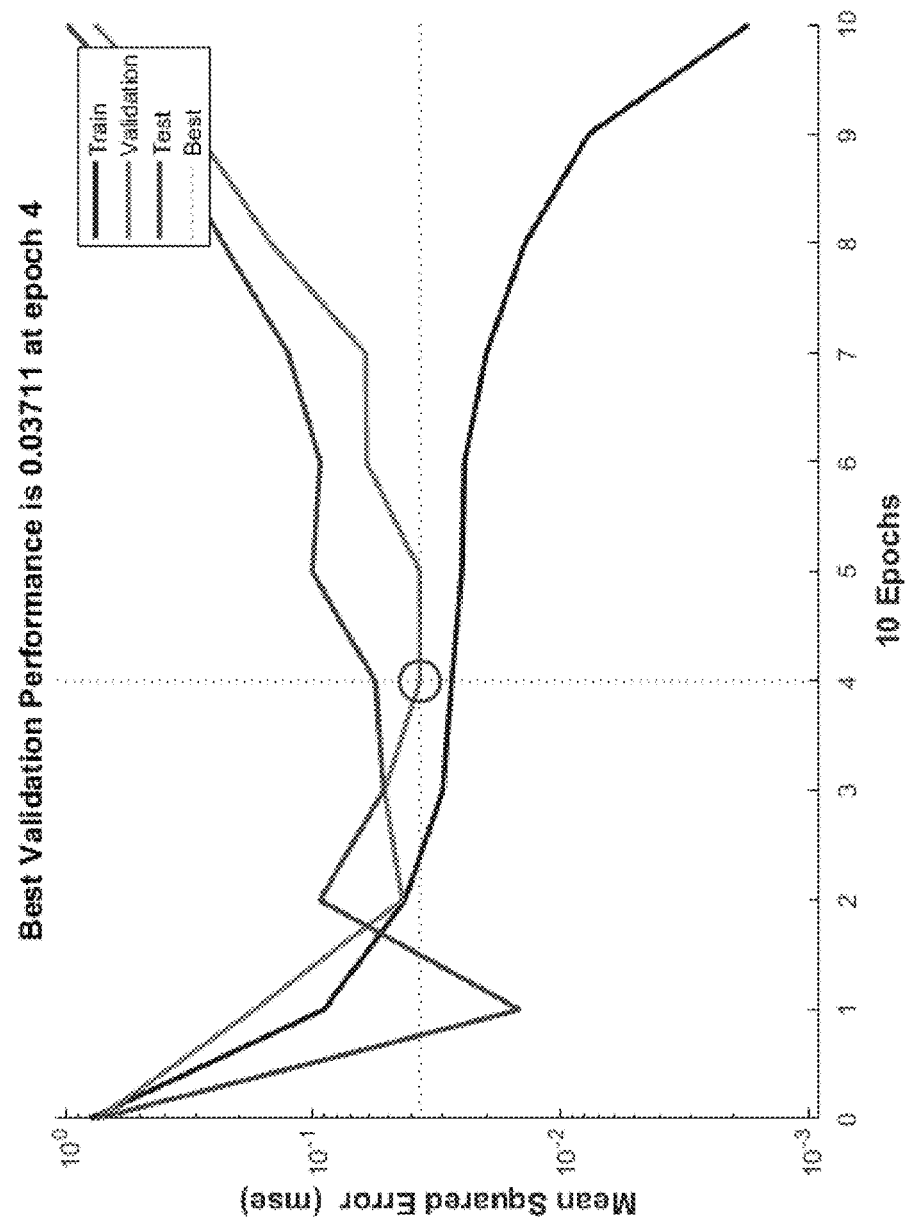
Figure 10:
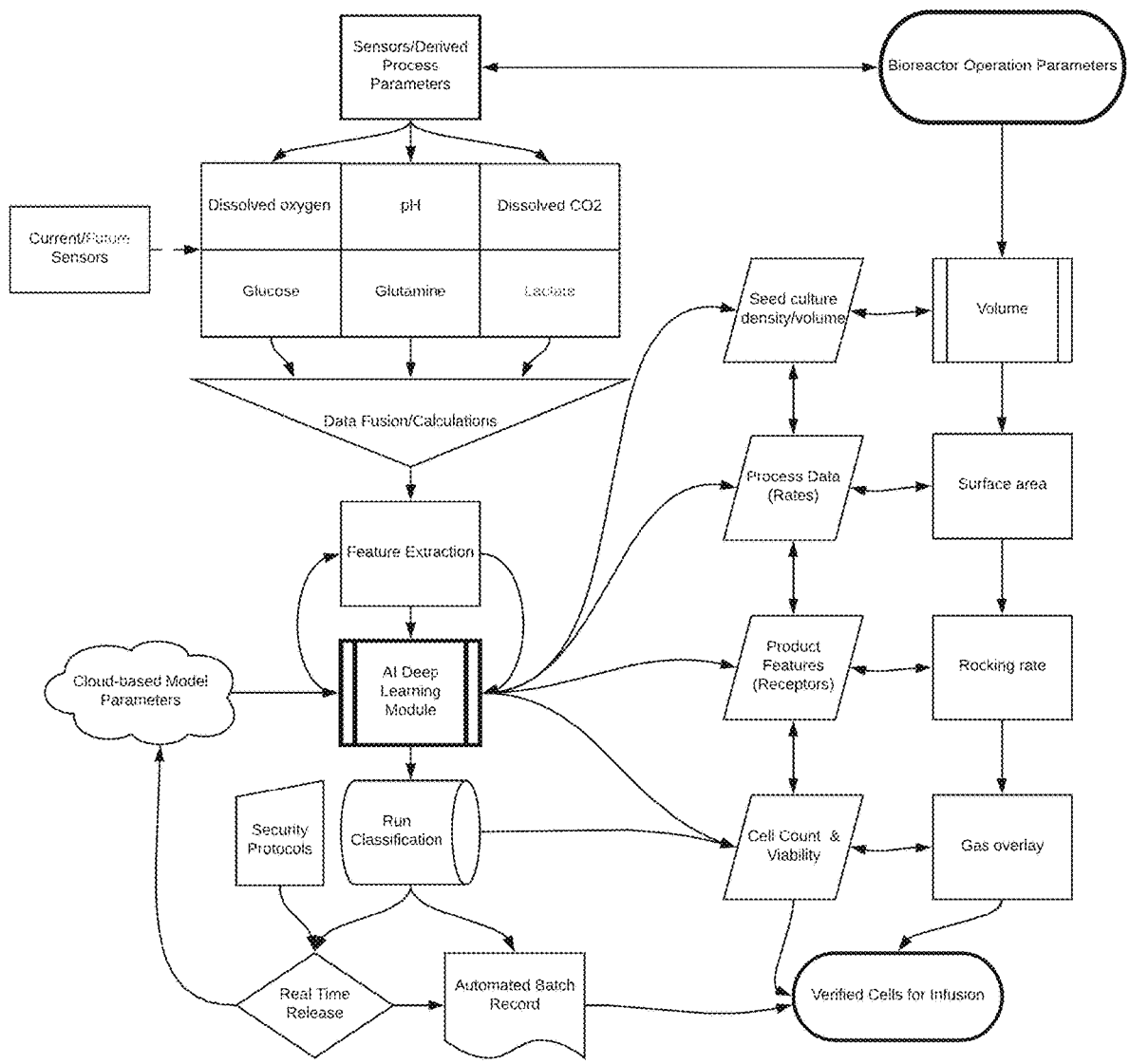

In addition, a camera-based video image device observes all the fluidics and detects any bubbles, leaks, debris etc. that may result from abnormal operation. Based on just the UV and pressure sensor profiles, the Bio-MOD system has already demonstrated the capability to estimate purity and concentration, detect process deviations and reject a run. Through the development and testing of the Bio-MOD devices, a range of different conditions and product quality attributes has been recorded. Extracting group features from this multi-modal sensor data, it has been shown that the data fits these features closely (R>0.9) to product quality attributes (purity, aggregation, concentration) using artificial neural networks (ANN) and support vector machines (SVM) as shown in FIG. 10.

Neural Networks for Blind-Source Separation

Frequently, machine learning systems are used to process data. For example, machine learning systems can be used to perform information retrieval or rank data items. The term machine learning system is generally intended to refer to a computer-related entity, either hardware, a combination of hardware and software, software, and/or software in execution.

The training of a learning system can be further explained by looking at a specific example. For example, the learning component can include a neural network. Neural networks are commonly used for classification. A neural network is commonly organized as a multilayered, hierarchical arrangement of processing elements, also referred to as neurons, nodes or units. In a hierarchical arrangement of neurons in a neural network, the neurons are usually arranged into layers. The output of a neuron in one layer can be an input to one or more neurons in a successive layer. Layers may be exposed in the sense that either the inputs of neurons in that layer directly receive input from a data source external to the neural network or the outputs of neurons are the desired result of processing. Layers may also be hidden in the sense that the inputs of units in that layer are computed using the outputs of units in a previous or lower layer, and the outputs of units in a hidden layer feed inputs for units in a successive or higher layer. An exemplary neural network can include any suitable number of layers such as an input layer, an intermediate or hidden layer and an output layer.

Blind source separation (BSS) is the art of separating out the source signals, with as its only assumption that these signals are statistically independent. In most BSS algorithms the additional assumption is made that that the mixing is linear. Sensors are sometimes used to observe a mixture of source signals. One known approach to BSS is independent-component analysis (ICA) which is an extension of a linear transform called Principal Component Analysis (PCA). It is aimed at extracting the independent sources when the source signals are active simultaneously and is a BSS algorithm depending on using the Artificial Neural Networks. (28-29)

A neural network (NN), in the case of artificial neurons called artificial neural network (ANN) is an interconnected group of artificial neurons that uses a mathematical or computational model for information processing based on a connectionist approach to computation. In most cases an ANN is, in formulation and/or operation, an adaptive system that changes its structure based on external or internal information that flows through the network. Modern neural networks are non-linear statistical data modeling tools. They are usually used to model complex relationships between inputs and outputs or to find patterns in data. In more practical terms neural networks are non-linear statistical data modeling or decision making tools. They can be used to model complex relationships between inputs and outputs or to find patterns in data.

Specifically, FIG. 10 shows the results of eighteen device runs from a study in mice of Bio-MOD produced G-CSF. These results were analyzed using ANN. For a quick review, artificial neural networks are computational systems, based on biological neural networks. ANNs have been used in a wide range of applications where extraction of information or patterns from potentially noisy input data is required. Such applications include character, speech and image recognition, document search, time series analysis, medical image diagnosis and data mining. As discussed above, neural networks typically comprise a large number of interconnected nodes. In some classes of neural networks, the nodes are separated into different layers, and the connections between the nodes are characterized by associated weights. Each node has an associated function causing it to generate an output dependent on the signals received on each input connection and the weights of those connections. Neural networks are adaptive, in that the connection weights can be adjusted to change the response of the network to a particular input or class of inputs. Conventionally, artificial neural networks can be trained by using a training set comprising a set of inputs layers, layers and output layers. The goal of training is to tune a network's parameters so that it performs well on the training set and, importantly, to generalize to untrained test data.

In this ANN method, data from the GMP production runs of G-SCF-His, as shown in FIGS. 10A and B (results); the top four principal component weights were extracted and input into a 2-layer feed forward ANN with a 10 hidden neuron layer. The product purity attributes of the corresponding runs where binned into three ranges: (output layers $p_1, p_2, p_3$) greater than 99%, between 98% and 99%, and less than 98%. The ANN was trained with the Levenberg-Marquardt algorithm using 12 runs, validated using 2 runs, and tested using 2 runs. Repeated training of this network gave a high correlation between the multi-sensor data (UV absorbance, Pressure, and Raman spectra) and the product purity estimates (R>0.9) and was able to estimate the correct purity bin with a certainty of at least 90% probability. The learning algorithm demonstrated the ability of the system to predict product purity estimates which closely matched the experimental results as verified by high sensitivity silver strain as shown by the chromatography data shown in FIG.

10B. FIG. 10D shows the ability to predict the correct purity with a certainty of at least 90% probability.

Further, use of vector decomposition methods on a diverse set of batch runs such as sparse Independent Component Analysis (sparse-ICA) and Independent Vector Analysis (IVA) have been shown to extract interpretable features that best represent underlying impurities and system faults across the lifetime of the device. The use of these understandable features as inputs into the model addresses the issue of limited data size and interpretability in the "black box" model for machine learning in the bio-medical field. The addition of all the other sensors as discussed herein makes the Bio-MOD even more robust. A statistically relevant number of "training" runs are used to define the process based on product quality metrics that are determined off-line. The data is rigorously validated with deliberate system perturbations to determine QbD-driven (quality by design) criteria to define operating space where product quality is met and to create product rejection conditions. Thus, a robust, failsafe, machine learning-driven release criterion for each time the system is used to make a biologic. With this approach, a real-time electronic batch record is created for every lot made by every Bio-MOD and used to grow the intelligence of the system with integration of multiple runs over time. Accordingly, each run and batch have a traceable process associated with it for retrospective analysis of any adverse event reported from the biologic This approach allows the evolution of next-generation, deep learning AI-driven systems to biologics Pharmaceutical Quality/CMC and results in systems that are inherently built for continuous quality monitoring and assurance. This offers unprecedented security and traceability down to every single run. Clearly the system is evolvable with additional analytics introduced on-line into Bio-MOD. With the use of machine learning the excessive need for post-run analysis (NMR, Mass Spec) is replaced. The Bio-MOD system of the present invention with the inclusion of machine learning proves that bio-pharma manufacturing can be small-scale, mobile, and robust. With proliferation of multi-sensor data from thousands of small batch runs, machine learning will only become more accurate at estimating quality parameters giving manufactures better ability to perform real-time release.

Methods

Lyophilization and stability testing studies of the IVT components. The IVT system used here has three components: (1) the CHO cell lysate; (2) the reaction mixture; and (3) the dialysis buffer. The CHO cell lysate is an extract from CHO cells and contains the necessary materials for transcription and translation while allowing for shelf stability, which is not possible with live cells. The reaction mixture consists of key ingredients needed for the transcription and translation of the target gene. The dialysis buffer contains reaction supplements that are required to support protein expression in a continuous-exchange cell-free (CECF) system by providing a constant supply of energy-regenerating substrates to maintain the reaction while removing toxic byproducts. All three components of the IVT system were lyophilized and tested for stability and consistency in product generation using tGFP (turbo green fluorescent protein) as the expression model. The liquid CHO cell extracts and buffers were lyophilized with 5% sucrose as a lyoprotectant. Lyophilization volumes of 1 ml for the cell extract and 0.875 ml for the dialysis buffer were put separately in standard 5 ml cylindrical glass vials. For the reaction mixture, 50 ml was lyophilized in a standard 2 ml cylindrical glass vial. Briefly, samples were pre-cooled on frozen shelves kept at −40° C. for 230 min followed by a primary and a secondary drying cycle. The primary freeze drying was carried out at −40° C. for a total of 365 min, while gradually raising the temperature to 0° C. Subsequently, a secondary drying cycle was performed for a total of 540 min, while raising the temperature from 0° C. to 25 C, by which all the tightly-interacting water molecules were removed. At the end of the run, the glass vials were sealed under nitrogen before being removed from the lyophilizer and finally crimped to seal. Stability testing was done in the specific time points indicated by expressing GFP protein using each lyophilized component stored in respective conditions in duplicate. GFP was expressed using duplicate 100 µl reactions for each lyophilized product and quantified by fluorescence relative to a recombinant GFP standard.

Plasmids. The rDNA encoding the recombinant proteins were sub-cloned into the IVT expression vector, pT7CFE1-CHis using NdeI and XhoI restriction sites. The diphtheria toxoid plasmid DT5 was procured from AddGene (cat. no. 11081). Similarly, rDNA for a truncated version of human GADD34, an accessory protein to the IVT reaction, was sub-cloned into pT7CFE1-CMyc vector using NdeI and XhoI restriction sites. Plasmids were transformed into ZYMO DH5α *E. coli* cells. These cells were allowed to proliferate overnight. The next day, plasmid rDNA was isolated using the Zymo-Giga plasmid isolation kit following the manufacturer's guidelines. GADD34 is co-expressed with the protein of interest.

Preparation of IVT reaction. The 1-Step CHO High-Yield IVT Kit (Thermo Fisher Scientific, Rockford, Ill.) is comprised of lyophilized CHO cell lysate and solutions for the reaction mix and dialysis buffer. All components were allowed to come to room temperature. The lyophilized elements were reconstituted with nuclease-free water (NFW) and mixed gently. The components were then added in the following order: 1 ml lysate, 400 µl 5× reaction mix, 8 µg GADD34 plasmid and 80 µg rDNA plasmid. The mixture was brought to a total volume of 2 ml with NFW.

Preparation of CHO microsomes. The microsomes were isolated from the CHO cells as described. In brief, 2.5l of CHOK1 cell culture ($0.6 \times 10^6$ viable cells ml-1) was used and clarified by centrifugation. Following centrifugation at 2,000 g for 5 min at 4° C., the cell pellet was collected and washed with 100 ml of wash buffer (35 mM Hepes-KOH pH 7.5; 140 mM NaCl; 5 mM dextrose). The step was repeated thrice. The cell pellet was then washed with 100 ml of extraction buffer (30 mM Hepes-KOH pH 7.5; 135 mM potassium acetate; 30 mM KCl; 1.65 mM magnesium acetate). Finally, 10 ml of extraction buffer was added to the 10 g cell pellet and lysed using a Dounce homogenizer (four strokes on ice). The collected suspension was clarified by centrifugation at 3,000 g for 10 min. The supernatant was analyzed on a sucrose gradient and by ultracentrifugation. The fractions were collected and stored at −80° C. for further use.

Expression in dialysis cassettes. Reaction components were reconstituted with NFW for CECF protein expression format. The IVT reaction was injected into a 0.5 to 3 ml size, 10 or 20 kDa MWCO Slide-A-Lyzer dialysis cassette (Thermo Fisher Scientific, Rockford, Ill.) using a syringe. The excess air is removed by subsequent suction. Loaded cassettes were then immersed in 25 ml of 1× dialysis buffer individually contained in a modified dialysis bag. The bag was sealed after the excess air was removed and placed horizontally in the onboard shaker incubator that was pre-warmed to 30° C. Reactions were carried out for 6 h with constant shaking at 30 r.p.m. Alternatively, the reactions were placed in a standalone shaker incubator (Certomat BS-1, Sartorius) and carried out for 6 h at 30° C. with constant shaking at 150 r.p.m., except for the EPO reaction, which was kept for 8 h at 28° C.

G-CSF-His expression and purification in *E. coli*. To establish a standard spectrum for NMR spectroscopy, cell-based *E. coil*-derived G-CSF-His was prepared. The NMR spectra of the IVT-derived G-CSF-His was compared with that of the cell-based *E. coli*-derived G-CSF-His. The preparation of the *E. coli*-derived G-CSF-His is described below. *E. coli* expression was carried out using Shuffle express competent *E. coli* cells (NEB Inc., Ipswich, Mass., cat. no. C3028H) using manufacturer's protocols for transformation and expression. Minor variations in the expression protocol were as indicated here: a single colony was grown overnight in 5 ml LB media with ampicillin at 30° C. 1 ml of overnight culture was used to inoculate three 100 ml expressions containing 2× LB media containing 100 µg ml$^{-1}$ ampicillin and incubated at 30° C., until an OD of 0.4-0.8 was reached. Each expression was then induced with 50 µl of a 1 M IPTG stock to achieve a final IPTG concentration of 0.5 mM. The growth temperature was reduced to 16° C. for overnight expression and the *E. coli* cells harvested the next day by centrifuging at 8,000 g for 15 min. The supernatant was discarded and the cells were re-suspended in 5 ml of column buffer 1 (1×PBS, 500 mM NaCl, 10 mM imidazole). The re-suspended cells were placed on ice and lysed by sonication with 5-7 watts, using 30-seconds-on and 1-minute-off cycles. Whole lysate from each of the three expressions was collected (WL1, WL2 and WL3) and centrifuged at 12,000 g for 15 min. The clarified lysate (supernatant) was collected (CL1, CL2 and CL3) and combined to a total of 15 ml, then passed through a 10 ml poly-prep gravity flow column (Bio-Rad, Hercules, Calif.) packed in-house with 1.5 ml HisPur Ni-NTA resin (Thermo Fisher Scientific, Rockford, Ill., cat. no. 88221). The column was preequilibrated with 10 column volumes (CV) of buffer 1. A 15 ml sample of the first flow-through (FT1) was obtained and passed through the column a second time to collect a second flow-through (FT2). The column was washed twice: (1) for 10 CV with buffer 1 and; (2) for 2 CV with buffer 2 (1×PBS, 500 mM NaCl, 50 mM imidazole). Finally, the column was washed four times using 2 ml elution buffer (1×PBS, 500 mM NaCl, 250 mM imidazole) to elute the final protein product collected at a final volume of 8 ml.

Spin purification of His-tagged protein. All materials and reagents were purchased from Thermo Scientific, unless otherwise noted. Purification was done by immobilized metal affinity chromatography (IMAC) using HisPur cobalt spin columns (1 ml) packed in-house with HisPur cobalt resin. Volume ratio of resin to sample was kept at 1:5. Samples were diluted 5 times with binding buffer (10 mM imidazole in PBS, pH 7.4) before loading to the column. Buffers were freshly made and filtered using 0.2 µm filter (Corning, N.Y., USA). Two wash steps were performed; first using the loading buffer, followed by a second buffer containing 30 mM imidazole in PBS. For elution, 150 mM imidazole in PBS buffer was used. Columns were centrifuged using a Sorvall Legend XTR (Thermo Scientific) at 100 g for 1 min at 4° C. after each wash or elution.

Quantitative silver-stained SDS-PAGE. Criterion TGX precast midi protein gel (4-20%) was used in the experiment following standard protocol with a Criterion electrophoresis cell, both obtained from Bio-Rad (cat. no. 1656001 and no. 5671093). For staining gels, ProteoSilver plus silver stain kit (Sigma-Aldrich, cat. no. PROTSIL2) was used. Known concentrations of cell-derived glucose binding protein (GBP), G-CSF (LifeTechnologies) or bovine serum albumin (BSA) were loaded along each sample and used as standard reference for determining the purity and the concentration of purified protein. The area of each band was measured with ImageJ software and the concentration calculated relative to the standard curve. Percent purity was determined also through the same image analysis software by taking the ratio of the area of the known, lowest detectable band versus the total area, where the total area is equal to the area of the lowest detectable protein band plus area of impurities in an overloaded gel.

660 nm assay. Quantitative protein analysis was done using Pierce 660 nm protein assay kit (Thermo Scientific, cat. no. 22660) following the manufacturer's recommended protocol.

Capillary electrophoresis (CE-SDS) of G-CSF (LabChip protein assay). Capillary electrophoresis was done in the LabChip GXII instrument, using a LabChip HT Protein Express 200 assay (PerkinElmer, Hopkinton, Mass.) following the manufacturer's recommended protocol. Samples were denatured at 95° C. (instead of 100° C.) for 5 min.

Reversed-phase high performance liquid chromatography (RP-HPLC) of G-CSF. IMAC-purified samples were analyzed on a Dionex Ultimate 3000 series HPLC system (Thermo Fisher Scientific, Bannockburn, Ill.) using a BioBasic C18 column (Thermo scientific). Mobile phase A consists of 0.1% TFA in water while mobile phase B consists of 0.1% TFA in acetonitrile. Gradient elution of 30-100% B in 25 min at a flow rate of 0.5 ml min$^{-1}$ was used.

Bioactivity assay for G-CSF. The standard method for the in vitro bioassay for G-CSF activity was based on the measurement of cell proliferation utilizing the murine myeloid leukemia cell line NFS-60 (ATCC CRL-1838). The proliferation of NFS-60 cells in response to varying concentrations of standard G-CSF and IVT-produced samples was quantified using the MTT cell proliferation assay kit (ATCC 30-1010 K). Reference standard was purchased from Life Technologies (cat. no. PHC2033) or WHO (NIBSC cat. no. 09/136). Activity results presented here were determined from freshly-produced IVT samples, characterized within 24 h after production. Briefly, yellow 3-(4, 5-dimethylthiazolyl-2)-2, 5-diphenyltetrazolium bromide (MTT) is reduced by dehydrogenase enzymes in metabolically active cells to purple-colored formazan. Addition of SDS detergent disrupts the cells releasing the formazan, which is then quantified by spectrophotometric means. Controls include an IVT blank (without DNA) and a sample boiled at 100° C. for 10 min to destroy G-CSF activity.

Western blot. The G-CSF samples were diluted 10× with PBS. 20 µl aliquots were treated with 6 µl of 5× diluted Laemmli buffer dye, boiled at 100° C. for 5 min, then loaded to a pre-cast 12.5% tris-HCl gel (Bio-rad, cat. no. 3450014) and run at 100 V. Samples were then transferred to a nitrocellulose membrane (Bio-rad, cat. no. 1620233) and left in 20 ml blocking buffer overnight. Primary antibody (Rabbit anti-G-CSF, Abcam, cat. no. 9691) was added at a concentration of 1:3,000 to 20 ml blocking buffer the next day, removed after an hour, and the blot was washed with PBST. Fresh blocking buffer (20 ml) was then added with a complementary HRP-conjugated secondary antibody (Goat Anti-Rabbit HRP, Abcam, cat. no. ab6721) at a concentration of 1:3,000. Solution was removed after 1 h, and the blot was washed with PBST. Finally, a chemiluminescent substrate (Thermo Scientific, cat. no. 34075) was added to the blot and imaged using a Thermo Scientific myECL Imager.

The procedure for the western blot of GBP was similar to that of G-CSF except the anti-His antibody was used for identification.

For the EPO western blot analysis, samples were first treated with PNGase. The PNGase and its components were purchased from New England Biolabs, Mass., USA. Briefly, an 18 µl sample was added to a 1.5 ml Eppendorf tube along with 2 µl of 10× denaturing buffer. The samples were vortexed for 3-5 s and then boiled at 100° C. in a heater (Thermo mixer comfort, USA) for 10 min to enable optimal denaturation. After the 10 min incubation at room temperature, 4 µl of 10× G7 buffer and 4 µl of 10% NP-40 were added to the tube. For reactions with PNGase F, 8 µl of nuclease-free water and 4 µl of PNGase F were added to the reaction. For the reactions without PNGase F, 12 µl of nuclease free water was added and the reaction was incubated at 37° C. for 6 h. Aliquots (20 µl) were treated with 6 µl of 5× diluted Laemmli buffer dye, boiled at 100° C. for 5 min, then loaded to a precast 12.5% Tris-HCl gel (Bio-rad, cat. no. 3450014) and run at 120 V. Samples were then transferred to Polyvinylidene difluoride (Bio-Rad, cat. no. 162-1075) and left in 20 ml blocking buffer for 1 h. Primary antibody (Rabbit anti-EPO, Abcam, cat. no. ab126876) was added at a concentration of 1:3,000 to 20 ml blocking buffer after 1 h in blocking solution. The blot is washed with PBST. Fresh blocking buffer (20 ml) was then added with a complementary HRP-conjugated secondary antibody (Goat Anti-Rabbit HRP, Thermo, cat. no. 31460) at a concentration of 1:3000. Solution was removed after 1 h, and the blot was washed with PBST. Finally, a chemiluminescent substrate (Thermo Scientific, cat. no. 34076) was added to the blot and imaged using a Thermo Scientific myECL Imager.

Quantitative analysis of G-CSF by ELISA. The concentration of G-CSF in the cell extracts was determined using a quantitative Sandwich ELISA (G-CSF Human ELISA, Abcam, USA) following the manufacturer's instructions. All materials required for the analysis was provided in the kit. For the standard, a dilution series containing 0 to 500 pg ml$^{-1}$ of G-CSF standard was prepared. The clarified samples were diluted accordingly with a buffer containing 0.1% BSA in PBS (pH 7.2) and analysed in triplicate. Briefly, 100 µl of each standard and sample was added to appropriate wells and incubated for 2.5 h at room temperature. The wells were washed with wash buffer and added with 100 µl of biotinylated G-CSF antibody and further incubated for 1 h at room temperature. After washing with wash buffer, 100 µl of HRP-streptavidin solution was added to each well and incubated for 45 min at room temperature. Then, 100 µl of TMB substrate solution was added followed by incubation for 30 min, and the reaction subsequently halted by adding 50 µl of stop solution. Finally, absorbance at 450 nm was measured using a SpectraMax M5 Multi-mode microplate reader (Molecular Devices, Sunnyvale, Calif.).

The amount of EPO in the reaction mixtures were determined using the EPO-specific quantitative ELISA kit (Quantikine IVD ELISA, R&D Systems, Minneapolis, Minn., USA) following the manufacturer's instructions. The supernatant was diluted with 0.1% (w/v) BSA in phosphate buffered saline. Standard recombinant EPO ranging from 0-200 mIU ml$^{-1}$ was processed in parallel according to the manufacturer's instructions. Briefly, 100 µl of EPO assay diluent was added to each well followed by 100 µl each standard and sample was added to appropriate wells and incubated for 2 h at room temperature. The wells were aspirated and added 200 µl of conjugate and further incubated for 2 h at room temperature. After washing with wash buffer, 200 µl of substrate solution was added to each well and incubated for 25 min at room temperature, and the reaction subsequently stopped by adding 100 µl of stop solution. Finally, absorbance at 450 nm was measured using a SpectraMax M5 Multi-mode microplate reader (Molecular Devices, Sunnyvale, Calif.).

NMR spectroscopy. Sample preparation. Each NMR spectrum was collected on an 850-MHz NMR spectrometer using 140-300 µl G-CSF-His samples in a 4 mm Shigemi tube (cat. no. BMS-004J, Shigemi Inc., PA) at 27° C. NMR samples were prepared as follows: Immediately after elution from the HisPur column, G-CSF-His fractions were pooled and diluted 5-fold with NMR buffer (50-70 mM sodium phosphate at a pH of 3.5±0.1). This was concentrated to 0.3 ml using to a pre-washed Amicon Ultra-15 centrifugal filtration unit (cat. no. UFC901024, EMD Millipore, Mass.). Solution was further diluted ten-fold with the NMR buffer and re-concentrated; this buffer exchange process was repeated four more times. For the 140 µl sample size, the sample was further concentrated using the Amicon Ultra-0.5 centrifugal filters (cat. no. UFC501024). Final NMR samples contained 95% H$_2$O/5% D$_2$O.

Solution NMR spectroscopy. 1D proton NMR spectra were collected using the standard Presat pulse program available in the Bruker library. Although protein preparation could be scaled up to produce millimolar samples for 2D NMR studies, yields from the IVT process were anticipated to be significantly smaller. To meet this sample limitation, design of the NMR samples and experiments required optimization. Tests of unlabeled lysozyme and ubiquitin standards at 1 mM concentration using the 1H,15N-SOFAST-HMQC pulse program indicated an 8- to 9-fold reduction in acquisition time compared to a standard 1H,15N-HSQC (data not shown). It suggested that the G-CSF-His sample concentration could be lowered to about 0.1 mM if the acquisition time were left at about 20 h. This strategy enabled the successful 1H,15N-SOFAST-HMQC data collection for IVT-produced G-CSF-His at natural abundance of the 15N isotope.

Amino acid sequence analysis. Sample preparation. The lyophilized sample (50-100 µg) was dissolved in 300 µl of 8 M guanidine hydrochloride (pH 8, adjusted with triethylamine), reduced with dithiothreitol (DTT) for 1 h, and alkylated with iodoacetamide (IAA) for 1 h. Solution was then transferred to a 3 kDa MWCO membrane and dialyzed against 5 l of Milli-Q water for 3 h. Water was replaced and the sample was dialyzed again for 16 h. Dialyzed sample was then transferred to a 2 ml tube and evaporated to dryness in a vacuum centrifuge. After drying, the sample was re-suspended in 200 µl of 50 mM ammonium bicarbonate buffer (pH=8) and digested with chymotrypsin (1:50 enzyme-to-substrate ratio) at 37° C. with shaking for 16 h. The reaction was quenched with the addition of 200 µl of 0.1% trifluoroacetic acid (TFA) solution.

Liquid chromatography mass spectrometry (LC-MS) analysis. Analysis was performed on a Thermo Scientific Orbitrap Fusion Tribrid mass spectrometer equipped with an EASY-Spray source and Dionex UltiMate 3000 RSLCnano System using a 50 cm C18 column (EASY-Spray column: 50 cm×75 µm ID, PepMap RSLC C18, 2 µm). 2-4 µl of sample corresponding to ~500 ng of digest material was subjected to analysis over an 80 min linear LC gradient (Start: 97% A, 3% B; End: 55% A, 45% B; A=0.1% formic acid in water; B=0.1% formic acid in acetonitrile). Data was processed using Thermo Scientific Proteome Discoverer 1.2 software. RAW files were searched using Sequest HT search engine against a database containing human, yeast, bovine, E. coli, as well as the sequences of the expressed proteins.

Bio-MOD operation. The Bio-MOD is operated using a program written in LabView. The program includes auto-priming of the pre-assembled bioprocess fluid train with a limited interactive checklist of operations. Following completion of the auto-priming, the Bio-MOD process is fully automated with self-monitoring capabilities, producing the purified sample at the end. The protein is expressed for 6 h in the shaker/incubator (Certomat BS-1, Sartorius) at 30° C. and 150 r.p.m. Briefly, the syringe pumps and their contents are as follows (each buffer is at pH=7.4):

Pump I: lysate from IVT reaction
Pump II: loading/binding/wash buffer 1=1×PBS
Pump III: wash buffer 2=1×PBS+40 mM imidazole+300 mM NaCl
  (For EPO: 1×PBS+0.5% Tween 20+40 mM imidazole+300 mM NaCl)
Pump IV: elution buffer=1×PBS+250 mM imidazole
  (For EPO: 1×PBS+0.5% Tween 20+500 mM imidazole)
Pump V: polishing buffer=20 mM phosphate buffer+50 mM arginine The fluid train is pre-assembled using non-DEHP Tygon tubing (1/16" ID×1/8" OD) and peroxide-cured silicone tubing with barbed luer-lock connections, one-way check-valves, and a microfluidic snake mixer developed in-house. Smaller diameter PTFE tubing (1/32" ID×1/16" OD) is used between the purification column and UV sensors to reduce peak broadening, and barbed 2 psi check valves are connected to all bioprocess outlets to keep the bioprocess pressurized. Disposable BD syringes are filled with the corresponding buffers and mounted onto the syringe pumps. Silicone tubing is used in specific sections where pinch valves are present in the fluidics.

The priming of the fluid train is performed automatically with 3 to 4 interactive dialogue boxes for direct user interaction and to help mitigate issues such as air bubbles and leaks. The final step of the auto-priming includes the insertion of a 1 ml HisPur Cobalt affinity column and a 5 ml HiTrap DEAE Fast Flow polishing column in the system. After insertion, the program pre-saturates the columns with 10 column volumes (CVs) of binding and polishing buffers respectively. After the auto-priming, the UV sensor readings are checked to fall within the acceptable range of 260-300 mV. The program then computes a baseline average for the UV absorbance, and a labelled product vial is placed in the polished sample compartment for automatic collection. The purification script is loaded onto the computer and the automation settings for the purification are reviewed one last time. The bioreactor is removed from the incubator at the end of the 6 h reaction and placed in the Bio-MOD cassette holder. The system is then ready for automated purification and sample collection. The collected product at the end of the process is immediately stored at 4° C. and subsequently characterized offline.

Materials testing for leachables and extractables. The extractable and leachable studies were carried out as per the guidelines in the 'Regulatory Compliance Standardized Extractable Protocol for Single-Use Systems' by the Bio-Phorum Operations Group (BPOG) to screen the materials used in the Bio-MOD processes. The preliminary E&L tests used six solvents 50% ethanol, 0.5 N NaOH, 0.1 M phosphoric acid, 1% PS-80, 5 M NaCl and WFI (water for injection) that were tested on the materials used in the system. The samples were immersed in the solvents with a SA/V of 6:1 at 40° C. for 24 h. The extractables were extracted into the organic dichloromethane and analysed for semi-volatiles using direct injection GC-MS. The peaks were compared with the 1 ppm phenanthrene d-10 as the internal standard. The results indicated that the materials did not have any extractables exceeding the 1 ppm phenanthrene d-10 internal standard. The Slide-A-Lyzer dialysis cassette (bioreactor) was tested for volatiles using Headspace GC-MS and 1 ppm toluene as the internal standard. The results indicated except for the 50% ethanol solvent, there were no volatiles from the dialysis cassette.

Two-dimensional chromatography. For the two-dimensional chromatography method, the first dimension employed a ProPac SAX-10 strong-base anion-exchange column with buffer A consisting of 10 mM Tris and 5% acetonitrile at pH 8.5 and buffer B consisting of 10 mM Tris, 0.5 M NaCl and 5% acetonitrile also at pH 8.5. 80 μl of CHO lysate was used as the feed sample and a flow rate of 0.046 ml min$^{-1}$ was used. After sample injection, the column was washed with 2.4 ml buffer A and then a gradient from 0% buffer B to 50% Buffer B in 322 min was employed followed by a gradient from 50% buffer B to 100% buffer B in 111 min. Every 22 min one fraction of about 1 ml was collected and directed to the second chromatographic dimension. For the second chromatographic dimension an Accucore-150-C4 reversed-phase column was used. Buffer A was composed of 5% acetonitrile in water with 0.1% trifluoroacetic acid (TFA). Buffer B was 0.1% TFA in acetonitrile. A flow rate of 0.4 ml min$^{-1}$ was used and after each injection the column was first washed with 26% buffer B for 1 min, then a gradient from 26% buffer B to 50% buffer B in 8 min was employed, followed by a gradient from 50% B to 95% buffer B in 2 min. After holding at 95% buffer B for 3 min the column was re-equilibrated with 26% buffer B for 8 min and then another sample was injected. To maintain sample stability the whole process was conducted at 5° C.

REFERENCES

The contents of all references cited herein are incorporated by reference herein for all purposes.
1. S. S. Farid, 2007, Process economics of industrial monoclonal antibody manufacture. *J. Chromatogr. B* 848, 8-18.
2. J. Conner et al., 2014, The Biomanufacturing of Biotechnology Products in *Biotechnology Entrepreneurship*. pp. 351-385.
3. Finn, M. in Top Markets Series 2016 (U.S. Department of Commerce, International Trade Administration, http://trade.gov/topmarkets/pdf/Pharmaceuticals_Top_Markets_Reports).
4. Peñalber-Johnstone C, Ge X, Tran K, Selock N, Sardesai N, Gurramkonda C, Pilli M, Tolosa M, Tolosa L, Kostov Y, Frey D D, Rao G. 2017, Optimizing cell-free protein expression in CHO: Assessing small molecule mass transfer effects in various reactor configurations. *Biotechnol Bioeng*. July; 114(7): 1478-1486
5. Tran K, Gurramkonda C, Cooper M A, Pilli M, Tarris J, Selock N, Han T C, Tolosa M, Zuber A, Peñalber-Johnstone C, Dinkins C, Pezeshk N, Kostov Y, Frey D D, Tolosa L, Wood D, Rao G., 2017, Cell-Free Production of a Therapeutic Protein: Expression, Purification, and Characterization of Recombinant Streptokinase Using a CHO Lysate. *Biotechnol Bioeng*. August 26. doi: 10.1002/bit.26439.
6. G. Rao et al., 2016, Microscale bioprocessing system for therapeutic protein on-demand production. U.S. Pat. No. 9,388,373.
7. Adiga R, et al. July 2018. Biological Medicines on Demand: A platform for therapeutic cGMP protein manufacturing at the point-of-care. *Nature Biomedical Engineering*; V.2, 675-686(2018).

8. A. K. Brödel, A. Sonnabend, S. Kubick, 2014, Cell-free protein expression based on extracts from CHO cells. *Biotechnol. Bioeng.* 111, 25-36.
9. C. E. Hodgman, M. C. Jewett, 2012, Cell-free synthetic biology: Thinking outside the cell. *Metab. Eng.* 14, 261-269.
10. Adamo, A. et al. 2016, On-demand continuous-flow production of pharmaceuticals in a compact, reconfigurable system. *Science* 352, 61-67.
11. Pardee, K. et al. 2016, Portable, on-demand biomolecular manufacturing. *Cell* 167, 248-259. e212.
12. Boles, K. S. et al. 2017, Digital-to-biological converter for on-demand production of biologics. *Nat Biotech* 35, 672-675.
13. Airen I O. 2011. Genome-wide functional genomic analysis for physiological investigation and improvement of cell-free protein synthesis. Ph.D. Dissertation, Stanford University.
14. Guo H, Li X, Frey D D. 2014. Development of Chromatofocusing Techniques Using Mixed-Mode Column Packings for Protein Separations. *J. Chromatogr. A,* 1323: 57-65.
15. Guest D W. 1997, Evaluation of simulated moving bed chromatography for pharmaceutical process development, *J. Chromatogr. A,* 760, 159-162.
16. Ng, C. K. S., Rousset, F., Valery, E, bracewell, D. G., Sorensen, E. 2014. Design of high productivity sequential multicolumn chromatography for antibody capture, *Food Bioprocess Processing,* 92, 233-241.
17. Ariffin, A. A. B., Hashim, U., Salam, F., Ishak, Z., Uda, M. N. A., Adam, T. 2014. COMSOL Multiphysics simulation for microfluidic separator as sample delivery system in sensing domain, Proc. Fifth Intern. Conf. Intelligent Systems, *Modelling, and Simulations*, pgs. 183-186.
18. Ward A C, Smith L, de Koning J P, van Aesch Y, Touw I P. 1999. Multiple Signals Mediate Proliferation, Differentiation, and Survival from the Granulocyte Colony-stimulating Factor Receptor in Myeloid 32D Cells, *The Journal of Biological Chemistry,* 274(21): 14956-14962.
19. Panopoulos A D, Watowich S S. 2008, GRANULOCYTE COLONY-STIMULATING FACTOR: MOLECULAR MECHANISMS OF ACTION DURING STEADY STATE AND 'EMERGENCY' HEMATOPOIESIS. *Cytokine.* 42(3): 277-288.
20. Demetri G D, Griffin J D. 1991. Granulocyte colony-stimulating factor and its receptor. *Blood.* 78(11):2791-808.
21. Rossetti M, Gregori S, Roncarolo M G. 2010, Granulocyte-colony stimulating factor drives the in vitro differentiation of human dendritic cells that induce energy in naïve T cells. *Eur J. Immunol.* 40(11): 3097-3106.
22. Gurramkonda C, Mupparapu K, Abouzeid R, Kostov Y, Rao G. 2014, Fluorescence-based method and a device for rapid detection of microbial contamination. *PDA J Pharm Sci Technol.* 68(2): 164-71.
23. Al-Adhami M, Tilahun D, Rao G, Gurramkonda C, Kostov Y. 2017, Rapid Detection of Microbial Contamination Using a Microfluidic Device. *Methods Mol Biol.* 1571:287-299.
24. Yang M, Sun S, Kostov Y, Rasooly A. 2010, Lab-On-a-Chip for carbon nanotubes based immunoassay detection of Staphylococcal Enterotoxin B (SEB). *Lab Chip.* 10(8), 1011-7.
25. Yang, M., Kostov, Y., Bruck, H., Rasooly, A. 2008, Carbon Nanotubes with Enhanced Chemiluminescence (CNT-ECL) Immunoassay for CCD-based Detection of Staphylococcal Enterotoxin B (SEB), *Food. Anal. Chem.* 80(22), 8532-8537.
26. Yang, M., Kostov, Y., Rasooly, A. 2008, Carbon nanotubes based optical immunodetection of Staphylococcal Enterotoxin B (SEB) in food. *Int. J. Food Microbiology* 127(1), 78-83.
27. Lakowicz, J. R. 1999, Principles of Fluorescence Spectroscopy, 2nd ed.; Kluwer Academic/Plenum Publishers: New York.
28. Karhunen, J, et al, 1997, A Class of Neural Networks for Independent Component Analysis, IEEE TRANSACTIONS ON NEURAL NETWORKS, VOL. 8, NO. 3, MAY 1997, pp 486-504
29. Szu, Harold & Hsu, C., 1999, Unsupervised neural network learning for blind sources separation. 30-38. 10.1109/SBRN.1998.730990.

That which is claimed is:

1. A portable and compact cell-free bioprocessing system for the production of on-demand synthesized protein for point-of-care delivery, the system comprising:
    a protein expression module for producing the on-demand synthesized protein, wherein the protein expression module is associated with on-board analytics;
    a protein purification module for purification of the on-demand synthesized protein, wherein the protein purification module is associated with on-board analytics, and wherein the purification module comprises two UV sensors, a multiplicity of programmable syringe pumps, and pressure sensors that generate in-line real-time testing data during a two-step purification process; and
    an artificial intelligence (AI) machine learning module, wherein the on-board analytics comprise multiple sensors for collecting data during the production of the on-demand synthesized protein, to be analyzed by the AI machine learning module, and wherein the AI machine learning module collects and stores in-line real-time testing data of purified protein from the protein purification module and provides information on product quality and potency for each batch of the on-demand synthesized protein relative to previously produced proteins.

2. The portable and compact cell-free bioprocessing system according to claim 1, wherein the protein expression module comprises at least one dialysis cassette or reactor for inclusion of cell lysate, a reaction mixture, and DNA or mRNA for production of the on-demand synthesized protein.

3. The portable and compact cell-free bioprocessing system according to claim 2, wherein the cell lysate is from CHO cells or *E. coli* cells.

4. The portable and compact cell-free bioprocessing system according to claim 2, wherein the cell lysate is combined with a buffer for entry into the protein expression module to provide a homogeneous mixture for entering therein.

5. The portable and compact cell-free bioprocessing system according to claim 2, wherein the reaction mixture comprises at least one of amino acids, nucleotides, co-factors, enzymes, ribosomes, tRNA, polymerases, and transcriptional factors.

6. The portable and compact cell-free bioprocessing system according to claim 5, wherein the reaction mixture further comprises at least one species selected from the group consisting of salts, polymeric compounds, cyclic AMP, inhibitors for protein or nucleic acid degrading enzymes, inhibitors or regulators of protein synthesis, oxidation/reduction adjusters, non-denaturing surfactants, and buffer components.

7. The portable and compact cell-free bioprocessing system according to claim 1, wherein the protein purification module comprises a metal ion affinity chromatography column for initial purification and an ion-exchange chromatography column for a polishing step.

8. The portable and compact cell-free bioprocessing system according to claim 1, wherein each purification process comprises an inline UV sensor comprising an in-line flow cell and light sources and detectors for measuring UV absorbance at about 280 nm to monitor the two-step purification process.

9. The portable and compact cell-free bioprocessing system according to claim 1, wherein the on-board analytics comprise multiple sensors for collecting data during the production process to be analyzed by a cloud based machine learning system.

10. The portable and compact cell-free bioprocessing system according to claim 9, wherein the multiple sensors measure for dissolved oxygen, pH, absorbance, pressure and temperature.

11. The portable and compact cell-free bioprocessing system according to claim 1, wherein the machine learning system uses a blind source separation (BSS) algorithm.

12. The portable and compact cell-free bioprocessing system according to claim 11, wherein the (BSS) algorithm uses independent-component analysis (ICA) that extracts independent source signals when the source signals are active simultaneously and is a BSS algorithm depending on using Artificial Neural Networks.

13. The portable and compact cell-free bioprocessing system according to claim 1, wherein each purification process comprises at least one real-time test selected from the group consisting of absorbance, circular dichroism, fluorescence measurements, and lifetime measurements.

14. The portable and compact cell-free bioprocessing system according to claim 1, wherein the machine learning system is a cloud-based server or a physical server connected to the bioprocessing system.

15. The portable and compact cell-free bioprocessing system according to claim 13, wherein the numerical or analysis data is captured by a smart phone app and transferred through a smartphone to a server for analysis.

16. The portable and compact cell-free bioprocessing system according to claim 13, wherein the numerical or analysis data is evaluated and an output is is provided to the bioprocessing system, wherein the output comprises visual data selected from bar graphs, frequency graphs, and/or audio signals.

17. The portable and compact cell-free bioprocessing system according to claim 1, further comprising a microfluidic mixer positioned between the protein expression module and the protein purification module to mix expressed protein with buffer.

18. The portable and compact cell-free bioprocessing system according to claim 1, wherein UV and pressure sensor profiles are used to estimate purity and concentration of the on-demand synthesized protein, detect production deviations, and reject a batch of the on-demand synthesized protein.

19. A method of analyzing the purity and quality of an on-demand synthesized protein produced in the bioprocessing system of claim 1, the method comprising:
obtaining at least pressure and UV sensor data from the purification module for the on-demand synthesized protein;
transmitting the data to a computer aided classification system;
extracting features from the data with the computer aided classification system to classify the on-demand synthesized protein and process conditions, wherein extracted features characterize the on-demand synthesized protein and such sample characterization is compared to previously characterized extracted features to provide classified features of the on-demand synthesized protein; and
applying an unsupervised clustering process to the classified features to provide a plurality of output clusters to provide enhanced identification of the on-demand synthesized protein during the process.

* * * * *